US009463244B2

(12) United States Patent
Castleberry et al.

(10) Patent No.: US 9,463,244 B2
(45) Date of Patent: Oct. 11, 2016

(54) COMPOSITIONS AND METHODS FOR NUCLEIC ACID DELIVERY

(71) Applicant: Masssachusetts Institute of Technology, Cambridge, MA (US)

(72) Inventors: Steven A. Castleberry, Cambridge, MA (US); Paula T. Hammond, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/201,615

(22) Filed: Mar. 7, 2014

(65) Prior Publication Data

US 2014/0302116 A1 Oct. 9, 2014

Related U.S. Application Data

(60) Provisional application No. 61/900,373, filed on Nov. 5, 2013, provisional application No. 61/790,292, filed on Mar. 15, 2013.

(51) Int. Cl.

| A61K 31/7105 | (2006.01) |
|---|---|
| A61K 9/70 | (2006.01) |
| A61K 45/06 | (2006.01) |
| A61L 27/12 | (2006.01) |
| A61L 27/22 | (2006.01) |
| A61L 27/46 | (2006.01) |
| A61L 31/02 | (2006.01) |
| A61L 31/04 | (2006.01) |
| A61L 31/12 | (2006.01) |
| A61L 31/16 | (2006.01) |

(52) U.S. Cl.
CPC ........... *A61K 45/06* (2013.01); *A61K 31/7105* (2013.01); *A61L 27/12* (2013.01); *A61L 27/22* (2013.01); *A61L 27/46* (2013.01); *A61L 31/026* (2013.01); *A61L 31/047* (2013.01); *A61L 31/127* (2013.01); *A61L 31/16* (2013.01); *A61L 2400/12* (2013.01); *A61L 2420/08* (2013.01)

(58) Field of Classification Search
None
See application file for complete search history.

(56) References Cited

U.S. PATENT DOCUMENTS

| 3,266,987 A | 8/1966 | Crowley et al. |
|---|---|---|
| 3,710,795 A | 1/1973 | Higuchi et al. |
| 3,962,414 A | 6/1976 | Michaels |
| 4,191,811 A | 3/1980 | Hodgdon |
| 4,250,029 A | 2/1981 | Kiser et al. |
| 4,460,563 A | 7/1984 | Calanchi |
| 4,638,045 A | 1/1987 | Kohn |
| 4,794,000 A | 12/1988 | Ecanow |
| 4,806,621 A | 2/1989 | Kohn |
| 4,946,929 A | 8/1990 | D'amore et al. |
| 5,010,167 A | 4/1991 | Eyal Ron |
| 5,019,379 A | 5/1991 | Domb |
| 5,114,719 A | 5/1992 | Sabel et al. |
| 5,208,111 A | 5/1993 | Decher et al. |
| 5,364,634 A | 11/1994 | Lew |
| 5,399,665 A | 3/1995 | Barrera |
| 5,462,990 A | 10/1995 | Hubbell et al. |
| 5,512,131 A | 4/1996 | Kumar et al. |
| 5,512,600 A | 4/1996 | Mikos |
| 5,514,378 A | 5/1996 | Mikos |
| 5,518,767 A | 5/1996 | Rubner et al. |
| 5,536,573 A | 7/1996 | Rubner et al. |
| 5,630,941 A | 5/1997 | Burger et al. |
| 5,660,873 A | 8/1997 | Nikolaychik et al. |
| 5,696,175 A | 12/1997 | Mikos |
| 5,700,559 A | 12/1997 | Sheu et al. |
| 5,714,166 A | 2/1998 | Tomalia et al. |
| 5,716,404 A | 2/1998 | Vacanti |
| 5,716,709 A | 2/1998 | Ferguson et al. |
| 5,736,372 A | 4/1998 | Vacanti |
| 5,770,417 A | 6/1998 | Vacanti |
| 5,797,898 A | 8/1998 | Santini, Jr. et al. |
| 5,804,178 A | 9/1998 | Vacanti |
| 5,807,636 A | 9/1998 | Sheu et al. |
| 5,837,377 A | 11/1998 | Sheu et al. |

(Continued)

FOREIGN PATENT DOCUMENTS

| EP | 0 443 809 | 8/1991 |
|---|---|---|
| EP | 1 116 516 | 7/2001 |

(Continued)

OTHER PUBLICATIONS

Abeloff, M.D. et al., Chapter 95: Cancer of the Breast, in Abeloff's Clinical Oncology, Fourth Edition, pp. 1875-1943, Churchill Livingstone Elsevier (2008).

Abramoff et al., "Image Processing with ImageJ" Biophotonics International 2004, 11, 36-42.

Absolom et al., "Protein adsorption to polymer particles: role of surface properties" J Biomed Mater Res. Feb. 1987;21(2):161-71.

Afonin, K. A. et al. In vitro assembly of cubic RNA-based scaffolds designed in silico. Nature Nanotechnol. 5, 676-682 (2010).

(Continued)

*Primary Examiner* — Jessica Worsham
(74) *Attorney, Agent, or Firm* — Foley Hoag LLP

(57) ABSTRACT

The present invention provides, among other things, multilayer film coating compositions, coated substrates and methods thereof. In some embodiments, a structure includes a substrate; and a multilayer film coated on the substrate, wherein adjacent layers of the multilayer film are associated with one another via one or more non-covalent interactions, wherein the multilayer film comprises a first nucleic acid agent present at a loading density, and further wherein the multilayer film is characterized in that, when the structure is placed on a subject so that the multilayer film contacts cells, the first nucleic acid agent is released with a profile characterized by a feature selected from the group consisting of 1) being a burst-free release; 2) being a sustained release; and 3) exhibiting in vitro and/or in vivo biological effectiveness.

11 Claims, 39 Drawing Sheets

(56) References Cited

U.S. PATENT DOCUMENTS

| | | |
|---|---|---|
| 5,837,752 A | 11/1998 | Shastri |
| 5,858,746 A | 1/1999 | Hubbell et al. |
| 5,902,599 A | 5/1999 | Anseth |
| 5,904,927 A | 5/1999 | Amiji |
| 5,962,520 A | 10/1999 | Smith et al. |
| 6,022,590 A | 2/2000 | Ferguson et al. |
| 6,060,582 A | 5/2000 | Hubbell et al. |
| 6,089,853 A | 7/2000 | Biebuyck et al. |
| 6,095,148 A | 8/2000 | Shastri |
| 6,103,266 A | 8/2000 | Tapolsky et al. |
| 6,114,099 A | 9/2000 | Liu et al. |
| 6,123,681 A | 9/2000 | Brown, III |
| 6,123,727 A | 9/2000 | Vacanti |
| 6,131,211 A | 10/2000 | Hennessey |
| 6,180,239 B1 | 1/2001 | Whitesides et al. |
| 6,235,224 B1 | 5/2001 | Mathiowitz et al. |
| 6,312,727 B1 | 11/2001 | Schacht et al. |
| 6,402,918 B1 | 6/2002 | Schlenoff et al. |
| 6,447,887 B1 | 9/2002 | Claus et al. |
| 6,451,871 B1 | 9/2002 | Winterton et al. |
| 6,479,146 B1 | 11/2002 | Caruso et al. |
| 6,492,096 B1 | 12/2002 | Liu et al. |
| 6,497,729 B1 | 12/2002 | Moussy et al. |
| 6,699,501 B1 | 3/2004 | Neu et al. |
| 6,716,813 B2 | 4/2004 | Lim et al. |
| 6,740,643 B2 | 5/2004 | Wolff et al. |
| 6,743,521 B2 | 6/2004 | Hubbell et al. |
| 6,833,192 B1 | 12/2004 | Caruso et al. |
| 6,860,980 B2 | 3/2005 | Locascio et al. |
| 6,896,926 B2 | 5/2005 | Qiu et al. |
| 6,919,373 B1 | 7/2005 | Lam et al. |
| 6,998,115 B2 | 2/2006 | Langer |
| 7,045,087 B2 | 5/2006 | Kotov |
| 7,045,146 B2 | 5/2006 | Caruso et al. |
| 7,101,575 B2 | 9/2006 | Donath et al. |
| 7,101,947 B2 | 9/2006 | Schlenoff et al. |
| 7,112,361 B2 | 9/2006 | Lynn et al. |
| 7,223,327 B2 | 5/2007 | Schlenoff et al. |
| 7,303,814 B2 | 12/2007 | Lamberti et al. |
| 7,348,399 B2 | 3/2008 | Haynie |
| 7,364,585 B2 | 4/2008 | Weber |
| 7,365,142 B2 | 4/2008 | Schlenoff et al. |
| 7,427,354 B2 | 9/2008 | Eto |
| 7,427,394 B2 | 9/2008 | Anderson |
| 7,491,263 B2 | 2/2009 | Wang et al. |
| 7,879,575 B2 | 2/2011 | Kricka et al. |
| 8,105,652 B2 | 1/2012 | Wood et al. |
| 2002/0053514 A1 | 5/2002 | Locascio et al. |
| 2002/0131933 A1 | 9/2002 | Delmotte |
| 2002/0131951 A1 | 9/2002 | Langer et al. |
| 2002/0187197 A1 | 12/2002 | Caruso et al. |
| 2003/0059398 A1 | 3/2003 | Ranger et al. |
| 2003/0113368 A1 | 6/2003 | Nomoto et al. |
| 2003/0124368 A1 | 7/2003 | Lynn et al. |
| 2004/0013721 A1 | 1/2004 | Antipov |
| 2004/0020423 A1 | 2/2004 | Lewis et al. |
| 2004/0044100 A1 | 3/2004 | Schlenoff et al. |
| 2004/0052865 A1 | 3/2004 | Gower et al. |
| 2004/0149572 A1 | 8/2004 | Schlenoff et al. |
| 2005/0019404 A1 | 1/2005 | Sung et al. |
| 2005/0152955 A1 | 7/2005 | Akhave et al. |
| 2005/0208100 A1 | 9/2005 | Weber et al. |
| 2005/0276841 A1 | 12/2005 | Davis et al. |
| 2006/0127437 A1 | 6/2006 | Kennedy et al. |
| 2006/0198897 A1 | 9/2006 | Pacetti |
| 2006/0216494 A1 | 9/2006 | Furedi-Milhofer et al. |
| 2006/0246112 A1 | 11/2006 | Snyder et al. |
| 2007/0020469 A1 | 1/2007 | Wood et al. |
| 2007/0077276 A1 | 4/2007 | Haynie |
| 2007/0083186 A1 | 4/2007 | Carter et al. |
| 2007/0129792 A1 | 6/2007 | Picart et al. |
| 2007/0141100 A1 | 6/2007 | Sung et al. |
| 2007/0197568 A1 | 8/2007 | Bunn et al. |
| 2007/0276330 A1 | 11/2007 | Beck et al. |
| 2008/0139450 A1 | 6/2008 | Madhyastha et al. |
| 2008/0228280 A1 | 9/2008 | Cohen et al. |
| 2008/0248108 A1 | 10/2008 | Krotz et al. |
| 2008/0311177 A1 | 12/2008 | Hammond et al. |
| 2009/0053139 A1 | 2/2009 | Shi et al. |
| 2009/0061006 A1 | 3/2009 | Leuschner et al. |
| 2009/0088479 A1 | 4/2009 | Allmendinger et al. |
| 2009/0088679 A1 | 4/2009 | Wood et al. |
| 2009/0155326 A1 | 6/2009 | Mack et al. |
| 2009/0170179 A1 | 7/2009 | Lynn et al. |
| 2009/0214615 A1 | 8/2009 | Zhao |
| 2009/0246142 A1 | 10/2009 | Bhatia et al. |
| 2009/0258045 A1 | 10/2009 | Chuang et al. |
| 2009/0263468 A1 | 10/2009 | Mcanjulty et al. |
| 2009/0275906 A1 | 11/2009 | Berland et al. |
| 2010/0003499 A1 | 1/2010 | Krogman et al. |
| 2010/0016439 A1 | 1/2010 | Thomes et al. |
| 2010/0040674 A1 | 2/2010 | Smith et al. |
| 2010/0189683 A1 | 7/2010 | Holmlund et al. |
| 2011/0038939 A1 | 2/2011 | Lvov et al. |
| 2011/0114244 A1 | 5/2011 | Yoo et al. |
| 2011/0143127 A1 | 6/2011 | Gupta et al. |
| 2011/0301209 A1 | 12/2011 | Zaknoen et al. |
| 2012/0027837 A1 | 2/2012 | DeMuth et al. |
| 2012/0058355 A1 | 3/2012 | Lee et al. |
| 2012/0277719 A1 | 11/2012 | Shukla et al. |
| 2012/0277852 A1 | 11/2012 | Shukla et al. |
| 2013/0190890 A1 | 7/2013 | Shah et al. |
| 2013/0273137 A1 | 10/2013 | Mandell et al. |
| 2014/0011759 A1 | 1/2014 | Yaffe et al. |
| 2014/0039575 A1 | 4/2014 | Bradley et al. |

FOREIGN PATENT DOCUMENTS

| | | |
|---|---|---|
| EP | 2 162 283 | 9/2010 |
| EP | 2 566 468 | 3/2013 |
| EP | 2 701 908 | 3/2014 |
| GB | 1213803 | 11/1970 |
| GB | 1213805 | 11/1970 |
| WO | WO 95/11748 | 5/1995 |
| WO | WO 95/34595 | 12/1995 |
| WO | WO 96/03147 | 2/1996 |
| WO | WO 98/03573 | 1/1998 |
| WO | WO 9817330 A1 | 4/1998 |
| WO | WO 98/47948 | 10/1998 |
| WO | WO 99/47253 | 9/1999 |
| WO | WO 99/59647 A1 | 11/1999 |
| WO | WO 00/77281 | 12/2000 |
| WO | WO 01/57118 | 8/2001 |
| WO | WO 01/94441 | 12/2001 |
| WO | WO 02/12888 A2 | 2/2002 |
| WO | WO 02/085500 | 10/2002 |
| WO | WO 03/035716 | 5/2003 |
| WO | WO 2006/051227 | 5/2006 |
| WO | WO 2006/086391 | 8/2006 |
| WO | WO 2007/140391 | 12/2007 |
| WO | WO 2007/140402 | 12/2007 |
| WO | WO 2008/057127 A2 | 5/2008 |
| WO | WO 2008/157372 | 12/2008 |
| WO | WO 2010/021973 | 2/2010 |
| WO | WO 2010/120531 | 10/2010 |
| WO | WO 2011/140136 | 11/2011 |
| WO | WO 2012/149492 | 11/2012 |
| WO | WO 2012/149494 | 11/2012 |
| WO | WO 2013/110047 | 7/2013 |
| WO | WO 2013/163234 | 10/2013 |
| WO | WO 2014/059269 | 4/2014 |
| WO | WO 2014/066862 | 5/2014 |
| WO | WO 2014/150074 | 9/2014 |

OTHER PUBLICATIONS

Ai et al., Biomedical applications of electrostatic layer-by-layer nano-assembly of polymers, enzymes, and nanoparticles Cell Biochem Biophys. 2003;39(1):23-43.

Akinc et al., "Synthesis of poly(beta-amino ester)s optimized for highly effective gene delivery" Bioconjugate Chem. 2003, 14:979-988.

(56) References Cited

OTHER PUBLICATIONS

Akinc, A. et al. A combinatorial library of lipid-like materials for delivery of RNAi therapeutics. Nature Biotechnol. 26, 561-569 (2008).
Albeck, J.G. et al., Modeling a Snap-Action, Variable-Delay Switch Controlling Extrinsic Cell Death, PLoS Biology, 6(12):2831-2852 (2008).
Albrektsson et al., "Osteoinduction, osteoconduction and osseointegration" Eur Spine J. Oct. 2001;10 Suppl 2:S96-101.
Alsberg E, Hill EE, Mooney DJ. Craniofacial tissue engineering. Critical reviews in oral biology and medicine : an official publication of the American Association of Oral Biologists 2001, 12(1): 64-75.
Alsberg E, Kong HJ, Hirano Y, Smith MK, Albeiruti A, Mooney DJ. Regulating bone formation via controlled scaffold degradation. J Dent Res 2003, 82(11): 903-908.
Alvarez-Roman, R., Naik, A., Kalia ,Y. N., Guy, R. H. & Fessi ,H. Skin penetration and distribution of polymeric nanoparticles. J. Controlled ReJease 99 ,53-62,doi:10.1016/j.jconre1.2004.06.015 (2004).
Alves et al., "Self assembling and crosslinking of polyelectrolyte multilayer films of chitosan and alginate studied by QCM and IR spectroscopy" Macromol Biosci. Aug. 11, 2009;9(8):776-85.
Anderson et al., "Semi-Automated Synthesis and Screening of a Large Library of Degradable Cationic Polymers for Gene Delivery," Angew. Chem. Int. Ed. 42:3151-3158 (2003).
Anderson, "Human Gene Therapy" *Nature,* 392: 25-30 (1996).
Anderson, et al., "Biodegradation and Biocompatibility ofPLA and PLGA Microspheres" *Adv. Drug Delivery Rev.* 28: 5-24, 1997.
Ando, et al., "PLGA Micospheres Containing Plasmid DNA: Preservation of Supercoiled DNA via Cryopreparation and Carbohydrate Stabilization" *J. Pharm. Sci.* 88: 126-130, 1999.
Antipov, et al., "Sustained Release Properties of Polyelectrolyte Multilayer Capsules" J. Phys. Chem., 105:2281-2284 (2001).
Ariga et al., "Layer-by-layer assembly as a versatile bottom-up nanofabrication technique for exploratory research and realistic application" Phys Chem Chem Phys. May 21, 2007;9(19):2319-40.
Balabushevich et al., "Protein-loaded microspheres prepared by sequential adsorption of dextran sulphate and protamine on melamine formaldehyde core" J Microencapsul. Nov. 2009;26(7):571-9.
Balko, J.M. et al., Gene expression patterns that predict sensitivity to epidermal growth factor receptor tyrosine kinase inhibitors in lung cancer cell lines and human lung tumors, BMC Genomics, 7:289-302 (2006).
Barrera et al., "Synthesis and RGD peptide modification of a new biodegradable copolymer: poly(lactic acid-co-lysine)" J. Am. Chem. Soc. 115:11010-11011, 1993.
Bass, Brenda L., "RNA Interference the Short Answer", *Nature* 411, 428-429, 2001.
Behr, "Synthetic Gene-Transfer Vectors" Ace. Chem. Res. 26: 274-278, 1993.
Behr, "The Proton Sponge: a Trick to Enter Cells the Viruses Did Not Expoit" *Chimia,* 51: 34-36, 1997.
Benkirane-Jessel et al., "Build-up if Polypeptide Multilayer Coatings with Anti-Inflammatory Properties Based on the Embedding of Piroxicam-Cyclodextrin Complexes," *Advanced Functional Materials.* 14:2, 2004.
Berg et al., "Controlling mammalian cell interactions on patterned polyelectrolyte multilayer surfaces" Langmuir. Feb. 17, 2004;20(4):1362-8.
Bershteyn et al., "Polymer-supported lipid shells, onions, and flowers" Soft Matter 2008, 4, 1787.
Beyer, S., Nickels, P. & Simmel, F.C. Periodic DNA nanotemplates synthesized by rolling circle amplification, Nano Lett 5, 719-722 (2005).
Biggs et al., "The use of nanoscale topography to modulate the dynamics of adhesion formation in primary osteoblasts and ERK/MAPK signalling in STRO-1+ enriched skeletal stem cells" Biomaterials Oct. 2009;30(28):5094-103.

Bins,A. D. et al. A rapid and potent DNA vaccination strategy defined by in vivo monitoring of antigen expression. Nat. Med. (N. Y.,NY,U.5.) 11,899-904,doi:10.1038/nm1264 (2005).
Blacklock et al., "Cross-linked bioreducible layer-by-layer films for increased cell adhesion and transgene expression" J Phys Chem B. Apr. 29;114(16):5283-91.
Boes et al., "T-cell engagement of dendritic cells rapidly rearranges MHC class II transport" Nature 2002, 418, 983-988.
Bonewald et al., "von Kossa staining alone is not sufficient to confirm that mineralization in vitro represents bone formation" Calcif Tissue Int. May 2003;72(5):537-47.
Bott "Applications of "Wired" Enzyme Electrodes," Current Separations, 21(1):3-6 (2004).
Boudou et al., "Internal composition versus the mechanical properties of polyelectrolyte multilayer films: the influence of chemical cross-linking" Langmuir. Dec. 15, 2009;25(24):13809-19.
Boudou et al., "Multiple functionalities of polyelectrolyte multilayer films: new biomedical applications" Adv. Mater., 22(4):441-467 (2010).
Boussif, et al., "A Versatile Vector for Gene and Oligonucleotide Transfer into Cells in Culture and In Vivo: Polyethylenimine" *Proc. Nat/. Acad. Sci, USA,* 92: 7297-7301, 1995.
Brama et al., "Effect of titanium carbide coating on the osseointegration response in vitro and in vivo" Biomaterials. Feb. 2007;28(4):595-608.
Brange et al., "Insulin formulation and delivery" Pharm Biotechnol. 1997;10:343-409.
Brazeau, et al., "In Vitro Myotoxicity of Selected Cationic Macromolecules Used in Non-1 tb 1 Gene Delivery" *Pharm. Res.* 15: 680-684, 1998.
Brewer et al., "Condensation of DNA by spermatid basic nuclear proteins" J Biol Chem. Oct. 11, 2002;277(41):38895-900.
Brewster et al. 2007, "Cyclodextrins as Pharmaceutical Solubilizers," *Advanced Drug Delivery.* 59: 645-666).
Buser et al., "The Crystal Structure of Prussian Blue: Fe4[Fe(CN)5]3XH20," Inorganic D Chemistry, 16(11 ):2704-271 0 (1977).
Calvo et al. "Donnan Permselectivity in Layer-by-Layer Self-Assembled Redox Polyelectrolyte thin film", J. Am. Soc. 124: 8490-8497(2002).
Carey, L.A. et al., "EGFR inhibition with cetuximab added to carboplatin in metastatic triple-negative (basal-like) breast cancer," *Supplement to Journal of Clinical Oncology, ASCO Annual Meeting Proceedings,* TBCRC 001: Clinical Science Symposium, 43S (2009).
Carpenter et al., "A Single-Film Electrochromic Device," J. Electrochem. Soc., 137(8):2464-2467 (1990).
Carpenter, A. E. et al., CellProfiler: image analysis software for identifying and quantifying cell phenotypes, Genome Biology, 7(10):R100-R100.11 (2006).
Carragee EJ, Hurwitz EL, Weiner BK. A critical review of recombinant human bone morphogenetic protein-2 trials in spinal surgery: emerging safety concerns and lessons learned. Spine J 2011, 11(6): 471-491.
Carrell et al., "The aetiology of sperm protamine abnormalities and their potential impact on the sperm epigenome" Int J Androl. Dec. 2008;31(6):537-45.
Caruso, F., "COLL 34-Polymer Design and Assembly for Next-Generation Particle Delivery", Abastracts of Papers American Chemical Society, 237th National Meeting of American Chemical Society, Salt Lake City Utah, Mar. 22, 2009.
Castleberry, S., et al., "Nanolayered siRNA Dressing for Sustained Localized Knockdown," *ACS NANO,* 7(6): 5251-5261 (2013).
Castleberry, S., et al., "Surface Mediated Delivery of siRNA from Layer-By-Layer Assembled Polyelectrolyte Films for the Acceleration of Wound Healing," Abstracts of Papers, 244th National Mtg & Exposition, Aug. 19-23, 2012.
Cavalieri et al., "Assembly and functionalization of DNA-polymer microcapsules" ACS Nano 2009, 3, 234.
Chen, "Preparation, characterization, and electrocatalytic oxidation properties of iron, cobalt, nickel, and indium hexacyanoferrate," Journal of Electroanalytical Chemistry, 521:29-52 (2002).

(56) References Cited

OTHER PUBLICATIONS

Choksakulnimitr et al., "In Vitro Cytotoxicity of Macromolecules in Different Cell Culture Systems" *Controlled Release*, 34: 233-241 (1995).

Chou, T-C. et al., Quantitative Analysis of Dose-Effect Relationshiios: The Combined Effects of Mutiple Drugs or Enzyme Inhibitors, Advances in Enzyme Regulation, 22:27-55 (1984).

Christensen et al., "Heparin coating of the stent graft-effects on platelets, coagulation and complement activation," Biomaterials, 22:349-355 (2001).

Cini et al., "Step-by-step assembly of self-patterning polyelectrolyte films violating (almost) all rules of layer-by-layer deposition" J Am Chem Soc. Jun. 23;132(24):8264-5.

Clark et al., "Selective Deposition in Multilayer Assembly: SAMs as molecular templates," *Supramolecular Science* 4:141, 1997.

Corkery, B. et al., Epidermal growth factor receptor as a potential therapeutic target in triple-negative breast cancer, Annals of Oncology, 20:862-867 (2009).

Cotten, et al., "Receptor-Mediated Transport of DNA into Eukaryotic Cells" *Methods Enzym.* 217:618, 1993.

Crane et al., "Cyclodextrin Inclusion Complexes with a Solvatochromic Flurorescent Probe," *Journal of Chemical Education.* 79(10):1261-1263 (2002).

Crouzier et al., "Ion pairing and hydration in polyelectrolyte multilayer films containing polysaccharides" Biomacromolecules. Feb. 9, 2009;10(2):433-42.

Crouzier T, Sailhan F, Becquart P, Guillot R, Logeart-Avramoglou D, Picart C. The performance of BMP-2 loaded TCP/HAP porous ceramics with a polyelectrolyte multilayer film coating. Biomaterials 2011, 32(30): 7543-7554.

Crystal, "Transfer of Genes to Humans: Early Lessons and Obstacles to Success" *Science*, 270: 404-410 (1995).

Dalby et al., "The control of human mesenchymal cell differentiation using nanoscale symmetry and disorder" Nat Mater. Dec. 2007;6(12):997-1003.

Danhier F, Ansorena E, Silva JM, Coco R, Le Breton A, Preat V. PLGA-based nanoparticles: an overview of biomedical applications. J Control Release 2012, 161(2): 505-522.

Danusso, et al., "Synthesis of Tertiary Amine Polymers" *Polymer*, 11:88-113 (1970).

Daubendiek, S. L., Ryan, K. & Kool, E. T. Rolling-circle RNA-synthesis-circular oligonucleotides as efficient substrates for T7 RNA-polymerase. J. Am. Chem. Soc. 117, 7818-7819 (1995).

Davis et al., "Cyclodextrin-Based Pharmaceutics: Past, Present and Future," *Nature Reviews* (3), 1023-1035 (2004).

Davis et al., "Challenges and potential for RNA nanoparticles (RNPs)" J Biomed Nanotechnol, 5(1):36-44 (2009).

Davis, M. E. et al. Evidence of RNAi in humans from systemically administered siRNA via targeted nanoparticles. Nature 464, 1067-1070 (2010).

de Jonge et al., "The osteogenic effect of electrosprayed nanoscale collagen/calcium phosphate coatings on titanium" Biomaterials. Mar.;31(9):2461-9.

Decher et al., "Buildup of Ultrathin Multilayer Films by a Self-Assembly Process, 1 Consecutive Adsorption of Anionic and Cationic Bipolar Amphiphiles on Charged Surfaces," *Makromol. Chem., Macro mol. Symp.*, 46:321-327 (1991).

Decher et al., "Layer-by-layer assembled multicomposite films," Curr. Opinion Coli. & Interf. Sci. 3:32-39 (1998).

Decher et al., "New nanocomposite films for biosensors: layer-by-layer adsorbed films of polyelectrolytes, proteins or DNA," Biosensors & Bioelectronics, 9:677-684 (1994).

Decher, "Fuzzy Nanoassemblies: Toward Layered Polymeric Multicomposites" *Science*, 277: 1232-1237 (1997).

Decher, et al., "Buildup of Ultrathin Multilayer Films by a Self-Assembly Process: II. Consecutive Adsorption of Anionic and Cationic Bipolar Amphiphiles and Polyelectrolytes on Charged Surfaces," Ber. Bunsenges. Phys. Chem., 95(11):1430-1434 (1991).

Delongchamp " High-Contrast Electrochromism from Layer-By-Layer Polymer Films," Chem. Mater, 15: 1575-1586 (2003).

Delongchamp et al., "Fast Ion Conduction in Layer-By-Layer Polymer Films," Chem. Mater., 15:1165-1173 (2003).

Delongchamp et al., "High-Contrast Electrochromism and Controllable Dissolution of Assembled Prussian Blue/Polymer Nanocomposites," Adv. Funct. Mater., 14(3):224-231 (2004).

Demeneix, et al., "The Proton Sponge: A Trick the Viruses Did Not Exploit," American Chemical Society,146-151 (1996).

DeMuth et al., "Nano-layered microneedles for transcutaneous delivery of polymer nanoparticles and plasmid DNA" Adv Mater. Nov. 16;22(43):4851-6.

DeMuth PC, Min YJ, Huang B, Kramer JA, Miller AD, Barouch DH, et al. Polymer multilayer tattooing for enhanced DNA vaccination. Nature Materials 2013, 12(4): 367-376.

Dent, R. et al., "Triple-Negative Breast Cancer: Clinical Features and Patterns of Recurrence," Clinical Cancer Research, 13: 4429-4434 (2007).

Deshmukh, et al., "Liposome and Polylysine Mediated Gene Transfer" *New J. Chem.* 21: 113-124 (1997).

Diaz, R. et al., "Antitumor and anti angiogenic effect of the dual EGFR and HER-2 tyrosine kinase inhibitor lapatinib in a lung cancer model," *BMC Cancer*, 10:188 (2010).

Diegelman, A. M. & Kool, E. T. Generation of circular RNAs and trans-cleaving catalytic RNAs by rolling transcription of circular DNA oligonucleotides encoding hairpin ribozymes. Nucleic Acids Res. 26, 3235-3241 (1998).

Dimitriou R, Jones E, McGonagle D, Giannoudis PV. Bone regeneration: current concepts and future directions. BMC medicine 2011, 9: 66.

Dimitrova et al., "Sustained delivery of siRNAs targeting viral infection by cell-degradable multilayered polyelectrolyte films" Proc. Natl. Acad. Sci. U. S. A. 2008, 105, 16320.

Dixon, "Quartz crystal microbalance with dissipation monitoring: enabling real-time characterization of biological materials and their interactions" J Biomol Tech. Jul. 2008;19(3):151-8.

Doh, J. & Irvine ,D. J. Photogenerated polyelectrolyte bilayers from an aqueous-processible photoresist for multicomponent protein patterning. J. Am. Chem. Soc. 126, 9110-9171 (2004).

Doh, J. & Irvine, D. J. Aqueous-processible photoresist polymer for multiple protein patterning: Synthesis, characterization and application to T cell activation. PMSE Prepr. 93, 327-328 (2005).

Donatus et al., "Model-based estimates of risks of disease transmission and economic costs of seven injection devices in sub-Saharan Africa" Bull World Health Organ 2002, 80, 859-870.

Dowben, R.M., "General Physiology: A Molecular Approach," *Division of Biological and Medical Sciences*, pp. 142-143, Harper & Row Publishers (1969).

Dubas, et al., "Multiple Membranes from 'True' Polyelectrolyte Multilayers", J. Am. Chem. Soc., 123:5368-5369 (2001).

Dubas, et al., Polyelectrolyte Multilayers Containing a Weak Polyacid: Construction and Deconstruction, *Macromolecules*, 34: 3736-3740 (2001).

Duek et al., "A Solid-State Electrochromic Device Based on Polyaniline, Prussian Blue and an Elastomeric Electrolyte," Advanced Materials, 5(9):650-652 (1993).

Ekins, S. et al., Pathway Mapping Tools for Analysis of High Content Data, Methods in Molecular Biology, 356:319-350 (2007).

Elbakry, A. et al. Layer-by-layer assembled gold nanoparticles for siRNA delivery. Nano Lett. 9, 2059-2064 (2009).

Elbashir, S.M. et al. Duplexes of 21-nucleoties RNAs mediate RNA interference in cultured mammalian cells. Nature 411, 494-498 (20011).

Elbert et al., "Self-assembly and steric stabilization at heterogeneous, biological surfaces using absorbing block copolymers" Chemistry & Biology 5(3): 177-183 (1998).

El-Ghannam et al., "Model surfaces engineered with nanoscale roughness and RGD tripeptides promote osteoblast activity" J Biomed Mater Res A. Mar. 15, 2004;68(4):615-27.

Ellis et al., "Eietrochromism in the Mixed-Valence Hexacyanides. 1. Voltammetric and Spectral Studies of the Oxidation and Reduction of Thin Films of Prussian Blue," *J. Phys. Chem.*, 85:1225-1231 (1981).

(56) References Cited

OTHER PUBLICATIONS

European Search Report of 08771046.3, entitled "Self Assembled Films for Protein and Drug Delivery Applications," dated Oct. 22, 2012, 4 pages.
Facca S, Cortez C, Mendoza-Palomares C, Messadeq N, Dierich A, Johnston AP, et al. Active multilayered capsules for in vivo bone formation. Proc Natl Acad Sci U S A 2010, 107(8): 3406-3411.
Feiler et al., "Adsorption and viscoelastic properties of fractionated mucin (BSM) and bovine serum albumin (BSA) studied with quartz crystal microbalance (QCM-D)" J Colloid Interface Sci. Nov. 15, 2007;315(2):475-81.
Ferruti, e.t al., "Synthesis, Characterisation and Anti tumour Activity of Platinum (II) Complexes of Novel Functionalised Poly (Arnido Amine)s" Macromol. Chem. Phys., 200:1644-1654 (1999).
Ferruti, et al., "Linear Amino Polymers: Synthesis, Protonation and Complex Formation" *Advances in Polymer Science*, 58: 55-92, 1984.
Ferruti, et al., "Recent Results on Functional Polymers and Macromonomers offuterest as Biomaterials or for Biomaterial Modifcation" *Biomaterials*, 15: 1235-1241 (1994).
Ferruti, et al., "Synthesis, Physico-Chemical Properties and Biomedical Applications of Poly(amino-amine)s" Polymer, 26: 1336 (1985).
Fire, et al., "Potent and Specific Genetic Interference by Double-Stranded RNA in Caenorhabditis Elegans" *Nature*, 391: 806-811 (1998).
Fitzgerald, J.B. et al., Systems biology and combination therapy in the quest for clinical efficacy, Nature Chemical Biology, 2(9):458-466 (2006).
Flessner, R.M., et al., "Degradable Polyelectrolyte Multilayers That Promote the Release of siRNA," Langmuir, 27(12): 7868-7876 (2011).
Freiberg et al., "Polymer microspheres for controlled drug release," Int. J. Pharm. 282:1-18 (2004).
Friedman, "Human Gene Therapy—An Immature Genie, But Certainly out of the Bottle" *Nature Med*, 2: 144-147 (1996).
Gao et al., "Layer-by-layer electrodeposition of redox polymers and enzymes on screenprinted carbon electrodes for the preparatioin of reagentless biosensors," ChemComm, (2003).
Gaudet, S. et al., A Compendium of Signals and Responses Triggered by Pro-death and Prosurvival Cytokines, Molecular & Cellular Proteomics, 4:1569-1590 (2005).
Gemici et al., "Hydrothermal treatment of nanoparticle thin films for enhanced mechanical durability" Langmuir. Mar. 4, 2008;24(5):2168-77.
Gerasimov, et al., "Cytosolic Drug Delivery Using pH-and Light~Sensitive Liposomes" *Adv. Drug Delivery Rev.* 38: 317-338, 1999.
Giljohann, D. A., Seferos, D. S., Prigodich, A. E., Patel, P. C. & Mirkin, C. A. Gene regulation with polyvalent siRNA-nanoparticle conjugates. J. Am. Chem. Soc. 131, 2072-2073 (2009).
Gill et al., "Coated microneedles for transdermal delivery" J. Controlled Release 2007, 117, 227-237.
Gill et al., "Cutaneous vaccination using microneedles coated with hepatitis C DNA vaccine" Gene Ther. 2010.
Giudice et al., "Needle-free vaccine delivery" Adv. Drug Delivery Rev. 2006, 58, 68.
Glenn et al., "Transcutaneous immunization and immunostimulant strategies: capitalizing on the immunocompetence of the skin" *Expert Rev. Vaccines*, 2: 253 (2003).
Gonzalez, et al., "New Class ofPolymers for the Delivery ofMacromolecularTherapeutics" *Bioconjugate Chem.* 10: 1068-1074, 1999.
Grabow, W. W., et al., "siRNA delivery: Loaded-up Microsponges," Nature Materials, 11(4): 268-269 (2012).
Grabowski G, Cornett CA. Bone graft and bone graft substitutes in spine surgery: current concepts and controversies. The Journal of the American Academy of Orthopaedic Surgeons 2013, 21(1): 51-60.

Graham, P.D., et al., "Phase inversion dynamics of PLGA solutions related to drug delivery," J Control Release 58(2): 233-245 (1999).
Grayson et al., "Electronic MEMS for triggered drug delivery," Advanced Drug Delivery Reviews, 56:173-184 (2004).
Greenland et al., "Beta-amino ester polymers facilitate in vivo DNA transfection and adjuvant plasmid DNA immunization" *Mol. Ther.* 2005, 12, 164.
Grewal, S. I. & Moazed, D. Heterochromatin and epigenetic control of gene expression. Science 301, 798-802 (2003).
Guo, P. RNA nanotechnology: Engineering, assembly and applications in detection, gene delivery and therapy. J. Nanosci. Nanotechnol. 5, 1964-1982 (2005).
Guo, P. The emerging field of RNA nanotechnology. Nature Nanotechnol. 5, 833-842 (2010).
Guo, P., "Rolling Circle Transcription of Tandem siRNA to Generate Spherulitic RNA Nanoparticles for Cell Entry," Molecular Therapy, Nucleic Acids, 1:3162-2531 (2012).
Habib et al.,"A tungsten-trioxide/prussian blue complementary eletrochromic cell with a polymer electrolyte," *Journal of Applied Electrochemistry*, 21:203-207 (1991).
Habib et al., "Effect of Temperature on a Complementary W03-Prussian Blue Electrochromic System," *J. Electrochem. Soc.*, 139(8):2155-2157 (1992).
Haensler, et al., "Polyamidoamine Cascade Polymers Mediate Efficient Transfection of Cells in Culture" Bioconjugate Chem. 4:372-379, 1993.
Hammond et al., "Fromation of Polymer Microstructures by Selective Deposition of Polyion Multilayers Using Patterned Self-Assembled Monolayers as a Template," *Macromolecules* 28:7569-7571 (1995).
Hammond, "Form and Function in Multilayer Assembly: New Applications at the Nanoscale," Adv. Mater. 16:1271-1293 (2004).
Hanahan, D. et al., The Hallmarks of Cancer, Cell, 100 57-70 (2000).
Hanes, et al., "New Advances in Microsphere-Based Single-Dose Vaccines" *Adv. Drug Delivery Rev.* 28:97-119,1997.
Hansen, et al., "Re-Examination and Further Development of a Precise and Rapid Dye Method for Measuring Cell Growth/Cell Kill" *Immunol. Methods*, 119:203-210, 1989.
Haq et al., "Clinical administration of microneedles: Skin puncture, pain and sensation" *Biomed Microdevices* 2009, 11, 35.
Harper, J.W. et al., The DNA Damage Response: Ten Years After, Molecular Cell, 28(5):739-745 (2007).
Haynie et al., "Protein-inspired multilayer nanofilms: science, technology and medicine" *Nanomedicine.* Sep. 2006;2(3):150-7.
Hehrlein et al., "Drug-eluting stent: the "magic bullet" for prevention of restenosis?" Basic Res Cardiel, 97:417-423 (200:2).
Helfrich, B.A. et al., Antitumor Activity of the Epidermal Growth Factor Receptor (EGFR) Tyrosine Kinase Inhibitor Gefitinib (ZD1839, lressa) in Non-Small Cell Lung Cancer Cell Lines Correlates with Gene Copy Number and EGFR Mutations but not EGFR Protein Levels, Clinical Cancer Research, 12:7117-7125 (2006).
Heller "Redox hydrogel-based electrochemical biosensore," Biosensors, Second Edition, pp. 1-18 (2004).
Hendrix, R. W. Bacteriophage DNA packaging: RNA gears in a DNA transport machine. Cell 94, 147-150 (1998).
Hill, et al., "In Vitro Cytotoxicity ofPoly(amidoamine)s: Relevance to DNA Delivery" Biochim. Biophys. Acta, 1427: 161q 74, 1999.
Hillberg et al., "Effect of genipin cross-linking on the cellular adhesion properties of layer-by-layer assembled polyelectrolyte films" *Biomaterials* Sep. 2009;30(27):4463-70.
Hope, et al., Cationic Lipids, Phosphatidylethanolamine and the Intracellular Delivery of Polymeric, Nucleic Acid-Based Drugs (Review), *Molecular Membrane Technology*, 15: 1-14, 1998.
Hossfeld, S., et al., "Bioactive Coronary Stent Coating Based on Layer-By-Layer Technology for SiRNA release," *Acta Biomaterialia*, 9(5): 6741-6752 (2013).
Itaya et al., "Prussian-blue-modified electrodes: An application for a stable eletrochromic display device," J. Appl. Phys., 53:804-805 (1982).

(56) References Cited

OTHER PUBLICATIONS

Janes, K.A. et al., A Systems Model of Signaling Identifies a Molecular Basis Set for Cytokine-lnduced Apoptosis, Science, 310:1646-1653 (2005).
Janes, K.A. et al., Cytokine-lnduced Signaling Networks Prioritize Dynamic Range over Signal Strength, Cell, 135:343-354 (2008).
Delle et al., "Transmission Spectra of an Electrochromic Window Consisting of Polyaniline, Prussian Blue and Tungsten Oxide," Electrochimica Acta, 38(11 ):1497-1500 (1993).
Jessel et al. Multiple and time-scheduled in situ DNA delivery mediated by B-cyclodextrin embedded in a polyelectrolyte multilayer, Jun. 6, 2006, PNAS, vol. 103, No. 23, pp. 8618-8621.
Jewell et al., "Multilayered polyelectrolyte assemblies as platforms for the delivery of DNA and other nucleic acid-based therapeutics" *Adv. Drug Delivery Rev.* 2008, 60, 979.
Jewell, C. M. et al. Release of Plasmid DNA from Intravascular Stents Coated with Ultrathin Multilayered Polyelectrolyte Films. Biomacromolecules 7, 2483-2491(2006).
Jewell, C. M., Zhang, J., Fredin, N. J. & Lynn ,D. M. Multilayered polyelectrolyte films promote the direct and localized delivery of DNA to cells. J. Controlled Release 106, 214-223 (2005).
Jiang et al., "Selective Deposition in Layer-by-Layer Assembly: Functional Graft," *Langmuir,* 16:8501-8509, (2000).
Johannsmann et al., "Effect of sample heterogeneity on the interpretation of QCM(-D) data: comparison of combined quartz crystal microbalance/atomic force microscopy measurements with finite element method modeling" *Anal Chem.* Dec. 1, 2008;80(23):8891-9.
Johansen, P. et al. Antigen kinetics determines immune reactivity. Proc. Natl. Acad. Sci. U. S. A. 105,5189-5194,doi:10.1073/pnas.0706296105 (2008).
John Wiley and Sons, Lysozyme: Substrate Structure, accessed Oct. 15, 2014, p. 1.
Kabanov, et al., "DNA Complexes with Polycations for the Delivery of Genetic Material inot Cells" Bioconjugate Chem. 6:7-20 (1995).
Kang, N. et al., Inhibition of EGFR signaling augments oridonin-induced apoptosis in human laryngeal cancer cells via enhancing oxidative stress conicident with activiation of both the intrinsic and extrinsic apoptotic pathways, Cancer Letters, 294:147-158 (2010).
Каргина,, О.В. Caтopaсц, ЕшяющиЕСя ВОДОРАСТВОРИМВIЕ ИОНОГЕННЫE ПОЛИМЕРЫ (English Abstract).
Katsuhiko, Sato, et al., (cited as: Sato, K. et al.,) "Layered Assemblies Composed of Sulfonated Cyclodextrin and Poly(allyamine)," Colloid & Polymer Science, 282:287-290 (2003).
Kearney CJ, Mooney DJ. Macroscale delivery systems for molecular and cellular payloads. Nat Mater 2013, 12(11): 1004-1017.
Keselowsky et al., "Integrin alpha(5) controls osteoblastic proliferation and differentiation responses to titanium substrates presenting different roughness characteristics in a roughness independent manner" *J Biomed Mater Res A.* Mar. 1, 2007;80(3):700-10.
Khan Y, Yaszemski MJ, Mikos AG, Laurencin CT. Tissue engineering of bone: material and matrix considerations. J Bone Joint Surg Am 2008, 90 Suppl 1: 36-42.
Khopade et aL, "Electrostatically Assembled Polyelectrolyte/Dendrimer Multilayer Films as Ultrathin Nanoreservoirs," *Nano Letters.* 2:415, (2002).
Kim et al., "Enhanced memory responses to seasonal H1N1 influenza vaccination of the skin with the use of vaccine-coated microneedles" *J Infect Dis* 2010, 201, 190.
Kim et al., "Hydrogen-Bonding Layer-by-Layer-Assembled Biodegradable Polymeric Micelles as Drug Delivery Vehicles from Surfaces" *ACS Nano* 2008, 2, 386.
Kim et al., "MAD (multiagent delivery) nanolayer: delivering multiple therapeutics from hierarchically assembled surface coatings" *Langmuir* 2009, 25, 14086.

Kim, R., Recent Advances in Understanding the Cell Death Pathways Activated by Anticancer Therapy, Cancer, 1 03(8):1551-1560 (2005).
Kinsella CR, Jr., Bykowski MR, Lin AY, Cray JJ, Durham EL, Smith DM, et al. BMP-2-mediated regeneration of large-scale cranial defects in the canine: an examination of different carriers. Plast Reconstr Surg 2011, 127(5): 1865-1873.
Klopman et al., "Recent Methodologies for the Estimation of N-Octanol/Water Partition Coefficents and their Use in the Prediction of Membrane Transport Properties of Drugs," Mini-Reviews in Medicinal Chemistry. 5:127-133, (2005).
Krebs, M.R. et al. The formation of spherulites by6 amyloid fibrils of bovine insulin. Proc Natl Acad Sci USA 101, 14420-14424 (2004).
Krogman et al., Spraying asymmetry into functional membranes layer-by-layer *Nat. Mater.* 2009, 8, 512-518.
Krogman K, Cohen R, Hammond P, Rubner M, Wang B. Industrial-scale spray layer-by-layer assembly for production of biomimetic photonic systems. Bioinspiration & biomimetics 2013, 8(4): 045005.
Kukowska-Latallo, et al., "Efficient Transfer of Genetic Material into Manunalian Cells Using Starburst Polyamidoamine Dendrimers" *Proc. Nat/. Acad. Sci. USA,* 93: 4897-4902, 1996.
Kumar et al., "*Patterning Self-Assembled Monolayers: Applications in Materials Science,*" Langmuir, 10:1498-1511 (1994).
Kwon et al., "Pseudopoly(amino acids): A Study of the Synthesis and Characterization of Poly(trans-4-hydroxy-N-acyi-L-proline esters)," Macromolecules, 22:3250-3255 (1989).
Landes CA, Ballon A, Roth C. Maxillary and mandibular osteosyntheses with PLGA and P(L/DL)LA implants: A 5-year inpatient biocompatibility and degradation experience. Plastic and Reconstructive Surgery 2006, 117(7): 2347-2360.
Langer, "Biomaterials in Drug Delivery and Tissue Engineering: One Laboratory's Experience," *Ace. Chem. Res.* 33:94-101, (2000).
Langer, "Selected Advances in Drug Delivery and Tissue Engineering," *J. Control Release* 62:7-11 (1999).
Lavan et al., "Small-scale systems for in vivo drug delivery," Nature Biotechnology 21 (10):1184-1191 (2003).
Lavos-Valereto et al., "In vitro and in vivo biocompatibility testing of Ti—6Al—7Nb alloy with and without plasma-sprayed hydroxyapatite coating" *J Biomed Mater Res.* 2001;58(6):727-33.
Lee K, Silva EA, Mooney DJ. Growth factor delivery-based tissue engineering: general approaches and a review of recent developments. Journal of The Royal Society Interface 2011, 8(55): 153-170.
Lee, J. S. et al. Gold, poly(_-amino ester) nanoparticles for small interfering RNA delivery. Nano Lett. 9, 2402-2406 (2009).
Lee, J.B., et al., "Self-assembled RNA interference microsponges for efficient siRNA delivery," Nature Materials, 11(4): 316-322 (2012).
Leguen et aL, "Bioactive coatings based on polyelectrolyte multilayer architectures functionalized by embedded proteins, peptides or drugs" *Biomol Eng.,* 24(1):33-41 (2007).
Liang et al., "The minimal functional sequence of protamine" *Biochem. Biophys. Res. Commun.* 2005, 336, 653.
Liao et al., "Response of rat osteoblast-like cells to microstructured model surfaces in vitro" *Biomaterials.* Feb. 2003;24(4):649-54.
Lichter, A.S. et al., Recent Advances in Radiation Oncology., New England Journal of Medicine, 332(6):371-379 (1995).
Lim, et al., "A Self-Destroying Polycationic Polymer: Biodegradable Poly(4-Hydroxy-LProline Ester)" *JAm. Chem. Soc.* 121: 5633-5639, 1999.
Lim, et al., "Cationic Hyperbranched Poly(amino ester): A Novel Class of DNA Condensing Molecule with Catioic Surface, Biodegradable Three-Dimensional Structure, and Tertiary Amine Groups in the Interior" J. Am. Chem. Soc. 2001, 123,2460-61.
Lim, et al., "Development of a Safe Gene Delivery System Using Biodegradable Polymer, Poly [a-(4-Aminobutyl-L-Glycolic Acid]" JAm. Chem. Soc. 122: 6524-6525, 2000.
Lin C-C, Anseth KS. PEG hydrogels for the controlled release of biomolecules in regenerative medicine. Pharmaceutical research 2009, 26(3): 631-643.

(56) References Cited

OTHER PUBLICATIONS

Linhardt, et al., "Free-Radical Synthesis ofPoly(2-Ethylacrylic Acid) Fractions of Low Polydispersity: Effects of Molecular Weight and Polydispersity on the pH-Dependent Conformational Transition in Aqueous Solution" *Macromolecules.* 32: 4457-4459 (1999).
Linhardt, • et al., "pH-Induced Fusion and Lysis ofPhosphatidylcholine Vesicles by Hydrophobic Polyelectrolyte Poly(2-ethylacrylic Acid)" *Langmuir,* 16: 122-127 (2000).
Liu, "Ultrathin Multilayered Films that Promote the Release of Two DNA Constructs with Separate and Distinct Release Profiles" Adv. Mater. 2008, 20 (pp. 4148-4153).
Livingstone et al., "Cationic Hyperbranched Poly(amino ester): A Novel Calss of DNA Condensing Molecule with Cationic Surface, Biodegradable Three-Dimensional Structure, and Tertiary Amine Groups in the Interior, "*J. Curr. Top. Med. Chem.* 3: 1171-1192 (2003).
Lo, H., et al., "Fabrication of controlled release biodegradable foams by phase separation," Tissue Eng. 1(1), 15-28 (1995).
Lopez, J.P. et al., Gefitinib Inhibition of Drug Resistance to Doxorubicin by Inactivating ABCG2 in Thyroid Cancer Cell Lines, Archives of Otolaryngology—Head & Neck Surgery, 133(10):1022-1027 (2007).
Luo, et al., "Synthetic DNA Delivery Systems" *Nat. Biotechnol.* 18: 33-37, 2000.
Lynn et al., "Degradable Poly(β-amino esters): Synthesis, Characterization, and Self-Assembly with Plasmid DNA," *J. Am. Chem. Soc.* 122:10761-10768, (2000).
Lynn et al., "pH-Responsive Polymer Microspheres: Rapid Release of Encapsulated Material Within the Range of Intracellular pH" Angewandte Chemie International Edition 2001, 40, 1707-1710.
Lynn et al., "Degradable poly(b-amino esters): synthesis, characterization, and self-assembly with plasmid DNA" *J. Am. Chem. Soc.* 122:10761-10768, 2000.
Lynn, "Peeling Back the Layers: Controlled Erosion and Triggered Disassembly of Multilayered Polyelectrolyte Thin Films" Adv. Mater. 2007, 19 (pp. 4118-4130).
Lynn, et al., "Accelerated Discovery of Synthetic Transfection Vectors: Parallel Synthesis and Screening of a Degradable Polymer Library" Journal of the American Chemical Society 2001, 123, 8155-8156.
Lynn, et al., Construction of Degradable Thin Films via Layber-by-Layer Deposition of Polyelectrolytes: Fabrication, Characterization, and Application to Controlled Release, MIT Proposal 2001.
MacBeath, G., Protein microarrays and proteomics, Nature Genetics Supplement, 32:526-532 (2002).
Macdonald et al., "Release of a model protein from biodegradable self assembled films for surface delivery applications" *J Control Release.* Nov. 12, 2008;131(3):228-34.
MacDonald, et al.,"Tissue Integration of Growth Factor-Eluting Layer-by-Layer Polyelectrolyte Multilayer Coated Implants," *Biomaterials,* 32(5): 1446-1453 (2010).
Mansouri et al., "Modulating the release kinetics through the control of the permeability of the layer-by-layer assembly: a review" *Expert Opin Drug Deliv.* Jun. 2009;6(6):585-97.
Martin et al., "Solubility and Kinetic Release Studies of Naproxen and Ibuprofen in Soluble Epichlorohydrin-β-cyclodextrin Polymer," *Supramolecular Chemistry.* 18(8): 627-631, (2006).
Martinez, J., Patkaniowska, A., Urlaub, H., Luhrmann, R. & Tuschi, T. Single-stranded antisense siRNAs guide target RNA cleavage n RNAi. Cell 110, 563-574 (2002).
Martino MM, Tortelli F, Mochizuki M, Traub S, Ben-David D, Kuhn GA, et al. Engineering the growth factor microenvironment with fibronectin domains to promote wound and bone tissue healing. Sci Transl Med 2011, 3(100): 100ra189.
Mathiowitz, et al., "Polyanhydride Microspheres as Drug Carriers I. Hot-Melt Microencapsulation" *J. Controlled Release,* 5:13-22 (1987).
Mathiowitz, et al., "Polyanhydride Microspheres as Drug Carriers. II. Microencapsulation" *J. Appl. Polymer Sci.,* 35: 755-774 (1988).

Mehrotra et al., "Time Controlled Protein Release from Layer-by-Layer Assembled Multilayer Functionalized Agarose Hydrogels" *Adv Funct Mater.* Jan. 22;20(2):247-58.
Mendelsohn et al., "Rational design of cytophilic and cytophobic polyelectrolyte multilayer thin films" *Biomacromolecules.* Jan.-Feb. 2003;4(1):96-106.
Michel, et al., "Printing meets lithography: Soft approaches to high-resolution patterning" IBM Journal of Research and Development, 45(5): 697-719 (2001).
Mikos A.G., et al., "Preparation and Characterization of Poly(L-Lactic Acid) Foams," Polymer 35(5): 1068-1077 (1994).
Mikszta et al., "Improved genetic immunization via micromechanical disruption of skin-barrier function and targeted epidermal delivery" *Nat. Med.* 2002, 8, 415.
Milano, G. et al., EGFR-targeting drugs in combination with cytotoxic agents: from bench to bedside, a contrasted reality, British Journal of Cancer, 99:1-5 (2008).
Miller, "Cationic Liposomes for Gene Therapy" Angew. Chem. Int. Ed. 37: 1769-1785, 1998.
Mistry AS, Mikos AG. Tissue engineering strategies for bone regeneration. Regenerative Medicine II. Springer, 2005, pp. 1-22.
Mizushima, N. et al., Methods in Mammalian Autophagy Research, Cell, 140:313-326 (2010).
Mok, H., Lee, S. H., Park, J. W. & Park, T. G. Multimeric small interfering ribonucleic acid for highly efficient sequence-specific gene silencing. Nature Mater. 9, 272-278 (2010).
Montesano, R. et al., Test for Malignant Transformation of Rat Liver Cells in Culture: Cytology, Growth in Soft Agar, and Production of Plasminogen Activator, *Journal of the National Cancer Institute,* 59(6):1651-1658 (1977).
Moor, A., et al., "Proteolytic Activity in Wound Fluids and Tissues Derived from Chronic Venous Leg Ulcers," *Wound Repair and Regeneration,* 17(6): 1067-1927 (2009).
Moran et al., Mixed protein carriers for modulating DNA release. Langmuir. Sep. 1, 2009;25(17):10263-70.
Morgillo, F. et al., Antitumor activity of bortezomib in human cancer cells with acquired resistance to anti-epidermal growth factor receptor tyrosine kinase inhibitors, Lung Cancer, 71:283-290 (2011).
Moriguchi et al., "Synthesis of Ultrathin Films of Prussian Blue by Successive Ion Adsorption Technique," Chemistry Letters, 31 (3):310-311 (2002).
Morris, K.V., Chan, S.W., Jacobsen, S.E. & Looney, D.J. Small interfering RNA-induced transcriptional gene silencing in human cells. Science 305, 1289-1202 (2004).
Moskowitz et al., "The effectiveness of the controlled release of gentamicin from polyelectrolyte multilayers in the treatment of *Staphylococcus aureus* infection in a rabbit bone model" *Biomaterials.* Aug.;31(23):6019-30.
Mulligan, "The Basic Science of Gene Therapy" *Science,* 260: 926-932 (1993).
Murphy, et al., "A Combinatorial Approach to the Delivery of Efficient Cationic Peptoid Reagents for Gene Delivery", *Proc. Natl. Acad. Sci. USA,* 95: 1517-1522 (1998).
Neovius E, Engstrand T. Craniofacial reconstruction with bone and biomaterials: review over the last 11 years. Journal of plastic, reconstructive & aesthetic surgery : JPRAS 2010, 63(10): 1615-1623.
Neve, R.M. et al., A collection of breast cancer cell lines or the study of functionally distinct cancer subtypes, Cancer Cell, 10:515-527 (2006).
Nevins M, Giannobile WV, McGuire MK, Kao RT, Mellonig JT, Hinrichs JE, et al. Platelet-derived growth factor stimulates bone fill and rate of attachment level gain: results of a large multicenter randomized controlled trial. J Periodontol 2005, 76(12): 2205-2215.
Newman et al., "Natural Products as Sources of New Drugs over the Period 1981-2002," *Journal of Natural Products.* 66:1022-1037 (2003).
Nguyen et al., "Extended Release Antibacterial Layer-by-Layer Films Incorporating Linear-Dendritic Block Copolymer Micelles," *Chemistry of Materials.* 19:5524-5530 (2007).

(56) References Cited

OTHER PUBLICATIONS

Niemiec et al., Nanoheterogeneous multilayer films with perfluorinated domains fabricated using the layer-by-layer method. Langmuir. Jul. 20;26(14):11915-20.
O'Donnell, et al., "Preparation ofMicrospheres by the Solvent Evaporation Technique" Adv. Drug Delivery Rev., 28:25-42, 1997.
Oh et al., "Stem cell fate dictated solely by altered nanotube dimension" Proc Natl Acad Sci U S A. Feb. 17, 2009;106(7):2130-5.
Okada, "One-and Three-Month Release Injectable Microspheres of the LH-RH Superagonist Leuprorelin Acetate" Adv. Drug Delivery Rev. 28: 43-70, 1997.
Oliva et al., "Antiproliferative Drug-Eluting Stents: Systematic Review of the Benefits and Estimate of Economic Impact," Rev Esp Cardiel, 57(7):617-628 (2004).
Papanas N, Maltezos E. Benefit-risk assessment of becaplermin in the treatment of diabetic foot ulcers. Drug safety : an international journal of medical toxicology and drug experience 2010, 33(6): 455-461.
Pareta et al., "An understanding of enhanced osteoblast adhesion on various nanostructured polymeric and metallic materials prepared by ionic plasma deposition" J Biomed Mater Res A. Mar. 1;92(3):1190-201.
Park et al., "Biodegradable polymer microneedles: fabrication, mechanics and transdermal drug delivery" J. Controlled Release 2005, 104, 51.
Park et al., "Osteoconductivity of hydrophilic microstructured titanium implants with phosphate ion chemistry" Acta Biomater. Jul. 2009;5(6):2311-21.
Park, J.-H., Allen, M. G. & Prausnitz ,M. R. Polymer microneedles for controlled-release drug delivery. Pharm. Res. 23, 1008-1019 (2006).
Pasco et al., "Characterization of a thermophilic L-glutamate dehydrogenase biosenor for amperometric determination of L-glutamate by flow injection analysis," Biosensors & Biocicctronics, 14:171-178 (1999).
Pashuck ET, Stevens MM. Designing Regenerative Biomaterial Therapies for the Clinic. Science translational medicine 2012, 4(160): 160sr164-160sr164.
Patil, m.L., et al., Surface-modified and internally Cationic polyamidoamine dendrimers for efficient siRNA delivery. Bioconjug Chem 19, 1396-1403 (2008).
Pawson, T. et al., Network medicine., FEBS Letters, 582:1266-1270 (2008).
Pearton et al., "Gene delivery to the epidermal cells of human skin explants using microfabricated microneedles and hydrogel formulations" Pharm. Res. 2008, 25, 407.
Peer, D., P. Zhu, C. V. Carman, J. Lieberman, and M. Shimaoka, Selective gene silencing in activated leukocytes by targeting siRNAs to the integrin lymphocyte function-associated antigen-1. Proc Nat! Acad Sci USA, 2007. 104(10): p. 4095-100.
Peer, D., Park, E. J., Morishita, Y., Carman, C. V. & Shimaoka, M. Systemic leukocyte-directed siRNA delivery revealing cyclin D1 as an anti-inflammatory target. Science 319, 627-630 (2008).
Peerce et al., "Polymer Films on Electrodes, Part Ill. Digital Simulation Model for Cyclic Voltammetry of Electroactive Polymer Film and Electrochemistry of Poly(vinylferrocene) on Platinum," J. Electroanal. Chem, 114:89-115 (1980).
Perou, C.M. et al., Molecular portraits of human breast tumours, Nature, 406:747-752 (2000).
Petrie et al., "The effect of integrin-specific bioactive coatings on tissue healing and implant osseointegration" Biomaterials. Jul. 2008;29(19):2849-57.
Pfeifer et al., "Formulation and surface modification of poly( ester-anhydride) micro-and nanoshperes," Biomaterials, 26:117-124 (2005).
Picart et al., "Molecular basis for the explanation of the expotential growth of polyelectrolyte multilayers" PNAS 99(20):12531-12535 (2002).
Place ES, Evans ND, Stevens MM. Complexity in biomaterials for tissue engineering. Nat Mater 2009, 8(6): 457-470.
Poerner et al., "Drug-coated stents," Minimally Invasive Therapy & Allied Technologies 11(4):185-192 (2002).
Porcel et al., "From exponential to linear growth in polyelectrolyte multilayers" Langmuir. Apr. 25, 2006;22(9):4376-83.
Porcel et al., "Influence of the polyelectrolyte molecular weight on exponentially growing multilayer films in the linear regime" Langmuir. Feb. 13, 2007;23(4):1898-904.
Porter JR, Ruckh TT, Popat KC. Bone tissue engineering: a review in bone biomimetics and drug delivery strategies. Biotechnology Progress 2009, 25(6): 1539-1560.
Prausnitz, "Microneedles for transdermal drug delivery" Adv. Drug Delivery Rev. 2004, 56, 581.
Prausnitz, et al., "Transdermal drug delivery" Nat. Biotechnol., 26: 1261 (2008).
Pruss-Ustun et al., WHO Environmental Burden of Disease Series, World Health Organization, 2003.
Putnam et al., "Poly(4-hydroxy-L-proline ester): Low-Temperature Polycondensation and Plasmid DNA Complexation," Macromolecules, 32:3658-3662 (1999).
Qiu, et al., "Studies on the Drug Release Properties of Polysaccharide Multi layers Encapsulated Ibuprofen Microparticles" Langmuir 17: 5375-5380 (2001).
Quan et al., "Stabilization of influenza vaccine enhances protection by microneedle delivery in the mouse skin" PLoS One 2009, 4, e7152.
Quarles et al., "Distinct proliferative and differentiated stages of murine MC3T3-E1 cells in culture: an in vitro model of osteoblast development" J Bone Miner Res. Jun. 1992;7(6):683-92.
Rajan et al., "Eiectrochromism in the Mixed-Valence Hexacyanides. 2. Kinetics of the Reduction of Ruthenium Purple and Prussian Blue," J. Phys. Chem., 86:4361-4368 (1982).
Ramaswamy et al., "Sphene ceramics for orthopedic coating applications: an in vitro and in vivo study" Acta Biomater. Oct. 2009;5(8):3192-204.
Rao, et al., "Poly (Butaneodiol Spermate): A Hydrolytically Labile Polyester-Based Nitric Oxide Carrier" J. Bioactive and Compatible Polymers 14: 54-63, 1999.
Rausch-fan et al., "Differentiation and cytokine synthesis of human alveolar osteoblasts compared to osteoblast-like cells (MG63) in response to titanium surfaces" Dent Mater. Jan. 2008;24(1):102-10.
Razzacki et al., "Integrated microsystems for controlled drug delivery," Advanced Drug Delivery Reviews, 56:185-198 (2004).
Richards, K. E., Williams, R. C. & Calendar, R. Mode of DNA packing within bacteriophage heads. J. Mol. Biol. 78, 255-259 (1973).
Richert et al., "Cell interactions with polyelectrolyte multilayer films" Biomacromolecules. Nov.-Dec. 2002;3(6): 1170-8.
Roach et al., "Interpretation of protein adsorption: surface-induced conformational changes" J Am Chem Soc. Jun. 8, 2005;127(22):8168-73.
Roach et al., "Modern biomaterials: a review—bulk properties and implications of surface modifications" J Mater Sci Mater Med. Jul. 2007;18(7):1263-77.
Roberts, et al., "Preliminary Biological Evaluation ofPolyamidoamine (P AMAM) Starburst TM Dendrimers" J. Biomed. Mater. Res. 30: 53-65, 1996.
Robin et al., "The Color and Electronic Configurations of Prussian Blue," Electronic Configurations of Prussian Blue, 1( 2):337-342 (1962).
Rohanizadeh, R., et al., "Gelatin Sponges (Gelfoam®) as a scaffold for Osteoblasts", J. Mater Sci. Mater Med., 19:1173-1182 (2008).
Rusnak, D.W. et al., Assessment of epidermal growth factor receptor (EGFR, ErbB1) and HER2 (ErbB2) protein expression levels and response to lapatinib (Tykerb®, GW572016) in an expanded panel of human normal and tumour cell lines, Cell Proliferation, 40: 580-594 (2007).
Sachs, K. et al., Casual Protein-Signaling Networks Derived from Multiparameter Single-Cell Data, Science, 308:523-529 (2005).
Saha et al., "Designing synthetic materials to control stem cell phenotype" Curr Opin Chem Biol. Aug. 2007;11(4):381-7.

(56) References Cited

OTHER PUBLICATIONS

Sallusto, F., Geginat, J. & Lanzavecchia, A. Central memory and effector memory T cell subsets: Function, generation, and maintenance. Annu. Rev. Immunol. 22 ,145-163, doi:10.1146/annurev.immunol.22.012103.104102 (2004).
Samuel, R. E. et al. Osteoconductive protamine-based polyelectrolyte multilayer functionalized surfaces. Biomoteriols 32,1491-1502,dol:10.1016/j.biomaterials.2011.06.032 (2011).
Sanford, "The Biolistic Process" Trends Biotechnol. 6:288-302, 1988.
Santini et al., "Microchips as Controlled Drug-Delivery Devices," Angew. Chem. Int. Ed., 39:2396-2407 (2000).
Santini et al., "Microchips for drug delivery," Abstracts of Papers of the American Chemical Society, 219(174):U34-U34 (2000).
Sapi, E. et al., Ets-2 Transdominant Mutant Abolishes Anchorage-independent Growth and Macrophage Colony-stimulating Factor-stimulated Invasion by BT20 Breast Carcinoma Cells, Cancer Research, 58:1027-1033 (1998).
Schaffer, et al., "Vector Unpacking as a Potential Banier for Receptor-Mediated Polyplex Gene Delivery" *Biotechnol. Bioeng.*, 61: 598-606 (000).
Schechter, A.L. et al., The neu oncogene: an erb-8-related gene encoding a 185,000-Mr tumour antiQen, Nature, 312:513-516 (1984).
Schlenoff, "Retrospective on the future of polyelectrolyte multilayers" *Langmuir.* Dec. 15, 2009;25(24):14007-10.
Schmidt et al., "Electrochemically controlled swelling and mechanical properties of a polymer nanocomposite" *ACS Nano.* Aug. 25, 2009;3(8):2207-16.
Schmitz JP, Hollinger JO. The Critical Size Defect as an Experimental-Model for Craniomandibulofacial Nonunions. Clinical Orthopaedics and Related Research 1986(205): 299-308.
Schuler "Decomposable Hollow Biopolymer-Based Capsules" Biomacromolecules, vol. 2, 2001 921-26.
Schwarz et al., "Potential of chemically modified hydrophilic surface characteristics to support tissue integration of titanium dental implants" *J Biomed Mater Res B Appl Biomater.* Feb. 2009;88(2):544-57.
Schweikl, et al., "Triethylene Glycol Dimethacrylate Induces Large Deletions in the Hprt Gene of V79 Cells" *Mutat. Res.* 438: 71-78 (1999).
Seeman, N. C. Nanomaterials based on DNA. Annu. Rev. Biochem. 79, 65-87 (2010).
Semple, S. C. et al. Rational design of cationic lipids for siRNA delivery. Nature Biotechnol. 28, 172-176 (2010).
Sengupta, S. et al., Temporal targeting of tumor cells and neovasculature with a nanoscale delivery system, Nature, 436:568-572 (2005).
Seo et al., "Effect of the layer-by-layer (LbL) deposition method on the surface morphology and wetting behavior of hydrophobically modified PEO and PAA LbL films" *Langmuir.* Aug. 5, 2008;24(15):7995-8000.
Sevecka, M. et al., State-based discovery: a multidimensional screen for small-molecule modulators of EGF signaling, Nature Methods, 3(1 0):825-831 (2006).
Seyhan, A. A., et al., "RNA interference from Multimeric shRNSs generated by rolling circle transcripotion," *Oligonucleotides*, 16(4): 353-363 (2006).
Shah NJ, Hyder MN, Moskowitz JS, Quadir MA, Morton SW, Seeherman HJ, et al. Surface-Mediated Bone Tissue Morphogenesis from Tunable Nanolayered Implant Coatings. Science Translational Medicine 2013, 5(191).
Shiratori et ai., "pH-Dependent Thickness Behavior of Sequentially Adsorbed Layers of Weak Polyelectrolytes," Macormolecules, 33:4213-4219 (2000).
Shukla et al., "Tunable Vancomycin Releasing Surfaces for Biomedical Applications", Small Nano Mirco, 2010, 21 (6), 2392-2404.
Shukla et al., "Controlling the release of peptide antimicrobial agents from surfaces" *Biomaterials.* Mar. 2010;31(8):2348-2357.

Shutava et al., "Layer-by-Layer-Coated Gelatin Nanoparticles as a Vehicle for Delivery of Natural Polyphenols" *ACS Nano.* Jul. 28, 2009;3(7):1877-85.
Singh, et al., "Cationic Microparticles: A Potent Delivery System for DNA Vaccines" *Proc. Nat/. Acad. Sci. USA*, 97: 811-816,2000.
Slamon, D.J. et al., Human Breast Cancer: Correlation of Relapse and Survival with Amplification of the HER-2/neu Oncogene, Science, 235:177-182 ( 1987).
Smiell JM, Wieman TJ, Steed DL, Perry BH, Sampson AR, Schwab BH. Efficacy and safety of becaplermin (recombinant human platelet-derived growth factor-BB) in patients with nonhealing, lower extremity diabetic ulcers: a combined analysis of four randomized studies. Wound repair and regeneration : official publication of the Wound Healing Society [and] the European Tissue Repair Society 1999, 7(5): 335-346.
Smith et al., "Layer-by-Layer Platform Technology for Small-Molecule Delivery", Angew.Chem.lnt.Ed., 2009, 48, 8974-8977, with English Abtract.
Smith, K. A. et al. Enhancing ONA vaccination by sequential injection of lymph nodes with plasmid vectors and peptides. Vaccine 27,2603-2615,doi:10.1016/j.vaccine.2009.02.038 (2009).
Smith, K. A. et al. Multivalent immunity targeting tumor-associated antigens by intra-lymph node DNA-prime ,peptide-boost vaccination. Cancer Gene Ther. 18, 63-76,doi:10.1038/cgt.2010.45 (2011).
Song, Jie, et al., "Growth of endothelial cell on the surface of intravascular sent material: Bionic construction of bioactive extracellular matrix", Journal of Clinical Rehabilitative Tissue Engineerinq Research, Oct. 22, 2009, 13(43), 8425-8431.
Sordella, R. et al., Gefitinib-Sensitizing EGFR Mutations in Lung Cancer Activate Anti-Apoptotic Pathways, Science, 305:1163-1167 (2004).
Spicer PP, Kretlow JD, Young S, Jansen JA, Kasper FK, Mikos AG. Evaluation of bone regeneration using the rat critical size calvarial defect. Nature protocols 2012, 7(10): 1918-1929.
Stevens MM. Biomaterials for bone tissue engineering. Materials Today 2008, 11(5): 18-25.
Strathmann H. Membrane separation processes: current relevance and future opportunities. AIChE Journal 2001, 47(5): 1077-1087.
Stubbs, Milton T., et al, Eur. J. Biochem. 2006 (1992), pp. 187-195.
Su et al., "Layer-by-layer-assembled multilayer films for transcutaneous drug and vaccine delivery" *ACS Nano* 2009, 3, 3719-3729.
Subramanian, A. et al., Gene set enrichment analysis: A knowledge-based approach for interpreting genome-wide expression profiles, Proceedings of the National Academy of Sciences of the USA, 102(43):15545-15550 (2005).
Sullivan Sean, P. et al. Dissolving polymer microneedle patches for influenza vaccination. Nat Med 16, 915-920.
Sullivan, S. P.,Murthy, N. & Prausnitz ,M. R. Minimally invasive protein delivery with rapidly dissolving polymer microneedles. Adv. Mater. 20, 933-938 (2008).
Sun, T. et al., Activation of Multiple Proto-oncogenic Tyrosine Kinases in Breast Cancer via Loss of the PTPN12 Phosphatase, Cell, 144:703-718 (2011).
Tang, et al., "Adhesion and endothelialization of endothelial cells on the surface of endovascular stents by the novel rotational culture of cells," Applied Surface Science, 255:315-319 (2008).
Tang, et al., "In Vitro Gene Delivery by Degraded Polyamidoamine Dendrimers" *Bioconjugate Chem.* 7:703-714, 1996.
Taratula, O. et al. Surface-engineered targeted PPI dendrimer for efficient intracellular and intratumoral siRNA delivery. J. Control. Release 140, 284-293 (2009).
Tetko et al., "Virtual Computational Chemistry Laboratory-design and description," *Computer-Aided Mol. Des.* 19: 453-463, (2005).
Thompson et al., "Biochemical functionalization of polymeric cell substrata can alter mechanical compliance" *Biomacromolecules.* Jun. 2006;7(6):1990-5.
Thompson et al., "Tuning compliance of nanoscale polyelectrolyte multilayers to modulate cell adhesion" *Biomaterials.* Dec. 2005;26(34):6836-45.
Tijsterman, M., Ketting, R. F. & Plasterk, R. H. The genetics of RNA silencing. Annu. Rev. Genet. 36, 489-519 (2002).

(56) References Cited

OTHER PUBLICATIONS

Toniolo et al., "II. Circular dichroism study of the three main components of clupeine" *Biochim Biophys Acta.* Feb. 26, 1979;576(2):429-39.

Trubetskoy, V. S., Loomis, A., Hagstrom, J. E., Budker, V. G. & Wolff, J. A. Layer-by-layer deposition of oppositely charged polyelectrolytes on the surface of condensed DNA particles. Nucleic Acids Res. 27, 3090-3095 (1999).

Turner, J.G. et al., ABCG2 expression, function, and promoter methylation in human multiple myeloma, Blood, 108(12):3881-3889 (2006).

Uhrich et al., "Polymeric Systems for Controlled Drug Release," *Chem. Rev.* 99:3181-3198 (1999).

Uhrich, K., "Hyperbranched Polymers for Drug Delivery" Trends Polym. Sci. 5: 388-393 (1997).

van de Wetering, et al., "Structure-Activity Relationships of Water-Soluble Cationic Methacrylate/Methacrylamide Polymers for Non viral Gene Delivery" *Bioconjugate Chem.* 10: 589-597, 1999.

Vazquez et al., "Variation of polyelectrolyte film stiffness by photo-cross-linking: a new way to control cell adhesion" *Langmuir.* Apr. 9, 2009;25(6):3556-63.

Vittal et al., "Surfactant Promoted Enhancement on Electrochemical and Electrochromic Properties of Films of Prussian Blue and Its Analogs," Journal of The Electrochmical Socitey, 146(2):786-793 (1999).

Vo TN, Kasper FK, Mikos AG. Strategies for controlled delivery of growth factors and cells for bone regeneration. Adv Drug Deliv Rev 2012, 64(12): 1292-1309.

Wang D., et al., "Synthesis and evaluation of water-soluble polymeric bone-targeted drug delivery systems," Bioconjugate Chemistry 14(5): 853-859 (2003).

Wang et al., "A Novel Biodegradable Gene Carrier Based on Polyphoophoester," J. Am. Chem. Soc. 123:9480-9481 (2001).

Wang, P. M., Cornwell, M., Hill, J. & Prausnitz ,M. R. Precise Microinjection into Skin Using Hollow Microneedles. J. Invest. Dermatol. 126,1080-1087,doi:10.1038/sj.jid.5700150 (2006).

Warner, T.D., et al., "Nonsteroid Drug Selectives for Cyclo-Oxygenase-1 Rather Than Cyclo-Oxygenase-2 are associated with Human Gastrointestinal Toxicity: A full in vitro Analysis," *Proceedings of the National Academy of Sciences of the United States of America,* 96: 9966 (1999).

Watts NB, Diab DL. Long-Term Use of Bisphosphonates in Osteoporosis. J Clin Endocr Metab 2010, 95(4): 1555-1565.

Wick, D. A., Martin, S. D., Nelson, B. H. & Webb ,J. R. Profound CD8+ T cell immunity elicited by sequential daily immunization with exogenous antigen plus the TLR3 agonist poly(I:C). Vaccine 29, 984-993, doi:10.1016/j.vaccine.2010.11.036 (2011).

Wikipedia, Heparin, accessed Oct. 15, 2014, pp. 1-18.

Will J, Melcher R, Treul C, Travitzky N, Kneser U, Polykandriotis E, et al. Porous ceramic bone scaffolds for vascularized bone tissue regeneration. Journal of Materials Science: Materials in Medicine 2008, 19(8): 2781-2790.

Winer, E.P. et al., Optimizing Treatment of "Triple-Negative" Breast Cancer. SABCS 2007: Improving Outcomes in Advanced and Meta-static Breast Cancer, http://www.medscape.org/viewarticle/569483 (2007).

Woeblecke, H. et al., Reversal of breast cancer resistance protein-mediated drug resistance by tryprostatin A, International Journal of Cancer, 107:721-728 (2003).

Wood et al., "Controlling Interlayer Diffusion to Achieve Sustained, Multiagent Delivery from Layer-by-Layer Thin Films," *Proceedings of the National Academy of Sciences of the United States of America,* 103(27):10207-10212 (2006).

Wood et al., "Tunable drug release from hydrolytically degradable layer-by-layer thin films" *Langmuir.* Feb. 15, 2005;21(4):1603-9.

Wood, E.R. et al., A Unique Structure for Epidermal Growth Factor Receptor Bound to GW572016 (Lapatinib): Relationships among Protein Conformation, Inhibitor Off-Rate, and Receptor Activity in Tumor Cells, *Cancer Research,* 64:6652-6659 (2004).

Woodruff MA, Lange C, Reichert J, Berner A, Chen F, Fratzl P, et al. Bone tissue engineering: from bench to bedside. Materials Today 2012, 15(10): 430-435.

Yang, et al., "A New Approach to Identifying Genotoxic Carcinogens: p53 Induction as an Indicator ofGenotoxic Damage" *Carcinogenesis,* 19: P1117-P1125, 1998.

Yoon, C-H. et al., Activation of p38 Mitogen-Activated Protein Kinase Is Required for Death Receptor-Independent Caspase-8 Activation and Cell Death in Response to Sphingosine, Molecular Cancer Research, 7(3):361-370 (2009).

Zauner, et al., "Polylysine-Based Transfection Systems Utilizing Receptor-Mediated Delivery" *Adv. Drug. Del. Rev.* 30: 97-113, 1998.

Zhang, J., et al., "Multilayered Thin Films that Sustain the Release of Functional DNA under Physiological Conditions," Langmuir, 20(19): 8015-8021 (2004).

Zhang,J., Fredin, N. J., Janz, J. F. , Sun, B. & Lynn, D. M. Structure/property relationships in erodible multilayered films: influence of polycation structure on erosion profiles and the release of anionic polyelectrolytes. Langmuir 22, 239-245, doi:10.1021/1a052360b (2006).

Zheng et al., "Controlling cell attachment selectively onto biological polymer-colloid templates using polymer-on-polymer stamping" *Langmuir.* Aug. 17, 2004;20(17):7215-22.

Zang, Y., et al., "In Vitro Observations of Self-Assembled ECM-Mimetic Bioceramic Nanoreservoir Delivering rFN/CDH to Modulate Osteogenesis", Biomaterials, 33(30): 7468-7477 (2012).

Zhou, et al., "Preparation ofPoly(L-serine ester): A Structural Analogue of Conventional Poly(L-serine)" *Macromolecules,* 23: 3399-3406, 1990.

International Preliminary Examination Report for PCT/US2002/34191, entitled: Methods of Making Decom\osable Thin Films of Polyelectrolytes and Uses Thereof, Date of completion of report: Sep. 11, 2003.

International Preliminary Report on Patentability and Written Opinion for PCT/US2009/054011, entitled: Controlled Delivery of Bioactive Agents From Decomposable Films: Date of issuance: Feb. 22, 2011.

International Preliminary Report on Patentability and Written Opinion for PCT/US2012/035689, entitled: Coating Compositions, Methods and Coated Devices, Date of Issuance: Oct. 29, 2013.

International Preliminary Report on Patentability for PCT/US08/66948, entitled: Self Assembled Films for Protein and Drug Delivery Applications: Date of Issuance: Dec. 17, 2009.

International Preliminary Report on Patentability for PCT/US2006/004295, entitled: Electrochemically Degradable Layer-By-Layer Thin Films, Date of Issuance: Aug. 7, 2007.

International Preliminary Report on Patentability for PCT/US2007/069937, entitled: Methods of Making Decomposable Thin Films of Polyelectrolytes and Uses Thereof, Date of Issuance: Dec. 3, 2008.

International Preliminary Report on Patentability for PCT/US2007/69964, entitled: Methods of Making Decomposable Thin Films of Polyelectrolytes and Uses Thereof, Date of Issuance: Dec. 3, 2008.

International Preliminary Report on Patentability for PCT/US2011/035057, entitled: Drug Deliver Coating and Devices, Date of issuance: Nov. 6, 2012.

International Preliminary Report on Patentability for PCT/US2012/035692, entitled: Coating Compositions, Methods and Coated Devices, Date of Issuance: Oct. 29, 2013.

International Preliminary Report on Patentability for PCT/US2013/37869, entitled: Stable Layer-By-Layer Coated Particles, Date of Mailing: Nov. 6, 2014.

International Preliminary Report on Patentability for PCT/US2013/037868, entitled: Compositions and Methods of Treatment of Drug Resistant Cancers, Date of Mailing: Nov. 20, 2014.

International Preliminary Report on patentability for PCT/US2013/022430, entitled: Compositions and Methods for Coating, Date of mailing: Jul. 22, 2014.

International Search Report and Written Opinion for PCT/US2007/69964, entitled: Methods of Making Decomposable Thin Films of Polyelectrolytes and Uses Thereof, Date of Issuance: Oct. 29, 2007.

(56) References Cited

OTHER PUBLICATIONS

International Search Report for PCT/US08/66948: entitled: Self Assembled Films for Protein and Drug Delivery Applications: Date of Mailing: Aug. 29, 2008. (incorrectly cited as Aug. 23, 2008).
International Search Report for PCT/US2002/34191, entitled: Methods of Making Decomposable Thin Films of Polyelectrolytes and Uses Thereof, Date mailed: Jan. 17, 2003.
International Search Report for PCT/US2006/004295, entitled: Electrochemically Degradable Layer-By-Layer Thin Films, Date of Issuance: Oct. 2, 2006.
International Search Report for PCT/US2007/069937, entitled: Methods of Making Decomposable Thin Films of Polyelectrolytes and Uses Thereof, Date of mailing: Aug. 13, 2008.
International Search Report for PCT/US2009/054011, entitled: Controlled Delivery of Bioactive Agents From Decomposable Films: Date of mailing: Nov. 24, 2010.
International Search Report for PCT/US2011/035057, entitled: Drug Deliver Coating and Devices, Date of mailing: Feb. 8, 2012.
International Search Report for PCT/US2012/035689, entitled: Coating Compositions, Methods and Coated Devices, Date of Mailing: Jul. 31, 2012.
International Search Report for PCT/US2012/35692, entitled: Coating Compositions, Methods and Coated Devices, Date of Mailing: Oct. 5, 2012.
International Search Report for PCT/US2013/022430, entitled: Compositions and Methods for Coating, Date of mailing: May 15, 2013.
International Search Report for PCT/US2013/066980, entitled: Devices and Methods for Layer-by-Layer Assembly, Date of Mailing: Apr. 30, 2014.
International Search Report for PCT/US2013/37868, entitled: Compositions and Methods of Treatment of Drug Resistant Cancers, Date of Mailing: Sep. 6, 2013.
International Search Report for PCT/US2013/37869, entitled: Stable Layer-By-Layer Coated Particles, Date of Mailing: Sep. 13, 2013.
International Search Report for PCT/US2014/018284, entitled:Nucleic Acid Particles, Methods and Use Thereof, Date of mailing: Jul. 30, 2014.
International Search Report for PCT/US2014/022107, entitled: Compositions and Methods for Nucleic Acid Delivery, Date of mailing: Jun. 5, 2014.
International Search Report for PCT/US2014/057496, entitled: Biodegradable Layer-by-Layer (LbL) Films for Cell Capture and Release, Date of mailing: Jan. 8, 2015.
Written Opinion for PCT/US2014/022107, entitled: Compositions and Methods for Nucleic Acid Delivery, Date of mailing: Jun. 5, 2014.
Written Opinion PCT/US2014/018284, entitled:Nucleic Acid Particles, Methods and Use Thereof, Date of mailing: Jul. 30, 2014.
Office Action for U.S. Appl. No. 10/280,268, entitled: "Methods of Making Decomposable Thin Films of Polyelectrolytes and Uses Thereofs", Dated: Nov. 2, 2004.
Office Action for U.S. Appl. No. 10/280,268, entitled: "Methods of Making Decomposable Thin Films of Polyelectrolytes and Uses Thereofs", Dated: Jul. 6, 2005.
Office Action for U.S. Appl. No. 10/280,268, entitled: "Methods of Making Decomposable Thin Films of Polyelectrolytes and Uses Thereofs", Dated: Jun. 29, 2006.
Office Action for U.S. Appl. No. 11/459,979, entitled: "Methods of Making Decomposable Thin Films of Polyelectrolytes and Uses Thereof", Dated: Jul. 23, 2010.
Office Action for U.S. Appl. No. 11/459,979, entitled: "Methods of Making Decomposable Thin Films of Polyelectrolytes and Uses Thereof", Dated: Oct. 29, 2009.
Office Action for U.S. Appl. No. 11/815,718, entitled: "Electrochemically Degradable Layer-By-Layer Thin Films", Dated: Mar. 27, 2014.
Office Action for U.S. Appl. No. 11/815,718, entitled: "Electrochemically Degradable Layer-By-Layer Thin Films", Dated: Nov. 27, 2012.
Office Action for U.S. Appl. No. 11/815,718, entitled: "Electrochemically Degradable Layer-By-Layer Thin Films", Dated: Mar. 26, 2012.
Office Action for U.S. Appl. No. 12/139,151, entitled: "Self Assembled Films for Protein and Drug Delivery Applications", Dated: Jun. 11, 2014.
Office Action for U.S. Appl. No. 12/139,151, entitled: "Self Assembled Films for Protein and Drug Delivery Applications", Dated: Jun. 20, 2012.
Office Action for U.S. Appl. No. 12/139,151, entitled: "Self Assembled Films for Protein and Drug Delivery Applications", Dated: Sep. 22, 2011.
Office Action for U.S. Appl. No. 12/542,267, entitled: "Controlled Delivery of Bioactive Agents From Decomposable Films", Dated: Mar. 31, 2014.
Office Action for U.S. Appl. No. 12/542,267, entitled: "Controlled Delivery of Bioactive Agents From Decomposable Films", Dated: Jun. 7, 2013.
Office Action for U.S. Appl. No. 12/542,267, entitled: "Controlled Delivery of Bioactive Agents From Decomposable Films", Dated: Aug. 17, 2012.
Office Action for U.S. Appl. No. 13/115,107, entitled: "Multilayer Coating Compositions, Coated Substrates and Methods Thereof", Dated: Apr. 17, 2014.
Office Action for U.S. Appl. No. 13/459,066, entitled: "Coating Compositions, Methods and Coated Devices ", Dated: Oct. 15, 2014.
Office Action for U.S. Appl. No. 13/459,069 entitled: "Coating Compositions, Methods and Coated Devices", Dated: Oct. 23, 2014.
Office Action for U.S. Appl. No. 13/695,836 entitled: "Drug Delivery Coating and Devices", Dated: Nov. 28, 2014.
Office Action for U.S. Appl. No. 13/869,015 entitled: "Stable Layer-By-Layer Coated Particles", Dated: Nov. 21, 2014.
Office Action for U.S. Appl. No. 14/190,983, "Nucleic Acid Particles, Methods and Use Thereof", date of mailing Jan. 29, 2015.
Office Action for U.S. Appl. No. 13/746,902 entitled: "Compositions and Methods for Coating," Dated: Jan. 2, 2015.

COMPOSITIONS AND METHODS FOR NUCLEIC ACID DELIVERY

CROSS-REFERENCE TO RELATED APPLICATION

This patent application claims priority to and the benefit of, U.S. provisional patent application Ser. No. 61/790,292, filed on Mar. 15, 2013, the entire contents of which are herein incorporated by reference. This patent application also claims priority to and the benefit of, U.S. provisional patent application Ser. No. 61/900,373, filed on Nov. 5, 2013, the entire contents of which are herein incorporated by reference.

BACKGROUND

RNA interference (RNAi) is the process in which small segments of double stranded RNA are used to identify and facilitate the destruction of target mRNA sequences. RNAi holds enormous potential both as a tool in molecular biology as well as a powerful therapeutic agent. Currently however there remain significant questions as to the viability of RNAi in medicine due to the difficulty in delivering the molecule effectively to areas of interest while maintaining its activity and avoiding toxicity. Whether advances in the systemic delivery of siRNA can effectively address these concerns is yet to be seen; technologies for the local administration of RNAi may offer more easily realized opportunities. Local delivery can limit numerous unwanted systemic side effects of therapies and maintains the highest load possible in the targeted area before clearance. Thus, there is a need to develop material systems for localized and sustained delivery of siRNA to tissues.

SUMMARY

The present invention provides, among other things, compositions for delivery of nucleic acid, structures comprising such compositions and methods relating to such compositions.

The present disclosure demonstrates effective delivery of nucleic acid agents, and particularly of certain nucleic acid agents (e.g., siRNA), from LbL films. In light of this provided demonstration that such effective delivery can be achieved, together with other teachings provided herein and/or known in the art, those of ordinary skill in the art will appreciate that various embodiments and variations of the exemplified compositions can now be prepared that will similarly achieve effective nucleic acid delivery.

The present disclosure demonstrates remarkably high loading density of nucleic acid agents into LbL films, and provides compositions including such films containing high density of nucleic acid agents. The present invention specifically provides such high density nucleic acid-loaded LbL films coated on substrates with uneven surfaces (e.g., porous and/or textile substrates), and further demonstrates effective delivery of nucleic acid agents from such films.

Among other things, the present invention provides technologies that achieve localized delivery of nucleic acid agents (e.g., siRNAs); such localized delivery may be particularly useful, for example, in the treatment of certain diseases, disorders or conditions. To mention just a couple of specific such treatment contexts in which provided technologies may be especially useful, in some embodiments, the present invention provides methods and compositions that effectively deliver nucleic acid agents to one or more sites in close proximity to a medical implant (e.g., from a coating on such implant). A wide range of relevant such medical implants is known in the art, including, for example pacemakers, stents, catheters, orthopedic implants, dental implants, etc. In some particular embodiments, localized delivery of nucleic acid agents from LbL films as described herein is useful in the treatment of inflammatory diseases, disorders or conditions, many of which are currently treated with protein therapeutics (e.g., antibodies or peptides), which are typically expensive and often have undesirable systemic side effects.

The present invention specifically demonstrates burst-free and/or sustained release of nucleic acid agents from compositions described herein. In addition, according to certain embodiments, provided compositions exhibit in vitro and/or in vivo biological effectiveness.

DEFINITIONS

In order for the present disclosure to be more readily understood, certain terms are first defined below.

In this application, the use of "or" means "and/or" unless stated otherwise. As used in this application, the term "comprise" and variations of the term, such as "comprising" and "comprises," have their understood meaning in the art of patent drafting and are inclusive rather than exclusive, for example, of additional additives, components, integers or steps. As used in this application, the terms "about" and "approximately" have their art-understood meanings; use of one v. the other does not necessarily imply different scope. Unless otherwise indicated, numerals used in this application, with or without a modifying term such as "about" or "approximately", should be understood to cover normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated reference value unless otherwise stated or otherwise evident from the context (except where such number would exceed 100% of a possible value).

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biodegradable": As used herein, the term "biodegradable" is used to refer to materials that, when introduced into cells, are broken down by cellular machinery (e.g., enzymatic degradation) or by hydrolysis into components that cells can either reuse or dispose of without significant toxic effect(s) on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component and/or into fragments thereof (e.g., into monomeric or submonomeric species). In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

Burst-free release: The term "burst-free release" is used herein to distinguish from "burst-release" which, as is known in the art, refers to release of an agent from a composition with a release profile characterized by a burst in which a significant amount of the agent is released in a relatively short amount of time. Often, such a burst occurs early in a release profile. In some embodiments, a burst is significantly higher than otherwise seen within the release profile. In some embodiments, a burst release is an unsustained release. In some embodiments, a burst-free release is characterized by the absence of a single significant release burst. In some embodiments, a burst-free release is characterized in that the degree of variation in release rate over time does not fluctuate beyond acceptable values understood in the art (e.g., a therapeutic window of a particular agent). In some embodiments, burst-free release is characterized by the absence of any single burst in which more than 20% of the agent is released within a time period that is less than 10% of the total time required to substantially release all of the material. In some embodiments, a burst-free release is characterized by releasing less than about 10%, less than about 20%, less than about 30%, less than about 40%, or less than about 50% of an agent for delivery in the first 1, 2, 5, 10, 12 or 24 hours of releasing.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Nucleic acid": The term "nucleic acid" as used herein, refers to a polymer of nucleotides. In some embodiments, a nucleic acid agent can be or comprise deoxyribonucleic acid (DNA), ribonucleic acid (RNA), peptide nucleic acid (PNA), morpholino nucleic acid, locked nucleic acid (LNA), glycol nucleic acid (GNA) and/or threose nucleic acid (TNA). In some embodiments, nucleic acid agents are or contain DNA; in some embodiments, nucleic acid agents are or contain RNA. In some embodiments, nucleic acid agents include naturally-occurring nucleotides (e.g., adenosine, thymidine, guanosine, cytidine, uridine, deoxyadenosine, deoxythymidine, deoxyguanosine, and deoxycytidine). Alternatively or additionally, in some embodiments, nucleic acid agents include non-naturally-occurring nucleotides including, but not limited to, nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups. In some embodiments, nucleic acid agents include phosphodiester backbone linkages; alternatively or additionally, in some embodiments, nucleic acid agents include one or more non-phosphodiester backbone linkages such as, for example, phosphorothioates and 5'-N-phosphoramidite linkages. In some embodiments, a nucleic acid agent is an oligonucleotide in that it is relatively short (e.g., less that about 5000, 4000, 3000, 2000, 1000, 900, 800, 700, 600, 500, 450, 400, 350, 300, 250, 200, 150, 100, 90, 80, 70, 60, 50, 45, 40, 35, 30, 25, 20, 15, 10 or fewer nucleotides in length).

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polyelectrolyte": The term "polyelectrolyte", as used herein, refers to a polymer which under a particular set of conditions (e.g., physiological conditions) has a net positive or negative charge. In some embodiments, a polyelectrolyte is or comprises a polycation; in some embodiments, a polyelectrolyte is or comprises a polyanion. Polycations have a net positive charge and polyanions have a net negative charge. The net charge of a given polyelectrolyte may depend on the surrounding chemical conditions, e.g., on the pH.

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed). For example, a polypeptide can be a protein. In some embodiments, one or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g, modified sugars such as 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present application.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

BRIEF DESCRIPTION OF THE DRAWING

The Drawing, comprised of several Figures, are for illustration purposes only, not for limitation.

DETAILED DESCRIPTION OF CERTAIN EMBODIMENTS

Figure 1:
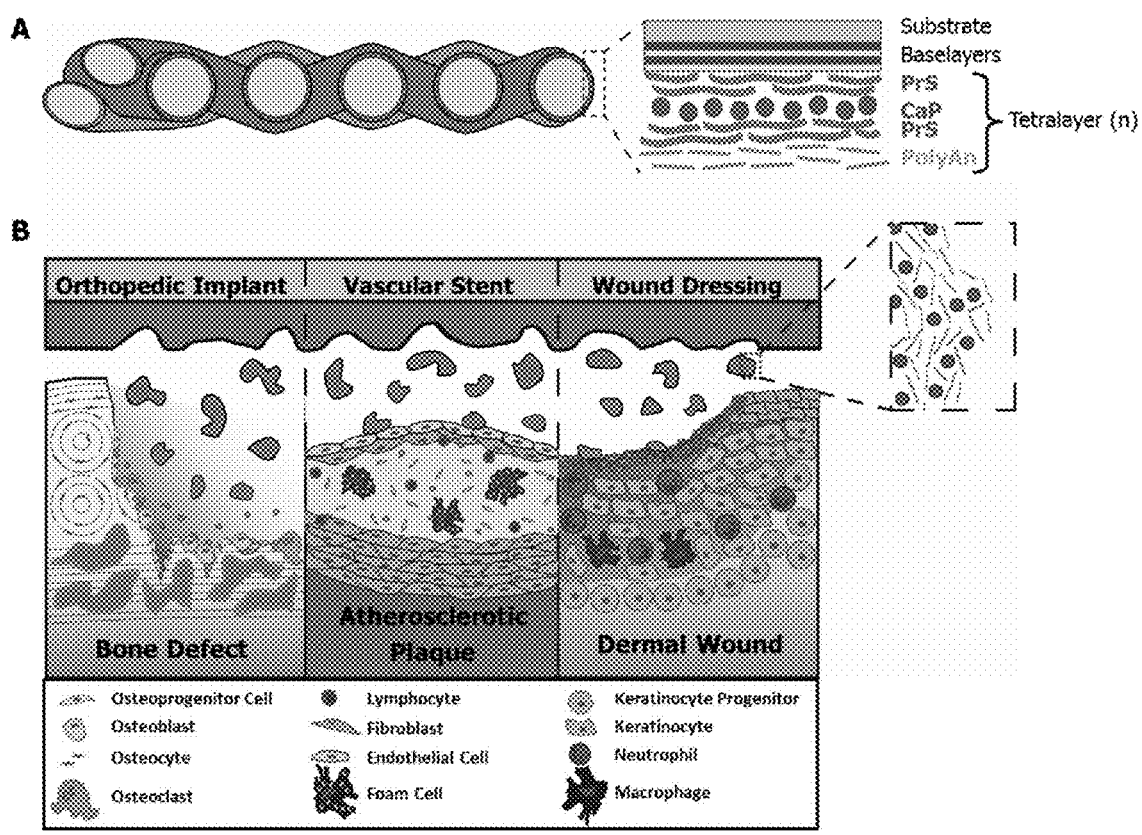
FIG. 1. According to certain embodiments of the present invention, Layer-by-layer (LbL) coating Tegaderm® brand woven nylon would dressing ("Tegaderm®") and potential applications for localized delivery of siRNA. (A) Schematic representation of LbL Film coated Tegaderm®. Shown in the zoomed in portion is a depiction of the Laponite® brand synthetic layered silicate ("Laponite®") containing LbL film architecture. (B) Potential application of LbL films releasing siRNA containing fragments of film into various environments where modulation of cellular responses may provide some therapeutic benefit. Inset illustrates an idealized film mixture released from the coating.

In various embodiments, compositions, structures, and methods in accordance with the present invention are disclosed. In particular, compositions and methods for assembling LbL films associated with one or more nucleic acid agents are disclosed. Provided film compositions, structures, and methods can be used, for example, in the production and/or use of coated substrates, for example to achieve high loading and/or controlled release of desired nucleic acid agents such as siRNA agents.

In some embodiments, provided compositions are characterized by, for example, high loading, substantially burst-free release, sustained release, and/or effective release of nucleic acid agents. By contrast, most or all currently available nucleic acid delivery systems, many of which rely on use of lipid encapsulation, and are prone to low loading efficiencies and "burst effects."

Layer-by-Layer (LbL) Films

Multilayer films described herein can be made of or include one or more LbL films. LbL films may have any of a variety of film architectures (e.g., numbers of layers, thickness of individual layers, identity of materials within films, nature of surface chemistry, presence and/or degree of incorporated materials, etc), as appropriate to the design and application of coated substrates as described herein.

In many embodiments, LbL films are comprised of multilayer units; each unit comprising individual layers. In some embodiments, adjacent layers are associated with one another via non-covalent interactions. Exemplary non-covalent interactions include, but are not limited to ionic interactions, hydrogen bonding interactions, affinity interactions, metal coordination, physical adsorption, host-guest interactions, hydrophobic interactions, pi stacking interactions, van der Waals interactions, magnetic interactions, dipole-dipole interactions and combinations thereof.

LbL films may be comprised of multilayer units in which alternating layers have opposite charges, such as alternating anionic and cationic layers. Alternatively or additionally, LbL films for use in accordance with the present invention may be comprised of (or include one or more) multilayer units in which adjacent layers are associated via non-electrostatic interactions.

According to the present disclosure, LbL films may be comprised of one or more multilayer units. In some embodiments, an LbL film may include multiple copies of a particular individual single unit (e.g., a of a particular bilayer, trilayer, tetralayer, etc unit). In some embodiments, an LbL film may include a plurality of different individual units (e.g., a plurality of distinct bilayer, trilayer, and/or tetralayer units). For example, in some embodiments, multilayer units included in an LbL film for use in accordance with the present invention may differ from one another in number of layers, materials included in layers (e.g., polymers, additives, etc), thickness of layers, modification of materials within layers, etc. In some embodiments, an LbL film utilized in accordance with the present invention is a composite that includes a plurality of bilayer units, a plurality of tetralayer units, or any combination thereof. In some particular embodiments, an LbL film is a composite that includes multiple copies of a particular bilayer unit and multiple copies of a particular tetralayer unit.

In some embodiments, LbL films utilized in accordance with the present invention include a number of multilayer units, which is about or has a lower limit of 2, 3, 4, 5, 6, 7, 8, 9, 10, 15, 20, 25 30, 35, 40, 45, 50, 55, 60, 65, 70, 75, 80, 85, 90, 95, 100, 150, 200, 300, 400 or even 500.

LbL films may have various thickness depending on methods of fabricating and applications. In some embodiments, an LbL film has an average thickness in a range of about 1 nm and about 100 μm. In some embodiments, an LbL film has an average thickness in a range of about 1 μm and about 50 μm. In some embodiments, an LbL film has an average thickness in a range of about 2 μm and about 5 μm. In some embodiments, the average thickness of an LbL film is or more than about 1 nm, about 100 nm, about 500 nm, about 1 μm, about 2 μm, about 3 lam, about 4 μm, about 5 μm, about 10 μm, bout 20 μm, about 50 μm, about 100 μm. In some embodiments, an LbL film has an average thickness in a range of any two values above.

In some embodiments, layers of LbL films can contain or consist of a silica material such as silicate. To give an example, Laponite® silicate clay (Lap) can be used in a multilayer film as demonstrated in Examples below.

Individual layers of LbL films can contain, be comprised of, or consist of one or more polymeric materials. In some embodiments, a polymer is degradable or non-degradable. In some embodiments, a polymer is natural or synthetic. In some embodiments, a polymer is a polyelectrolyte. In some embodiments, a polymer is a polypeptide and/or a nucleic acid. For example, a nucleic acid agent for delivery in accordance with various embodiments can serve as a layer in LbL films.

LbL films can be decomposable. In many embodiments, LbL film layers are comprised of or consisted of one or more degradable materials, such as degradable polymers and/or polyelectrolytes. In some embodiments, decomposition of LbL films is characterized by substantially sequential degradation of at least a portion of each layer that makes up an LbL film. Degradation may, for example, be at least partially hydrolytic, at least partially enzymatic, at least partially thermal, and/or at least partially photolytic. In some embodiments, materials included in degradable LbL films, and also their breakdown products, may be biocompatible, so that LbL films including them are amenable to use in vivo.

Degradable materials (e.g. degradable polymers and/or polyelectrolytes) useful in LbL films disclosed herein, include but are not limited to materials that are hydrolytically, enzymatically, thermally, and/or photolytically degradable, as well as materials that are or become degradable through application of pressure waves (e.g., ultrasonic waves).

Hydrolytically degradable polymers known in the art include for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. Of course, co-polymers, mixtures, and adducts of these polymers may also be employed.

Anionic polyelectrolytes may be degradable polymers with anionic groups distributed along the polymer backbone. Anionic groups, which may include carboxylate, sulfonate, sulphate, phosphate, nitrate, or other negatively charged or ionizable groupings, may be disposed upon groups pendant from the backbone or may be incorporated in the backbone itself. Cationic polyelectrolytes may be degradable polymers with cationic groups distributed along the polymer backbone. Cationic groups, which may include protonated amine, quaternary ammonium or phosphonium-derived functions or other positively charged or ionizable groups, may be disposed in side groups pendant from the backbone, may be attached to the backbone directly, or can be incorporated in the backbone itself.

For example, a range of hydrolytically degradable amine-containing polyesters bearing cationic side chains have been developed. Examples of these polyesters include poly(L-lactide-co-L-lysine), poly(serine ester), poly(4-hydroxy-L-proline ester), and poly[α-(4-aminobutyl)-L-glycolic acid].

In addition, poly(β-amino ester)s, prepared from the conjugate addition of primary or secondary amines to diacrylates, are suitable for use. Typically, poly(β-amino ester)s have one or more tertiary amines in the backbone of the polymer, preferably one or two per repeating backbone unit. Alternatively, a co-polymer may be used in which one of the components is a poly(β-amino ester). Poly(β-amino ester)s are described in U.S. Pat. Nos. 6,998,115 and 7,427,394, entitled "Biodegradable poly(β-amino esters) and uses thereof" and Lynn et al., *J. Am. Chem. Soc.* 122:10761-10768, 2000, the entire contents of both of which are incorporated herein by reference.

In some embodiments, a polymer utilized in the production of LbL film(s) can have a formula below:

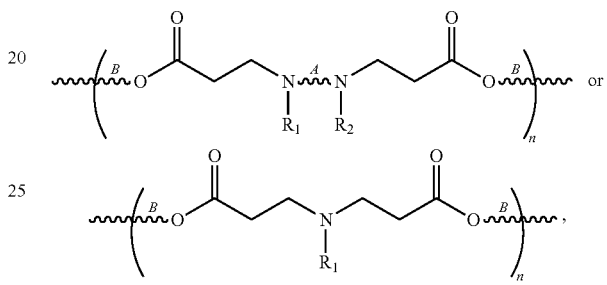

where A and B are linkers which may be any substituted or unsubstituted, branched or unbranched chain of carbon atoms or heteroatoms. The molecular weights of the polymers may range from 1000 g/mol to 20,000 g/mol, preferably from 5000 g/mol to 15,000 g/mol. In certain embodiments, B is an alkyl chain of one to twelve carbons atoms. In other embodiments, B is a heteroaliphatic chain containing a total of one to twelve carbon atoms and heteroatoms. The groups $R_1$ and $R_2$ may be any of a wide variety of substituents. In certain embodiments, $R_1$ and $R_2$ may contain primary amines, secondary amines, tertiary amines, hydroxyl groups, and alkoxy groups. In certain embodiments, the polymers are amine-terminated; and in other embodiments, the polymers are acrylated terminated. In some embodiments, the groups $R_1$ and/or $R_2$ form cyclic structures with the linker A.

Exemplary poly(β-amino esters) include

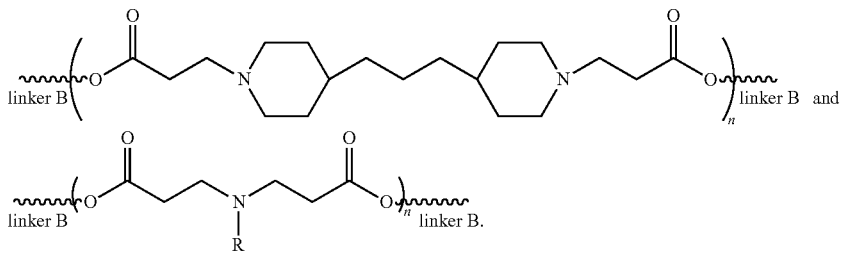

Exemplary R groups include hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups.

Exemplary linker groups B includes carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. The polymer may include, for example, between 5 and 10,000 repeat units.

In some embodiments, a poly(β-amino ester)s are selected from the group consisting of In some embodiments, polyanionic and/or polycationic layers may include a non-degradable and/or slowly hydrolytically degradable polyelectrolytes. Any non-degradable polyelectrolyte can be used. Exemplary non-degradable polyelectrolytes that could be used in thin films include poly(styrene sulfonate) (SPS), poly(acrylic acid) (PAA), linear poly(ethylene imine) (LPEI), poly(diallyldimethyl ammonium chloride) (PDAC), and poly(allylamine hydrochloride) (PAH).

In some embodiments, the present invention utilizes polymers that are found in nature and/or represent structural variations or modifications of such polymers that are found in nature. In some embodiments, polymers are charged polysaccharides such as, for example sodium alginate, chitosan, agar, agarose, and carragenaan. In some embodiments, polysaccharides include glycosaminoglycans such as heparin, chondroitin, dermatan, hyaluronic acid, etc. Those of ordinary skill in the art will appreciate that terminology used to refer to particular glycosaminoglycans sometimes also is used to refer to a sulfate form of the glycosaminoglycan, e.g., heparin sulfate, chondroitin sulfate, etc. It is intended that such sulfate forms are included among a list of exemplary polymers used in accordance with the present invention.

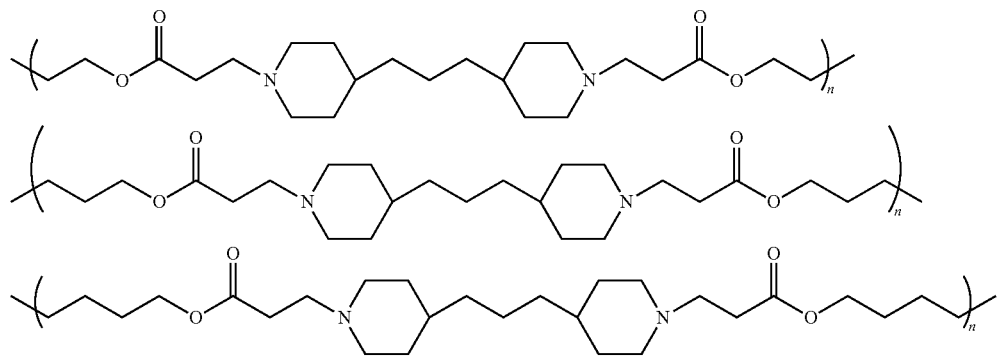

40 derivatives thereof, and combinations thereof.

Alternatively or additionally, zwitterionic polyelectrolytes may be used. Such polyelectrolytes may have both anionic and cationic groups incorporated into the backbone or covalently attached to the backbone as part of a pendant group. Such polymers may be neutrally charged at one pH, positively charged at another pH, and negatively charged at a third pH. For example, an LbL film may be constructed by LbL deposition using dip coating in solutions of a first pH at which one layer is anionic and a second layer is cationic. If such an LbL film is put into a solution having a second different pH, then the first layer may be rendered cationic while the second layer is rendered anionic, thereby changing the charges on those layers.

The composition of degradable polyeletrolyte layers can be fine-tuned to adjust the degradation rate of each layer within the film, which is believe to impact the release rate of drugs. For example, the degradation rate of hydrolytically degradable polyelectrolyte layers can be decreased by associating hydrophobic polymers such as hydrocarbons and lipids with one or more of the layers. Alternatively, polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions.

In some embodiments, an LbL film comprises at least one layer that degrades and at least one layer that delaminates. In some embodiments, a layer that degrades in adjacent a layer that delaminates. In some embodiments, an LbL film comprises at least one polycationic layer that degrades and at least one polyanionic layer that delaminates sequentially; in some embodiments, an LbL film comprises at least one polyanionic layer that degrades and at least one polycationic layer that delaminates.

In some embodiments, one or more agents is incorporated into one or more layers of an LbL film. In some embodiments layer materials and their degradation and/or delamination characteristics are selected to achieve a desired release profile for one or more agents incorporated within the film. In some embodiments, agents are gradually, or otherwise controllably, released from an LbL film.

In accordance with the present invention, LbL films may be exposed to a liquid medium (e.g., intracellular fluid, interstitial fluid, blood, intravitreal fluid, intraocular fluid, gastric fluids, etc.). In some embodiments, layers of the LbL films degrade and/or delaminate in such a liquid medium. In some embodiments, such degradation and/or delamination achieves delivery of one or more agents, for example according to a predetermined release profile.

In light of this provided demonstration that effective delivery of nucleic acids can be achieved using LbL films, those of ordinary skill in the art will appreciate that various embodiments and variations of the exemplified compositions can now be prepared that will similarly achieve effective nucleic acid delivery. Certain characteristics of compositions described herein may be modulated to achieve desired functionalities for different applications.

In some embodiments, loading capacity may be modulated, for example, by changing the number of multilayer units that make up the film, the type of degradable polymers used, the type of polyelectrolytes used, and/or concentrations of solutions of agents used during construction of LbL films.

Additionally or alternatively, other conditions for example prior to or during deposition can be adjusted as those of ordinary skills in the art would appreciate and understand. In some embodiments, suitable pH values can include 2, 3, 4, 5, 6, 7, 8, 9, 10. In some embodiments, a suitable salt concentration is less than 5 M, 1 M, 0.5 M, 0.1 M, and 0.01 M. In some embodiments, suitable buffers include sodium acetate, Tris HCl, HEPES, Glycine or combination thereof.

Similarly, in some embodiments, release kinetics (both rate of release and release timescale of an agent) may be modulated by changing any or a combination of aforementioned factors.

Agents for Delivery

In some embodiments, the present invention provides compositions that comprise one or more nucleic acid agents for delivery. In some embodiments, such compositions may also include one or more other agents.

In some embodiments, agents may be released from LbL films. In some embodiments, an agent for delivery is released when one or more layers of a LbL film are decomposed and/or delaminated. Additionally or alternatively, in some embodiments, an agent may be released by diffusion.

In some embodiments, one or more agents are associated independently with a substrate, an LbL film coating the substrate, or both.

In some embodiments, an agent can be associated with one or more individual layers of an LbL film, affording the opportunity for exquisite control of loading and/or release from the film. In some embodiments, an agent is incorporated into an LbL film by serving as a layer. For example, a polypeptide or a nucleic acid agent can serve as a layer and also as an agent for delivery.

In theory, any agents including, for example, therapeutic agents (e.g. antibiotics, NSAIDs, glaucoma medications, angiogenesis inhibitors, neuroprotective agents), cytotoxic agents, diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be associated with the LbL film disclosed herein to be released.

In some embodiments, compositions described herein include one or more agents. Exemplary agents include, but are not limited to, small molecules (e.g. cytotoxic agents), nucleic acid (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof.

Nucleic Acid Agents

In some embodiments, a nucleic acid agent is or comprises a therapeutic agent. In some embodiments, a nucleic acid agent is or comprises a diagnostic agent. In some embodiments, a nucleic acid agent is or comprises a prophylactic agent.

It would be appreciate by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or comprise deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or comprises at least one protein-coding element. In some embodiments, a nucleic acid has a nucleotide sequence that is or comprises at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiments, a nucleic acid agent is or comprises an oligonucleotide. In some embodiments, a nucleic acid agent is or comprises an antisense oligonucleotide. Nucleic acid agents may include a chemical modification at the individual nucleotide level or at the oligonucleotide backbone level, or it may have no modifications.

In some embodiments, provided compositions comprise two or more different nucleic acid agents. In some embodiments, compositions and, in particular, LbL films described herein comprise multiple, for example, 2, 3, 5, 10, 15, 20, 50 or even 100 nucleic acid agents (e.g., siRNA agents). Incorporation of such nucleic acid agents can be conducted using a composition termed as a "cocktail" that contains two or more nucleic acid agents. This can allow loading of nucleic acid agents in stoichiometrically pre-determined ratios for highly-tuned control. Such attributes and embodiments can be particularly useful for combination therapies.

At least one or each nucleic acid agent used in accordance with many embodiments is characterized by its high loading in LbL films. In some embodiments, a nucleic acid agent (e.g., siRNA agent) has a loading density of at least about 1 μg/cm$^2$, at least about 2 μg/cm$^2$, at least about 5 μg/cm$^2$, at least about 8 μg/cm$^2$, at least about 10 μg/cm$^2$, at least about 12 μg/cm$^2$, at least about 15 μg/cm$^2$, at least about 18 μg/cm$^2$, at least about 20 μg/cm$^2$, at least about 25 μg/cm$^2$, at least about 30 μg/cm$^2$, at least about 50 μg/cm$^2$, or at least about 100 μg/cm$^2$.

In accordance with many embodiments of the present invention, a nucleic acid agent can be an siRNA agent. Among other things, the present invention demonstrates surprisingly high loading of siRNA agents into LbL compositions. Moreover, the present invention surprisingly demonstrates effective release of active siRNA agents from such LbL compositions. Still further, the present invention surprisingly demonstrates that siRNA agents can be maintained in stable (i.e., non-denatured and/or non-degraded forms) in LbL compositions. Having established through these demonstrations that it is possible to achieve high loading and/or effective delivery of siRNA agents, the present disclosure surprisingly establishes that active nucleic acid agents can be loaded into and/or effectively delivered from LbL agents as described herein.

Short interfering RNA (siRNA) comprises an RNA duplex that is approximately 19 basepairs long and optionally further comprises one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to comprise sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase 1B (PTP1B).

Other Agents

In addition to one or more nucleic acid agents, in some embodiments, provided compositions comprise one or more other agents, for example, therapeutic and/or diagnostic agents.

In some embodiments, a therapeutic agent is or comprises a small molecule and/or organic compound with pharmaceutical activity. In some embodiments, a therapeutic agent is a clinically-used drug. In some embodiments, a therapeutic agent is or comprises an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

In some embodiments, a therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof.

In some embodiments, a therapeutic agent may be or comprise an anti-inflammatory agent. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

Those skilled in the art will recognize that this is an exemplary, not comprehensive, list of agents that can be released using compositions and methods in accordance with the present disclosure. In addition to a therapeutic agent or alternatively, various other agents may be associated with a coated substrate in accordance with the present disclosure.

Agents Useful for Wound Healing

Some embodiments of the present invention can be particularly useful for wound healing. In some embodiments, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

Exemplary agents useful for wound healing can include, but are not limited to, wound-healing-promoting or scar-reducing agents for wound treatment modalities now known in the art or later-developed; exemplary factors, agents or modalities including natural or synthetic growth factors, cytokines, or modulators thereof to promote wound healing, wound healing promoting bioengineered matrix, dressings bandages, and the like. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), Colla-GUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox® lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that the agents useful for wound healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

Substrates

The present invention provides compositions comprising an LbL film, optionally including one or more agents, disposed upon a substrate. Any of a variety of materials or entities may be utilized as a substrate in accordance with the present invention.

In some embodiment, a substrate have a porous or textile surface. In some embodiments, a substrate is or contain particles such as nanoparticles and micropartilces.

A substrate can be or comprise a medical device. Some embodiments of the present disclosure comprise various medical devices, such as sutures, bandages, clamps, valves, intracorporeal or extracorporeal devices (e.g., catheters), stents, vascular grafts, anastomotic devices, aneurysm repair devices, embolic devices, and implantable devices/scaffolds (e.g., orthopedic and dental implants) and the like. LbL films can be used in accordance with the present disclosure to coat such medical devices.

Dressings and Matrices

In some aspects, one or more nucleic acid agents optionally together with one or more other agents such as therapeutic agents are provided in the form of a dressing or matrix that is useful for would healing.

In some embodiments, dressings or matrices are absorptives. Suitable absorptives may include, for example, absorptive dressings, which can provide, for example, a semi-adherent quality or a non-adherent layer, combined with highly absorptive layers of fibers, such as for example, cellulose, cotton or rayon. Alternatively, absorptives may be used as a primary or secondary dressing.

In some embodiments, dressings or matrices are biological and/or biosynthetics. Suitable biological dressings or biosynthetic dressings may include, for example, gels, solutions or semi-permeable sheets derived from a natural source. In certain embodiments, a gel or solution is applied to the treatment site and covered with a dressing for barrier protection. In certain embodiments, a sheet is placed in situ which may act as membrane, remaining in place after a single application.

In some embodiments, dressings or matrices are composites. Suitable composite dressings may include, for example, dressings that combine physically distinct components into a single product to provide multiple functions, such as, for example, a bacterial barrier, absorption and adhesion. In certain embodiment, composite dressings are comprised of, for example, multiple layers and incorporate a semi- or non-adherent pad. In certain embodiment, the composite may also include for example, an adhesive border of non-woven fabric tape or transparent film. In certain embodiments, a composite dressing may function as for example, either a primary or a secondary dressing and in yet another embodiment, the dressing may be used in combination with topical pharmaceutical composition.

In some embodiments, dressings or matrices are elastic bandages. Suitable elastic bandages may include, for example, dressings that stretch and conform to the body contours. In certain embodiments, the fabric composition may include for example, cotton, polyester, rayon or nylon. In certain other embodiments, the elastic bandage may for example, provide absorption as a second layer or dressing, to hold a cover in place, to apply pressure or to cushion a treatment site.

In addition or alternatively, dressings or matrices can be transparent films. Suitable transparent film dressings may include polymer membranes of varying thickness coated on one side with an adhesive. In certain embodiments, transparent films are impermeable to liquid, water and bacteria but permeable to moisture vapor and atmospheric gases. In certain embodiments, the transparency allows visualization of the treatment site.

Methods and Uses

There are several advantages to LbL assembly techniques used to coat a substrate in accordance with the present disclosure, including mild aqueous processing conditions (which may allow preservation of biomolecule function); nanometer-scale conformal coating of surfaces; and the flexibility to coat objects of any size, shape or surface chemistry, leading to versatility in design options. According to the present disclosure, one or more LbL films can be assembled and/or deposited on a substrate to provide a coated device. In many embodiments, a coated device having one or more agents for delivery associated with it, such that decomposition of layers of LbL films results in release of the agents.

In various embodiments, LbL films can be different in film materials (e.g., polymers), film architecture (e.g., bilayers, tetralayer, etc.), film thickness, and/or agent association depending on methods and/or uses. In many embodiments, compositions (e.g., a coated device) in accordance with the present disclosure are for medical use. In some embodiments, compositions and methods described herein are particularly useful for nucleic acid delivery.

It will be appreciated that an inherently charged surface of a substrate can facilitate LbL assembly of an LbL film on the substrate. In addition, a range of methods are known in the art that can be used to charge the surface of a substrate, including but not limited to plasma processing, corona processing, flame processing, and chemical processing, e.g., etching, micro-contact printing, and chemical modification.

In some embodiments, substrate can be coated with a base layer. Additionally or alternatively, substrates can be primed with specific polyelectrolyte bilayers such as, but not limited to, LPEI/SPS, PDAC/SPS, PAH/SPS, LPEI/PAA, PDAC/PAA, and PAH/PAA bilayers, that form readily on weakly charged surfaces and occasionally on neutral surfaces. Exemplary polymers can be used as a primer layer include poly(styrene sulfonate) and poly(acrylic acid) and a polymer selected from linear poly(ethylene imine), poly(diallyl dimethyl ammonium chloride), and poly(allylamine hydrochloride). It will be appreciated that primer layers provide a uniform surface layer for further LbL assembly and are therefore particularly well suited to applications that require the deposition of a uniform thin film on a substrate that includes a range of materials on its surface, e.g., an implant or a complex tissue engineering construct.

In some embodiments, assembly of an LbL film may involve a series of dip coating steps in which a substrate is dipped in alternating solutions. In some embodiments, LbL assembly of a film may involve mixing, washing or incubation steps to facilitate interactions of layers, in particular, for non-electrostatic interactions. Additionally or alternatively, it will be appreciated that LbL deposition may also be achieved by spray coating, dip coating, brush coating, roll coating, spin casting, or combinations of any of these techniques. In some embodiments, spray coating is performed under vacuum. In some embodiments, spray coating is performed under vacuum of about 10 psi, 20 psi, 50 psi, 100 psi, 200 psi or 500 psi. In some embodiments, spray coating is performed under vacuum in a range of any two values above.

In some embodiments, provided compositions and/or structures (e.g., coated medical devices) are administered to (e.g., contacted with and/or implanted within) a subject in need thereof. Subject can be a human. In some such embodiments, the subject is suffering from or susceptible to one or more disorders. In some embodiments, the subject is undergoing or has undergone a surgical procedure.

EXEMPLIFICATION

Example 1

This Example demonstrates an LbL nano-layered coating for the delivery of siRNA that is capable of sustaining significant knockdown in multiple cell lines for over one week in vitro.

This film requires no externally delivered transfection vectors or mechanical transfection techniques (e.g. electroporation) to achieve these results. This film was applied to a commercially available woven nylon bandage for testing and showed minimal impact on the viability of cells exposed to it. A schematic of the application of such an LbL film is presented in FIG. 1A where the coating is shown applied to a generic woven substrate. FIG. 1B illustrates a range of potential applications for such a coating in multiple different localized delivery applications.

Materials: siRNA for GFP and siControl were received as a gift from Sanofi-Aventis. Alexafluor 488-labeled siRNA was purchased from Qiagen (Valencia, Calif.). Linear poly (ethyleneimine) (LPEI, MW=25 kDa) and dextran sulfate (DS, MW=500 kDa or 9 kDa) were purchased from Polysciences (Warrington, Pa.). Phosphate buffered saline solution (PBS, 10×), Advanced-MEM, fetal bovine serum, antibiotic-antimycotic solution and 200 mM L-glutamine solution were purchased from Invitrogen (Carlsbad, Calif.). GFP expressing NIH-3T3 cells were purchased from Cell Biolabs (San Diego, Calif.). NIH-3T3, MDA-MB-435, and M4A4 cells were purchased from ATCC (Manassas Va.). Tegaderm® was purchased from Cardinal Health (Newark, N.J.).

The Formation of siRNA Loaded Calcium Phosphate Nanoparticles

Calcium phosphate (CaP) nanoparticles containing siRNA were synthesized by rapid precipitation of $CaCl_2$ and $NH_3PO_4$ in the presence of siRNA. $NH_3PO_4$. (3.74 mM) and $CaCl_2$ (6.25 mM) working solutions were prepared in nuclease free water pH 8.5 and filtered using a 0.2 μm syringe filter. To prepare 3 mL of CaP nanoparticles, a dipping solution containing 20 μg/mL siRNA and 200 μL of $NH_3PO_4$ was added to 60 μg of siRNA in 100 μL nuclease free water. 200 μL of the $CaCl_2$ solution was then added with vigorous mixing. After approximately 30 seconds 2.5 mL of pH 8.5 nuclease free water was then added to dilute the particles to the dipping concentration. The diameter and zeta potential of the formed nanoparticle were measured both prior to and after film assembly using a ZetaPALS dynamic light scattering and zeta potential analyzer. The CaP siRNA particles were prepared just prior to LbL film construction.

Fabrication of LbL Films

Film assembly was performed using an HMS series Carl-Zeiss programmable slide stainer. Substrates to be coated were first cleaned sequentially with methanol, ethanol, isopropanol and water and then dried under filtered nitrogen. These substrates were plasma cleaned for 5 minutes on the high RF setting and then immediately placed in a 2 mg/mL solution of LPEI and allowed to adsorb the material for at least 30 minutes prior to use. After this initial coating, substrates were then placed into specially designed holders for the programmable slide stainer to move between dipping baths. A generic bilayer LbL assembly protocol consists of first dipping the substrate into a polycation solution for some specified time, then moving that substrate through two wash steps where excess polymer is allowed to desorb from the surface. The washed substrate is then placed in a polyanion solution and allowed to adsorb polymer. After adsorption of the polyanion the substrate is then washed two more times to remove any excess polymer. This process can then be repeated for multiple depositions of the bilayer architecture.

All films were assembled on top of 10 baselayers of (LPEI/DS) to ensure a conformal charged coating of the substrate for siRNA film deposition. Assembly of baselayers was carried out in 100 mM sodium acetate solution at pH 5.0. All solutions were filtered using a 0.2 μm membrane syringe filter prior to use. Polymer solutions used were prepared at a 2 mg/mL concentration and all CaP nanoparticle solutions contained approximately 20 μg/mL concentration of siRNA. Polymer deposition steps were done for 10 minutes and CaP nanoparticle deposition steps were done for 45 minutes. All deposition steps were followed with two 1 minute washes in pH adjusted nuclease free water. All solutions for siRNA containing films were prepared in pH 9.0 nuclease free water.

Film Thickness and Surface Characterization

The thickness of the LbL films were assessed for films assembled on silicon and glass substrates using both spectroscopic ellipsometry (XLS-100 Spectroscopic Ellipsometer J.A. Woollam Co., Inc) and profilometry (Dektak 150 Profilometer). Ellipsometric measurements were performed on LbL films assembled on silicon substrates. Films were dried under filtered nitrogen prior to measurement. Measurements were performed at room temperature with a 70° incidence angle. The acquired spectra were then fit with a Cauchy dispersion model to obtain an estimated thickness for the film. For measurement of film thickness by profilometry, films were built on either silicon or glass and scored by a razor then tracked over. Step height from the untouched film to the bottom of the score was measured in six different locations on each sample to obtain an average thickness.

Atomic force microscopy (AFM) was performed using a Dimension 3100 AFM with Nanoscope 5 controller (Veeco Metrology) in tapping mode. Film areas of 25 μm by 25 lam were examined for each film after 5, 15 and 25 architecture depositions. Nanoscope analysis v1.10 software was used to calculate the root mean squared roughness for films.

Quantification of siRNA Loading into LbL Assembly

Incorporation of siRNA within the LbL film assemblies were quantified after 5, 10, 15 and 25 architecture repeats. To quantify the amount of siRNA within the film a one square centimeter sample of a film coated substrate was placed into 500 μL of 1 M NaCl solution prepared from nuclease free water. The sample was then subjected to vigorous agitation for 30 minutes to completely remove the film from the surface. The substrate was then removed from the salt solution, washed with deionized water and dried under filtered nitrogen. These substrates were evaluated by SEM to check that the entire film had been removed from the surface. Quantification of siRNA was performed using Oligreen dsDNA reagent (Invitrogen) as per the manufacturer's instructions. The degradation solution containing the released film was diluted 1:20 into nuclease free water to reduce salt concentration to within the tolerance range of the assay. 25 μL of degradation sample was then added to 100 μL of prepared Oligreen reagent (diluted 1:200 in TE buffer of reagent in kit) in a fluoroblock (BD) 96-well plate. Samples were then read with a fluorescent plate reader with 490/520 Ex/Em wavelengths. siRNA standards were prepared using similar salt concentrations to that in the diluted degradation samples.

Degradation Studies and Release Characterization

Experiments for the quantification of film degradation were carried out in cell conditioned media. To assist in the visualization of the degradation of the film, AlexaFluor 488-labeled siRNA was used. Cell conditioned media was prepared from NIH-3T3 cells grown to confluence. NIH-3T3s were seeded into a 24-well plates (50,000 cells/well) and cultured in Advanced-MEM (Invitrogen) media containing 5% FBS, 1% antibiotic-antimycotic solution, and 2 mM L-glutamine. Cells grew to confluence within approximately 1 day after seeding. Media was removed from wells after 72 hours in contact with the cells. This media was filtered using a 0.2 μm syringe filter to remove cellular debris. This filtered media was then placed directly onto of the films to be degraded. Degradations were carried out at 37° C. with the entire degradation media exchanged daily. Unlabeled siRNA served as a blank non-fluorescent control. A standard curve of the fluorescently labeled siRNA was used to interpret the concentration of siRNA within the release media. SEM analysis of all samples was done in JEOL 6700F scanning electron microscope. Confocal imaging of degrading samples was performed on a Zeiss LSM 510 Confocal Laser Scanning Microscope.

Characterization of In Vitro Knockdown

GFP knockdown was characterized by flow cytometry measurements of mean cell fluorescence in NIH-3T3, MDA-MB-435, and M4A4 cells that constitutively expressed GFP. 5,000 cells per well were seeded in a 48 well plate in 600 μL of cell growth media and allowed to incubate for 24 hours. Films coated substrates were cut into 0.5×0.5 cm (0.25 cm$^2$ total area) squares and placed into the wells with the cells. After 3, 5, or 7 days of exposure to the film coated substrates cells were trypsinized and mean cell fluorescence was determined by flow cytometry, using a BD FACSCalibur flow cytometer.

Preservation of siRNA Knockdown During Release

Films were created using GFP specific siRNA. GFP expressing NIH-3T3s were seeded as previously described. Films were pre-degraded in cell conditioned media for 24, 72 or 120 hours and then placed in culture with cells. Cells were exposed to films for 72 hours. Mean cell fluorescence was measured using flow cytometry. Films containing negative control siRNA were used for quantification of relative cell fluorescence.

In Vitro Transfection with Fluorescently Labeled siRNA

Transfection of NIH-3T3s was monitored using fluorescently labeled siRNA. Similar to knockdown experiments films containing the labeled siRNA were built on Tegaderm® samples and placed in culture with NIH-3T3 cells grown on coverslips in cell growth media. Cells were exposed to films for up to 1 week in vitro with media being changed every two days. At day 3, 5, and 7 samples were taken for microscope analysis of transfection. Cells were fixed in formalin diluted in PBS and counterstained with DAPI nuclear stain.

siRNA Thin Film Assembly:

Four LbL film architectures containing siRNA loaded calcium phosphate nanoparticles are investigated. CaP nanoparticles were chosen as they have been shown to remain intact after incorporation into LbL assemblies. CaP nanoparticles dissociate upon maturation of the endosome when the pH falls below approximately 6.8-6.6; once within the endosomal compartment, the dissociation of CaP causes osmotic pressure increases and the endosomal rupture and release of the packaged siRNA into the cytosol. The films were constructed of different architectures consisting of bilayer or tetralayer combinations of polyelectrolyte materials. Protamine sulfate (PrS), a naturally derived protein isolated from salmon sperm, was chosen for the polycation for all films in this paper, as it has an isoelectric point around pH 12 and has been shown to complex nucleic acid agents very effectively. PrS consists largely of arginine and has been shown to bind DNA and siRNA and protect them from nuclease degradation for multiple days when exposed to serum nucleases. Three polyanions were used in combination with the CaP nanoparticles and PrS in LbL assemblies: (1) low molecular weight (9 kDa) dextran sulfate ($DS_L$), (2) high molecular weight (500 kDa) dextran sulfate ($DS_H$), and (3) Laponite® silicate clay (Lap). All components are either readily degraded by proteases or other enzymes in the body, or are native biomolecules that can be readily resorbed or cleared from the body.

The four films tested in this investigation were: (1) (PrS/CaP nanoparticle) bilayer, (2) (PrS/CaP nanoparticle/PrS/$DS_L$) tetralayer, (3) (PrS/CaP nanoparticle/PrS/$DS_H$) tetralayer, and (4) (PrS/CaP nanoparticle/PrS/Lap) tetralayer. These four different films gave very different results in their respective rates of film growth, siRNA incorporation, and the level of knockdown observed.

CaP nanoparticles were analyzed using a ZetaPALS dynamic light scattering and zeta potential analyzer before and after film construction to evaluate any change in particle characteristics during the film building process. Prior to film construction the average nanoparticle diameter was approximately 217 nm and had a negative zeta potential of nearly −30 mV. After the generation of the LbL multilayer film (25 bi- or tetralayers), the particle size of the remaining CaP particles in solution was 199 nm and the particles exhibited a similar zeta potential to nanoparticles prior to dipping (−28 mV).

Film growth was measured using both profilometry and ellipsometry on films built on silicon substrates. The growth curve for each architecture is plotted in FIG. 2A. The thinnest film, (PrS/CaP), grew linearly (as plotted $R^2=0.97$) with an average growth rate of approximately 4 nm per layer, reaching 103 nm±18.5 nm after 25 layers. Even after 25 layers this film did not approach a thickness equal to the average diameter of the particles being incorporated, which suggests that less than a complete monolayer of coverage was obtained during assembly. AFM imaging of the surface showed many small particle-sized features that became denser with increasing number of bilayers. The roughness of this film was also seen to increase during growth from approximately 9.6 nm at 5 bilayers to 16.6 nm at 25 bilayers.

The (PrS/CaP/PrS/$DS_L$) film growth was not truly linear over the 25 layers investigated (as suggested by the plotted $R^2=0.91$ for a linear fit). For the first 15 layers the film grew at approximately 6.8 nm per layer which increased significantly in to nearly 25 nm per layer from layers 15 to 25. Although it is unclear from the growth rate data alone, this kind of increase in film thickness is a characteristic of inter-diffusion taking place during film construction. After 25 tetralayers, the (PrS/CaP/PrS/DS$_L$) was the second thickest film tested at 380 nm±30.2 nm and had a surface roughness of approximately 35 nm. Both the Lap and DS$_H$ containing films exhibited near linear growth over the 25 architecture repeats (as plotted R$^2$=0.98, and 0.95, respectively). The (PrS/CaP/PrS/DS$_H$) grew by nearly 10.5 nm per tetralayer and reached a thickness of 257 nm±24.5 at 25 tetralayers, while the (PrS/CaP/PrS/Lap) film grew by approximately 31 nm per layer reaching 633 nm±72 nm at 25 layers. The roughness of these two films was similar (DS$_H$=18.3 nm, Lap=21.6 nm) after 25 layers.

Figure 2:
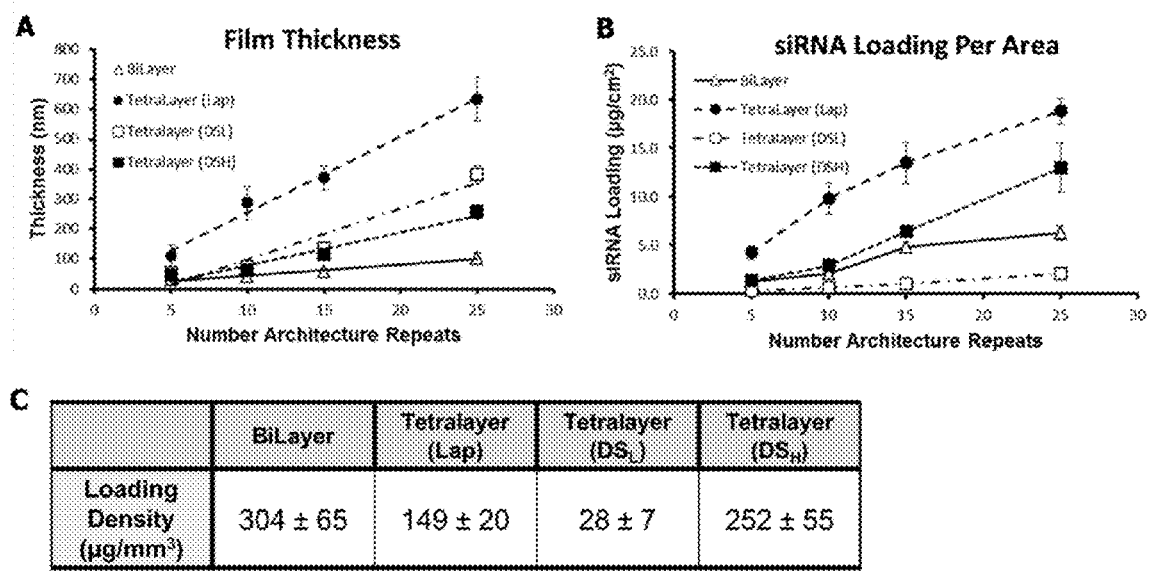
FIG. 2. LbL film growth and siRNA incorporation in accordance with certain embodiments of the present invention. (A) Plot of film thickness versus the number of film architecture repeats for all four film architectures deposited on flat silicon substrates. The data points represent average measurements taken by both profilometry and elipsometry, error bars represent 95% confidence interval. (B) Plot of total siRNA loading per film area of all four tested films measured using oligreen dsDNA assay of fully degraded samples. (C) siRNA loading density ($\mu g/mm^3$) for film architectures tested at 25 architecture repeats.

The amount of siRNA incorporated per coated area within the different film architectures varied significantly with the choice of polyanion (FIG. 2B). After 25 layers the (PrS/CaP/PrS/DS$_L$) film had incorporated the least amount of siRNA, only 2.1±0.6 µg/cm$^2$, while the (PrS/CaP/PrS/Lap) film contained nearly 10 times that amount (18.9±1.4 µg/cm$^2$). It is interesting to note that increased film thickness did not correlate with increased siRNA loading, as the DS$_L$ containing film was nearly 1.5 times thicker than the DS$_H$ film at 25 tetralayers and yet held less than one-sixth the amount of siRNA (12.9±2.6 µg/cm$^2$). The (PrS/CaP) film incorporated 6.3±0.7 µg/cm$^2$ after 25 layers, approximately one-third as much as the Lap containing tetralayer film, however it was one-sixth as thick. The average siRNA density for each film after 25 architecture repeats is shown in FIG. 2C.

Figure 3:
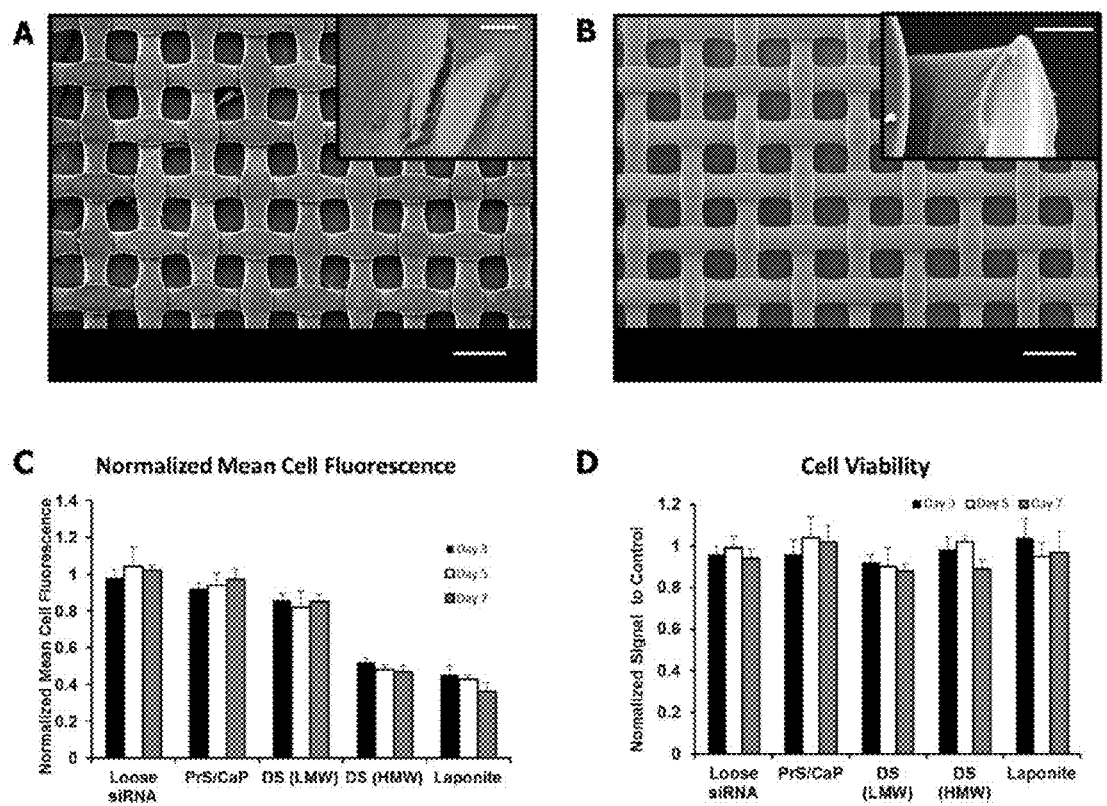
FIG. 3. In vitro characterization of LbL films in accordance with certain embodiments of the present invention. (A) SEM image showing the regular woven pattern of Laponite® containing film coated on Tegaderm® used for in vitro testing. Scale bar=100 flill, inset scale bar=10 f.tm. (B) SEM of uncoated Tegaderm® substsate. Similar scales as in A. (C) Plot of flow cytometry data for NIH-3T3 cells stably expressing GFP exposed to LbL film coated Tegaderm® for 3 (■) 5 (□) and 7 (▩) days. Data is shown as relative mean cell fluorescence normalized to cells treated with siControl containing films of the same architecture. (D) Cell viability of NIH-3T3 cells exposed to LbL film coated Tegaderm® as compared to cells exposed to uncoated Tegaderm®, measured using AlamarBlue® metabolic assay.

Each of the four films was built on a non-degradable inert substrate that could be placed in close contact with cells to function as a reservoir from which the films would degrade and release siRNA. A woven nylon bandage (Tegaderm®) was used as the substrate. Tegaderm® is commonly used in medical practice as a contact layer on top of wounds to reduce tissue infiltration into and unwanted adhesion to the dressing. The structure of the material is highly uniform, consisting of woven fibers of approximately 70 µm in diameter which form pores within the weave of nearly 0.01 mm$^2$ (FIG. 3B). Coating the substrate with LbL film did not disturb these features, as can be seen by SEM in FIG. 3A.

Films were created using both siRNA specific for GFP and a control sequence of siRNA that is known to not target any mRNA sequence (siControl). Knockdown of GFP was followed for one week in vitro. Film coated substrates were placed into culture with GFP expressing NIH-3T3 cells in 48-well plates. Relative mean cell fluorescence of the cell populations treated with each of the different film architectures on days 3, 5, and 7 can be seen in FIG. 3C. GFP expression was most reduced in cells exposed to the (PrS/CaP/PrS/Lap) film architecture. On day 3, cells exposed to this film had a 55% reduction in mean cell fluorescence which increased to 58% by day 5 and finally to a 64% reduction by day 7 compared to cells treated with the siControl containing film. The dextran sulfate containing films achieved very different levels of knockdown. The (PrS/CaP/PrS/DS$_L$) film reached a maximum reduction in mean cell fluorescence of approximately 18% on day 5, which decreased slightly by day 7 to only 14%. The (PrS/CaP/PrS/DS$_H$) film on the other hand achieved nearly a 48% reduction in mean cell fluorescence on day 3 which had increased to a 53% reduction by day 7. The (PrS/CaP) bilayer film showed no measurable reduction in GFP expression over the 1 week period in vitro.

The impact of each film on cell viability was quantified using AlamarBlue assay. The viability of cells exposed to film coated substrates was normalized to cells exposed to uncoated substrates. These results can be seen in FIG. 3D. Cells proliferated rapidly under all testing conditions, growing to near confluence by day 5. Exposure of cells to 100 pmol of free siRNA did not impact cell viability significantly. Only the (PrS/CaP/PrS/Lap) film exhibited no cytotoxicity at any time over the one week test period.

siRNA Film Characterization:

Of the four films tested the (PrS/CaP/PrS/Lap) film showed the greatest reduction in GFP expression, had the least impact on cell viability, and incorporated the most siRNA per area. For these reasons this film was determined to be the best performing film and was chosen to be the focus of further investigation. SEM imaging of the film coated substrate showed near uniform coating with some bridges of film appearing to connect the woven fibers (FIG. 4A). Incorporation of siRNA was similarly uniform over the coated substrate; as seen in confocal imaging using a fluorescently labeled siRNA in FIG. 4B Sections used to render the projection highlight the uniform and continuous nature of the coating of the fibers (FIG. 4C). The sections shown are at 8 µm steps, starting near the apex of a fiber, moving through the fiber until reaching the center.

Figure 4:
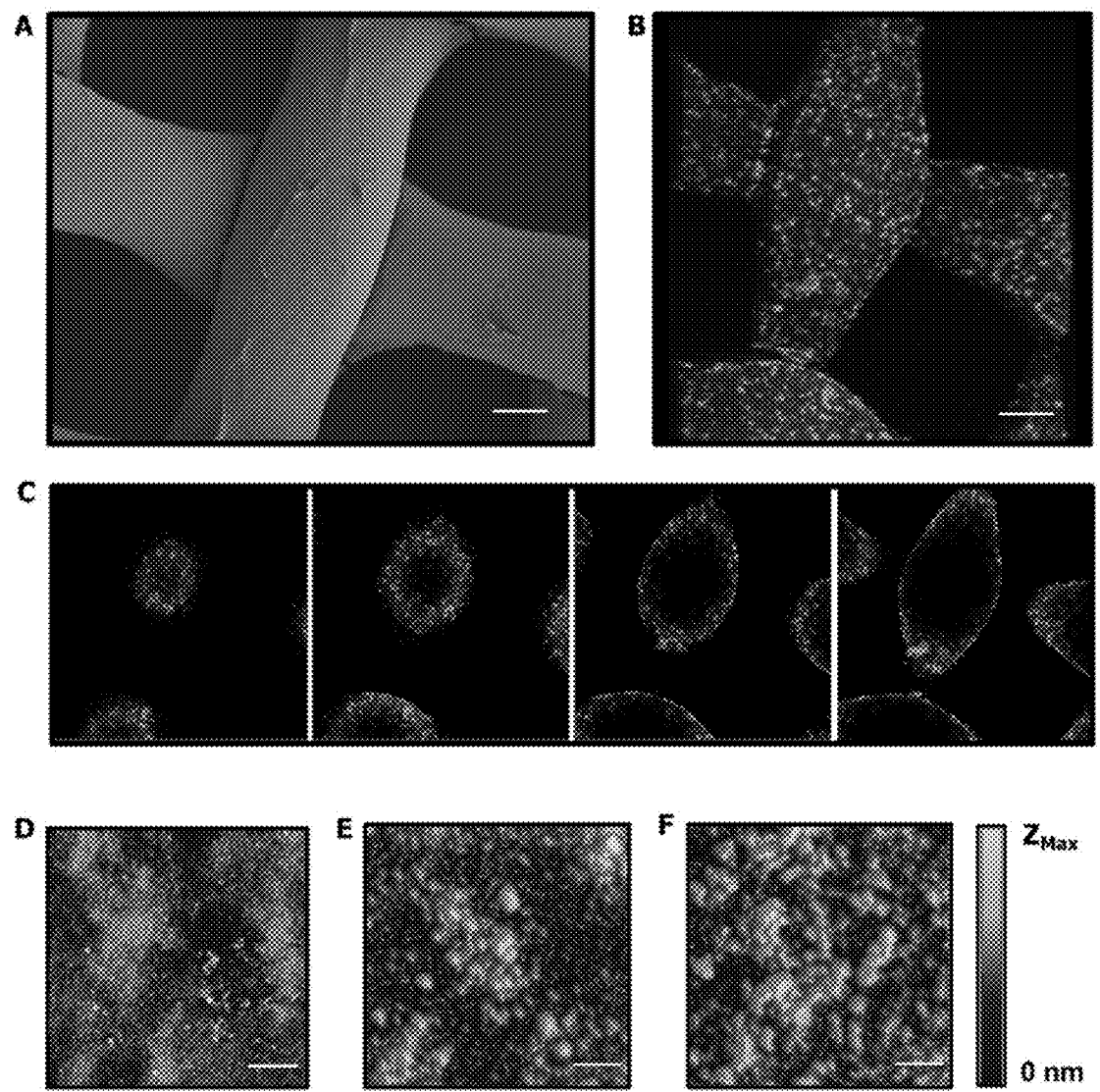
FIG. 4. Characterization of Laponite® containing LbL film coating on Tegaderm® substrate in accordance with certain embodiments of the present invention. (A) SEM imaging of film coated substrate, scale bar=25 μm. (B) Three dimensional projection of fluorescent confocal imaging of film coated substrate using AlexaFluor 488-labeled siRNA. Scale bar=25 μm. (C) Selected confocal images used to generate projected image. Images were selected at 8 um steps to show the conformal nature of the film coating. (D-F) Atomic force micrographs at 5, 15, and 25 architecture repeats respectively, $Z_{max}$=57 nm (D), 138 nm (E), and 182 nm (F), scale bar=5 μm.

Fluorescent imaging showed punctate localizations of signal within the film coating (FIG. 4B). To investigate these formations the same film was built on silicon substrates and characterized by atomic force microscopy (AFM). FIG. 4 D-F show the surface topography as measured by AFM at 5, 15, and 25 architecture repeats on the surface. Large (approx. 3-5 µm in diameter) features began to appear on the surface of the film at 15 tetralayers. Dynamic light scattering measurements of the solutions used to construct the film showed no particulate in excess of 300 nm in diameter. This suggests that these aggregations are likely formed on the surface during film growth and do not represent the incorporation of particle aggregates from solution.

Degradation and Sustained Release Profiles of LbL siRNA:

Release of siRNA from the film was followed in cell conditioned media at 37° C. for 10 days using fluorescently labeled siRNA. The release profile can be seen in FIGS. 5A and 5B. Over the first six days of degradation, the film released siRNA at an average rate of 1.8 µg/cm$^2$ per day. This rate dropped to approximately 0.5 µg/cm$^2$ per day after day 6 until the end of the study period. The cumulative release of siRNA for the 10 days was 12.7 µg/cm$^2$. The total amount of siRNA incorporated within this film was shown to be nearly 19 µg/cm$^2$, meaning that approximately two-thirds of the siRNA incorporated was released over the 10 day test period. No further release of siRNA from the film was observed after 10 days.

Figure 5:
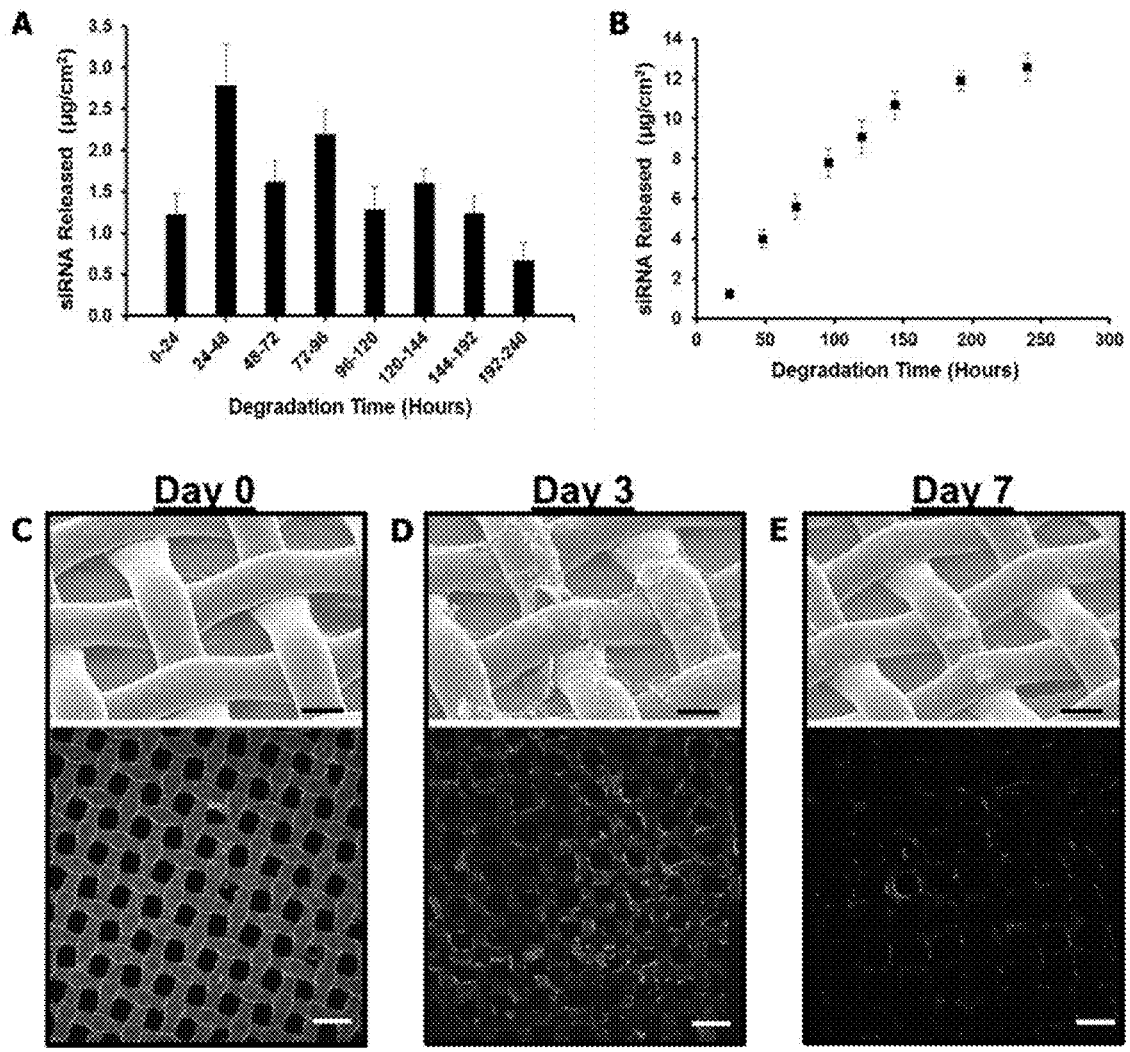
FIG. 5. LbL film degradation and release of siRNA in accordance with certain embodiments of the present invention. (A) Plot of siRNA release measured on a daily (days 1-6) or bi-daily (days 7-10). Release measured during degradation of FITC-labeled siRNA containing film in cell conditioned media. (B) Cumulative release of siRNA over the 10 day period tested. (C-E) Side-by-side comparison of SEM and confocal imaging showing the degradation of the film on day 0 (C), day 3 (D), and day 7 (E), in cell conditioned media. SEM scale bar=50 μm, Confocal scale bar=100 μm.

The degradation and release of the film from the substrate was monitored optically by SEM and fluorescent imaging. A sample taken prior to degradation is shown in FIG. 5C. The non-degraded film coats the substrate with few surface defects and fluorescent imaging shows uniform covering of the substrate with only a few areas of increased fluorescent signal. Samples of degraded film were taken on day three and day seven to inspect the film that remained attached to the substrate. Images of the film at three days of degradation show that it has swelled noticeably and that the distribution of fluorescence along the substrate surface has become less uniform. SEM images show large surface defects in the coating with significant portions of the film loosely bound to the substrate (FIG. 5D). By day seven most of the film has been released from the substrate with only a few large pieces of film remaining attached to the surface. The fluorescent images of the film at this point also show that most of labeled siRNA contained within the film has been released (FIG. 5E).

Figure 6:
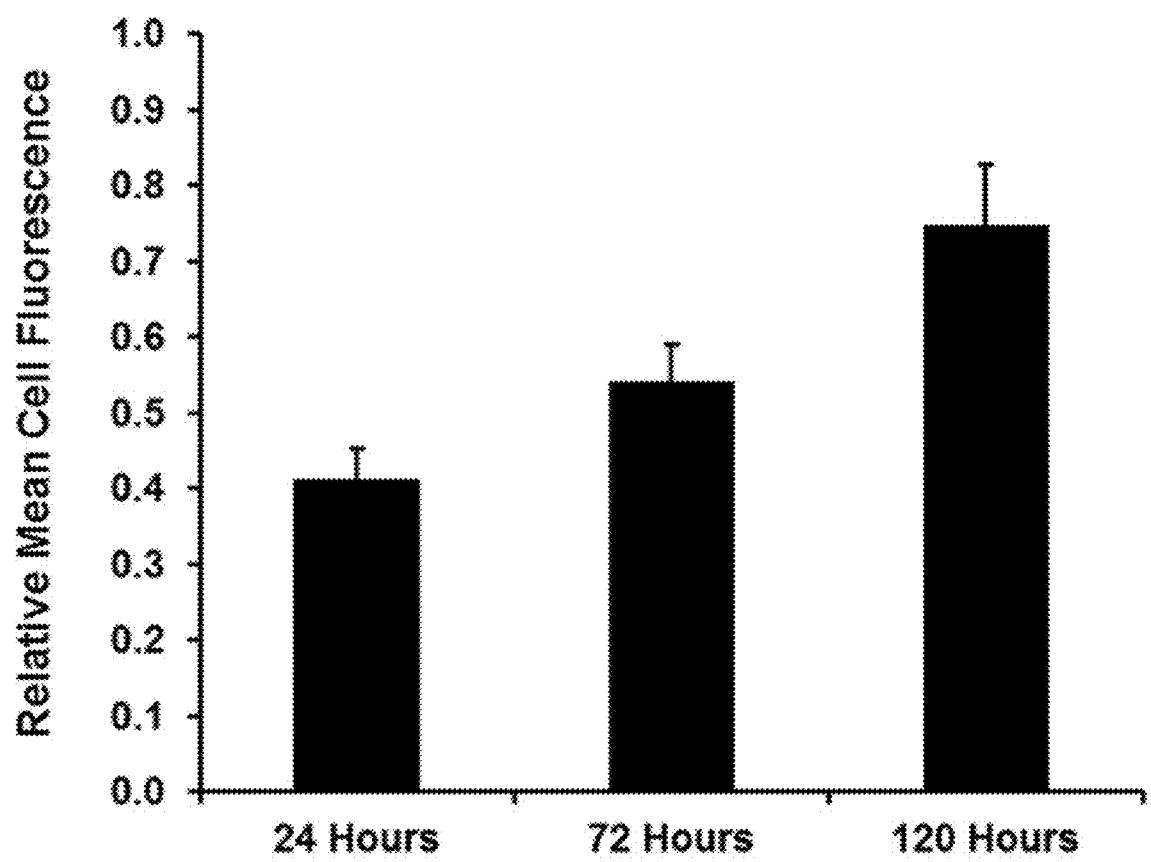
FIG. 6. Continued function of siRNA released from LbL films assessed over a one week period in vitro in accordance with certain embodiments of the present invention. Films introduced to cells after degradation in cell conditioned media for up to five days (120 hours) prior to introduction to cells were still able to affect knockdown of GFP in NIH-3T3 cells.

Demonstration of Maintained siRNA Bioactivity:

Degradation and release studies showed that siRNA was released from the LbL film for up to 10 days in vitro. As siRNA is known to undergo rapid nuclease degradation when unprotected, it was important to ensure that the siRNA released at later time points was still bioactive. To investigate this, films were degraded for 24, 72, or 120 hours in cell conditioned media prior to introduction to GFP-expressing NIH-3T3 cells. Cells were then exposed to these pre-degraded films for 72 hours and mean cell fluorescence was measured using flow cytometry (FIG. 6). All films tested reduced GFP expression relative to control films. The extent to which the films reduced mean cell fluorescence was comparable to the estimated siRNA release under the test conditions (24 hour: 6.6 μg/cm$^2$; 72 hour: 5.1 μg/cm$^2$; 120 hour: 2.9 μg/cm$^2$). A slight reduction in function could also be due to degradation of the siRNA released or changes in the way that the siRNA is complexed when it is released from the film at later periods.

Figure 7:
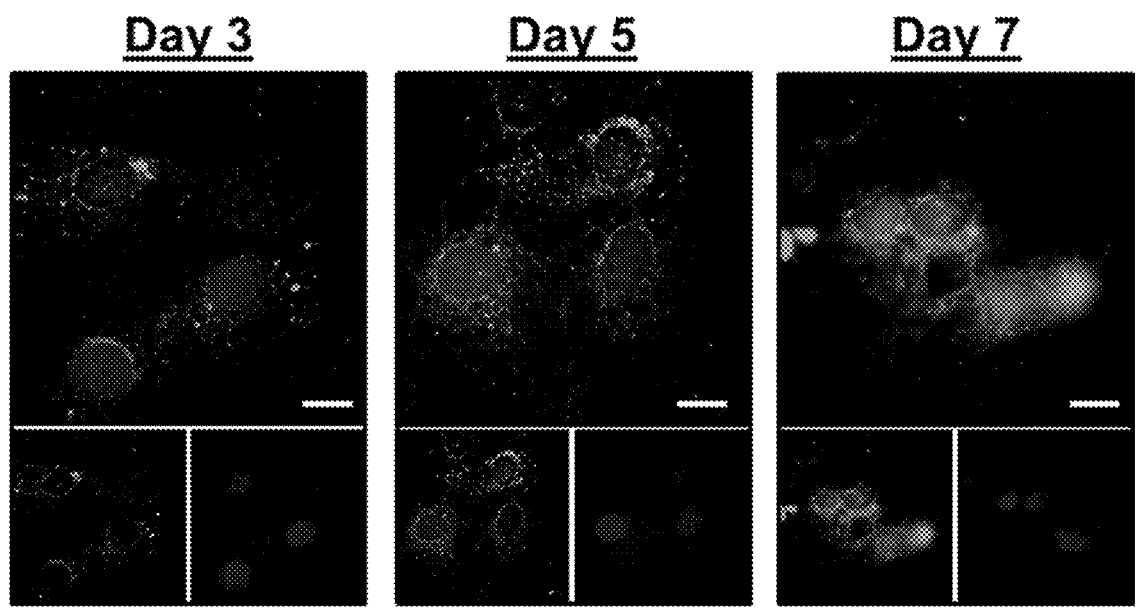
FIG. 7. siRNA released from LbL assembly continues to transfect cells and remains active over 1 week period in vitro in accordance with certain embodiments of the present invention. Uptake of FITC-labeled siRNA by NIH-3T3 cells at 3, 5, and 7 days exposure to LbL films containing labeled siRNA. Cells were seen to become more diffusely fluorescent over the one week period. Scale bar=10 μm.

Cellular Uptake of siRNA:

The uptake of siRNA released from the degrading film was followed in NIH-3T3 cells using a fluorescently labeled siRNA over a 1 week period. FIG. 7 shows images of 3T3 cells after being exposed to the degrading film for 3, 5, and 7 days respectively. At day three the fluorescent signal within the cells was largely localized to punctate spots. By day 5 and 7 cells were more diffusely fluorescent although they still contained many punctate localizations of fluorescent signal.

Figure 8:
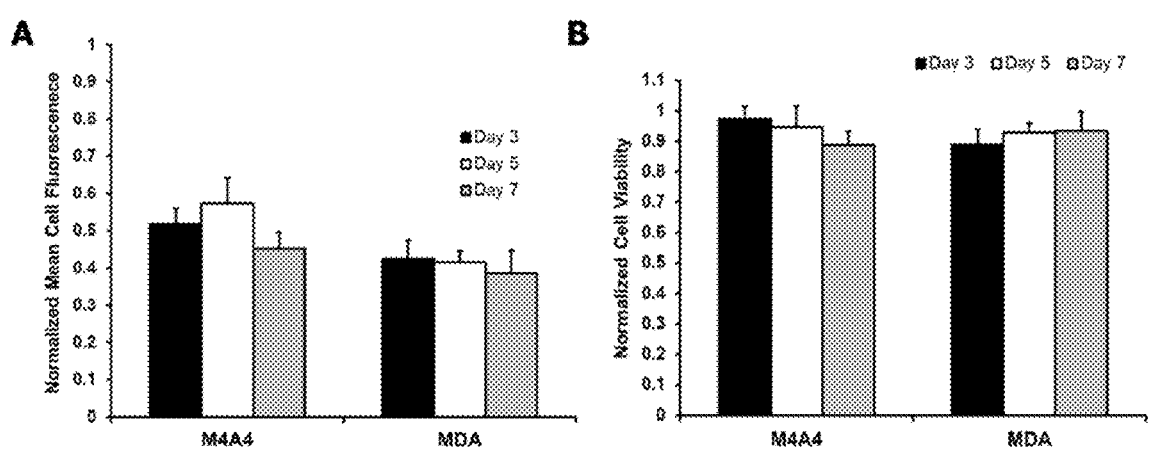
FIG. 8. Knockdown of GFP characterized in two separate cancer cell lines in accordance with certain embodiments of the present invention. (A) Flow cytometry measurement of mean cell fluorescence of either MDA or M4A4 cells that constitutively express GFP exposed to GFP-siRNA containing LbL films followed over a 1 week period. Data shown normalized to mean cell fluorescence of cells exposed to siControl containing film of the same architecture. (B) Viability of cells exposed to coated Tegaderm® substrate normalized to cells exposed to uncoated substrates. Viability measured by metabolic assay AlamarBlue.

Extension to Knockdown in MDA-MB-435 and M4A4 Cells:

To this point all knockdown experiments were performed using NIH-3T3s as a representative cell type. To evaluate the effectiveness of this film in achieving knockdown in more cell types, two commonly used cancer cell lines that were made to constitutively express GFP, MDA-MB-435 and M4A4 were investigated. Similar to testing with 3T3 cells knockdown of GFP was seen by day three in both cell types and was maintained for the entire one week study (FIG. 8A). Cell viability was seen to be reduced (FIG. 8B) in the M4A4 cells over the one week period, although it remained relatively high (~90%) compared to that of cells treated with uncoated controls. These results suggest that delivery of siRNA from this film can transfect multiple cell types and provide interesting capabilities for this modular platform in future use.

The nano-layered siRNA dressings presented in this work demonstrate an effective method for the incorporation and localized delivery of siRNA. Plain nylon bandages when coated with the film developed here achieved and maintained significant gene knockdown in multiple cell lines for one week in vitro without external transfection agents. The films are only a few hundred nanometers in thickness and coat the dressings uniformly, leaving the structure of the bandage unaffected. In total, four distinct siRNA delivering LbL film architectures were detailed and evaluated to isolate the best performing for a more focused investigation. The materials used in creating the films were all biocompatible and all process steps were done in aqueous solution at mild pH and ionic strength conditions. This approach helps demonstrate the impact that different multilayer compositions have on drug delivery characteristics, independent of film thickness or drug loading.

The ability to deliver siRNA locally in a controlled and sustained manner is a promising tool in many areas where modulation of local cellular responses could provide benefit. The capability to load siRNA into an ultra-thin polymer coating for safe and effective delivery of siRNA over an extended period of time provides a significant advance in the existing capabilities of RNA interference. The film described in this work has great potential in many applications ranging from coatings for medical implants and tissue engineering constructs to uses in molecular biology and basic research.

Example 2

Figure 9:
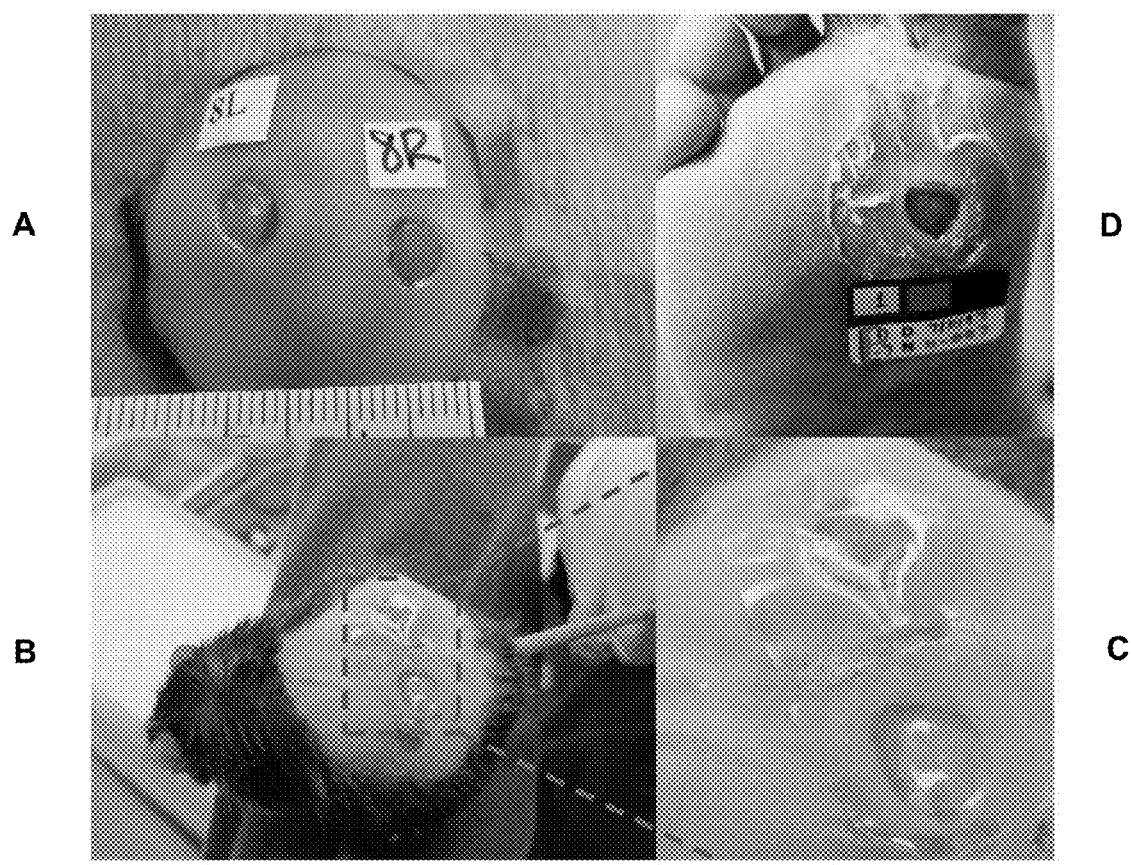
FIG. 9. In Vivo Application of Coated Bandages. (A) Leprdb/db mouse wounded with a 6 mm biopsy punch to created full-thickness dermal wounds. (B) Leprdb/db mouse covered with adhesive bandage (including Tegaderm®). (C) Leprdb/db mouse wound area with adhesive bandage (including Tegaderm®). (D) Full-thickness dermal wounds on the base of a human foot covered with adhesive bandage (including Tegaderm®).

The effectiveness of nano-layered siRNA dressings prepared and described in Example 1 was tested in a well-established in vivo model of chronic wound healing, the Lepr$^{db/db}$ mouse. The Lepr$^{db/db}$ mouse was wounded with a 6 mm diameter biopsy punch to form full-thickness dermal wounds. Two wounds were inflicted and both wounds treated with the same treatment. The entire wound area was dressed including Tegaderm® with ~5 mm diameter dressing. The dressing was placed in the wound and covered with an adhesive bandage to maintain the coated bandage within the wound (FIG. 9).

Example 3

The present Example demonstrates effective delivery of Matrix Metalloproteinase-9 (MMP-9)-targeted siRNA from LbL films in accordance with the present invention.

Figure 29:
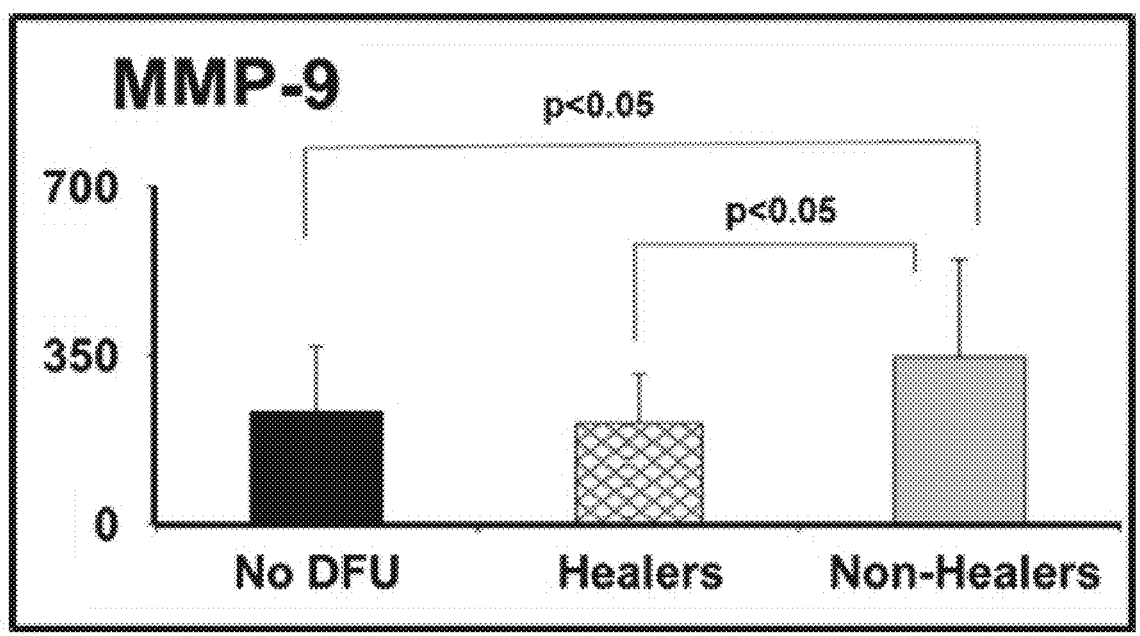
FIG. 29. Graph of Matrix Metalloproteinase-9 (MMP-9) expression demonstrating active MMP-9 is increased within wound fluid of chronic/poor healing diabetic ulcers.

Active MMP-9 is increased within wound fluid of chronic/poor healing diabetic ulcers. As shown in FIG. 29, active MMP-9 degrades collagen within the wound and overexpression is linked to reduction in granulation tissue. See Moor A N. Wound Repair Regen. 2009; 17; Spenny M. Wound Repair Regen., 5, (2002); Ladwig G P. Wound Repair Regen., 10 (2002); Liu Y. Diabetes Care, 32, (2009); Antezana M. J. Invest. Dermatol., 119, (2002); Dinh et al, Diabetes, 6 (2012); Erbe D V et al, Diabetes Obes. Metab., 11 (2009), the contents of these articles are incorporated herein by reference.

Figure 10:
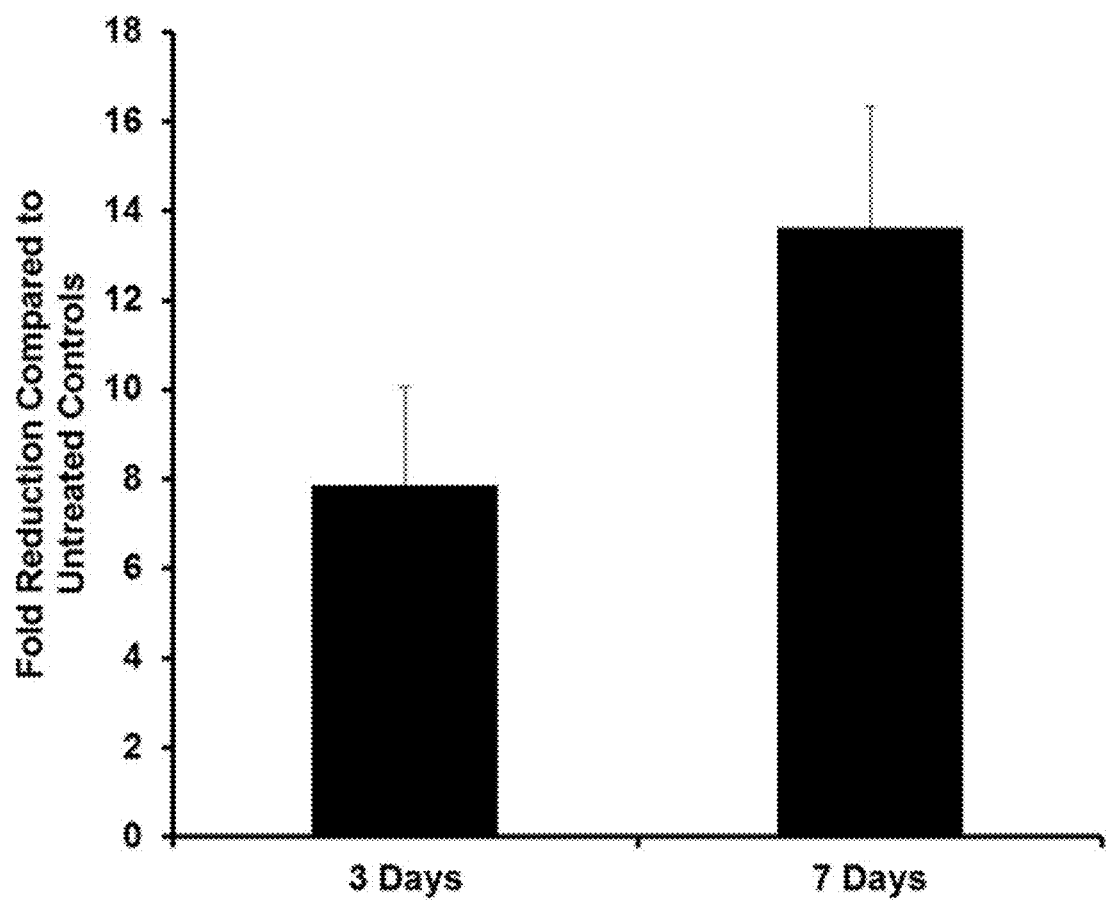
FIG. 10. siRNA-Specific Reduction of MMP-9 Expression in Wound Bed in accordance with certain embodiments of the present invention. Fold reduction in MMP-9 expression in wound beds of mice treated with LbL films containing MMP-9 siRNA and those given bare dressings.

The MMP-9 siRNA films of the present example were assembled on calcium phosphate nanoparticle containing LbL film. Knockdown of MMP-9 was monitored using qRT-PCR and the fold reduction in expression was calculated using the delta-delta Ct method comparing MMP-9 mRNA levels to β-Actin within the wound bed between mice treated with either the LbL film coated substrate or bare Tegaderm®. This data is presented in FIG. 10.

Figure 11:
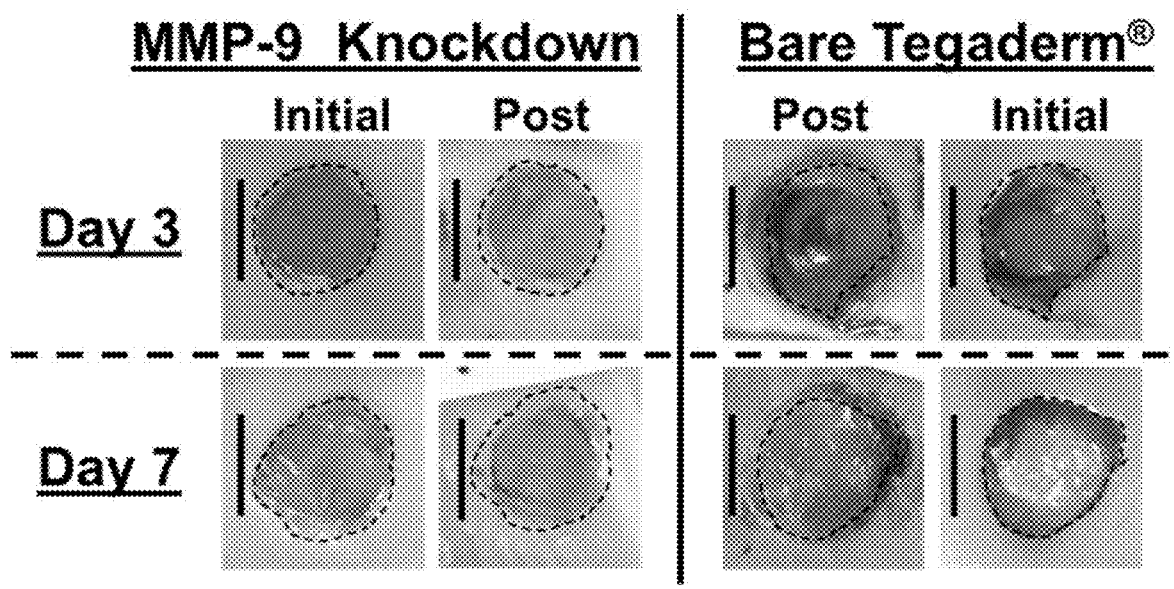
FIG. 11. Digital Monitoring of Wound Closure in Treated vs. Untreated Mice in accordance with certain embodiments of the present invention. Images show wounds on day 3 and day 7 after wounding and application of specified dressings. The dashed line represents the initial wound margin. Scale bar=5 mm in all images.

Mice treated with the MMP-9 specific siRNA LbL film were also seen to have accelerated wound closure using digital imaging (FIG. 11).

Figure 12:
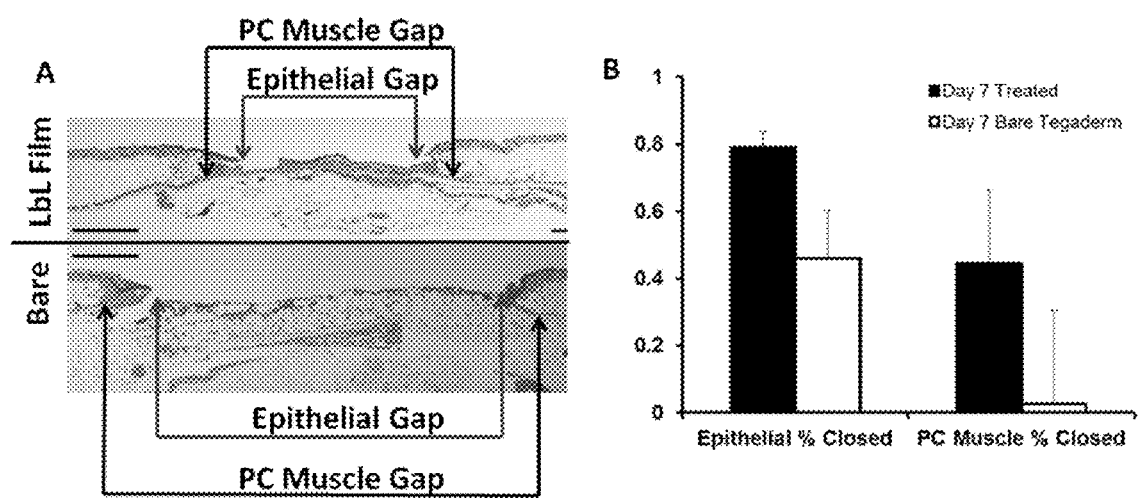
FIG. 12. Histological Analysis of Wound Closure in accordance with certain embodiments of the present invention. (A) H&E stained histology of center-of-wound sections. LbL Film treated wounds had significantly accelerated closure of both criteria measured. (B) Comparison of closure of epithelium and panniculus carnosus muscle in treated and untreated mice as percent of initial wound total area.

Histology of these wounds was analyzed to monitor the closure of both the epithelium and the panniculus carnosus muscle (FIG. 12A). Acceleration in wound healing wound be demonstrated as increase closure of these two dermal structures at a faster rate. This data is quantified in FIG. 12B.

Figure 13:
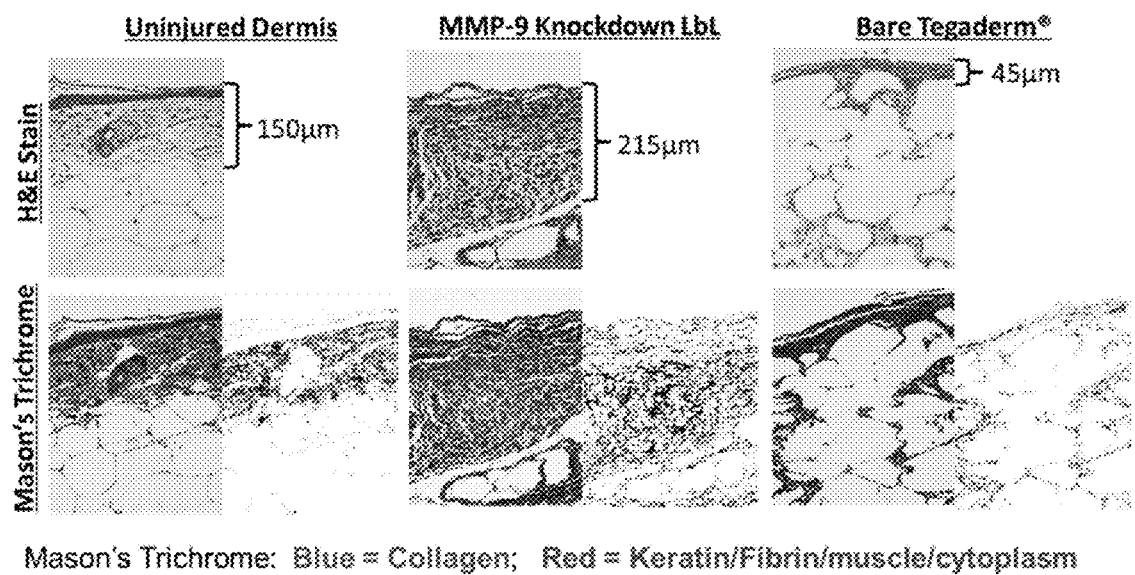
FIG. 13. Collagen Deposition within the Healing Wound Closure in accordance with certain embodiments of the present invention. Comparison of tissue thickness formed over the wound in H&E staining (thickness of tissue to the right of image). MT staining showed increased collagen deposition within the formed tissue. Black and white images to the right of MT stain have been processed to only shown blue (black) all other colors have been removed.

As MMP-9 is the primary gelatinase expressed in the dermis its knockdown would result in increased collagen deposition. To analyze this, Mason's Trichrome stain (MT Stain) was used, which selectively stains collagen blue. FIG. 13 compares Hematoxylin and eosin (H&E Stain) staining along with MT staining of uninjured dermis, MMP-9 Knockdown film treated, and bare bandage treated wound histology.

This data taken together presents a substantial argument for the capability of this described siRNA delivering LbL coating in local application for the acceleration of wound healing. Quantitative Real-Time Polymerase Chain Reaction (qRT-PCR) of MMP-9 expression within the wounds of mice treated with MMP-9 specific siRNA and bare bandage showed significant reduction in expression (8-fold by 3 days and 14-fold by 7 days after application of treatment). Gross analysis of digital imaging of wounds shows that wound treated with the siRNA delivering LbL film were significantly small in total area after only 1 week of treatment. Histological analysis confirmed this in both criteria investigated (epithelium and panniculus carnosus muscle closure). Analysis of collagen deposition within the wound, the primary MMP-9 effected molecule within the wound showed significantly increased deposition in treated vs. untreated wounds. Taken together in vitro and early in vivo testing show that the film coating described here is a highly effective delivery vehicle for localized RNAi therapies.

Example 4

Figure 14:
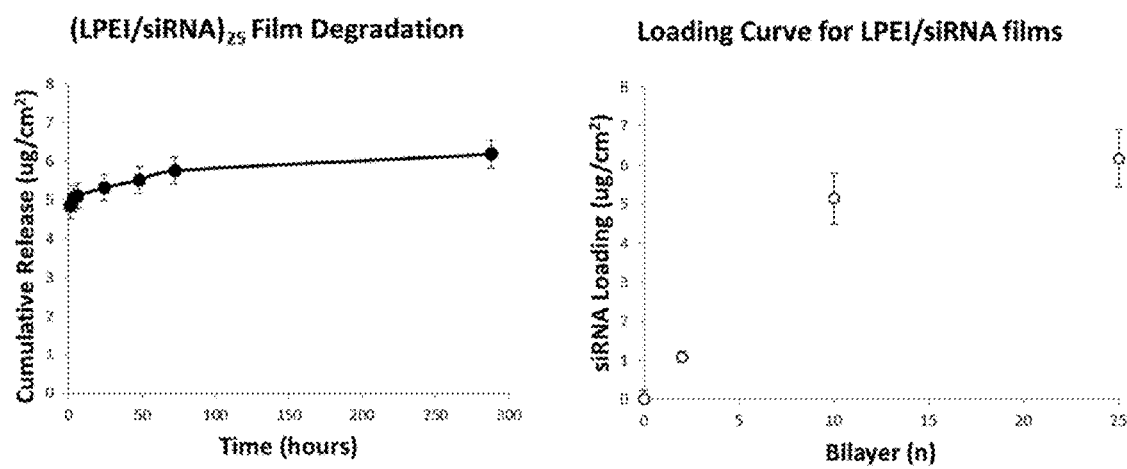
FIG. 14. siRNA Release and Loading for (LPEI/siRNA)$_{25}$ Film in accordance with certain embodiments of the present invention. Nearly 80% of loaded siRNA released from the thin film within 30 minutes of degradation in PBS (pH 7.4), release of siRNA was seen to trail off for over 10 days.

This work focuses on incorporating siRNA as a polyelectrolyte directly into anLbL assembly for systemically delivered RNA interference. According to some embodiments of the present invention and as demonstrated in this Example, direct incorporation of siRNA into an LbL film is capable and simple to obtain independent release profiles for different siRNAs. The present Example describes direct incorporation of siRNA agents into different LbL films and/or different substrate preparations.
LPEI/siRNA (L/S) Films A linear PEI was used as it has been successfully applied in nucleic acid delivery and has been used in many RNAi applications. FIG. 14 shows the siRNA release and loading curve for this film. The film was prepared in a 0.1 M sodium acetate solution at pH 5.0. As can be seen nearly 80% of the loaded siRNA released from the film within minutes after introduction into the releasing media (PBS, pH 7.4).

Figure 15:
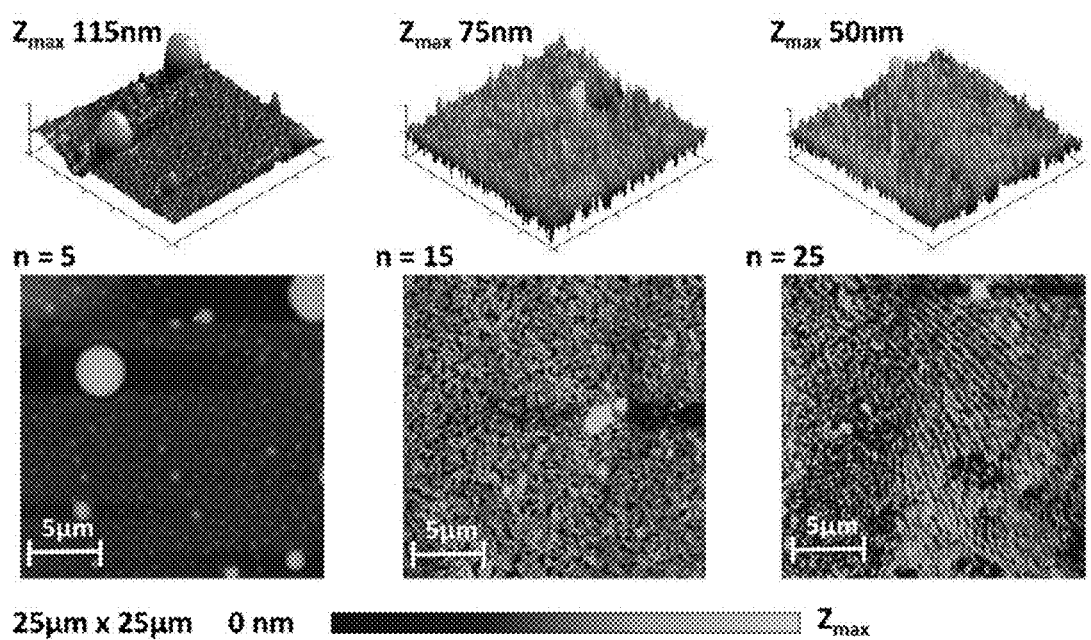
FIG. 15. Atomic Force Micrographs for LPEI/siRNA Bilayer Films in accordance with certain embodiments of the present invention.

Attempts to measure film growth as a function of the number of layers of film adsorbed to the surface was unsuccessful and as such we investigated the surface features of the film over its construction by atomic force microscopy (AFM) (FIG. 15). The film was seen to develop from small nucleation sites of film adsorption. After 25 bilayers the film was still not uniform over the coated surface.

Knockdown studies of this film were performed by application of release samples being placed into culture with GFP expressing NIH-3T3 cells. The released siRNA was unable to effect knockdown significantly.
BPEI/siRNA (B/S) Films This film showed no siRNA release and no reproducible measured film growth. 10 kDa and 50 kDa BPEI were used in separate tests. Loading of siRNA was seen to be higher in the 50 kDa BPEI (~12 $\mu g/cm^2$) than the 10 kDa BPEI (~6.8 $\mu g/cm^2$) after 25 bilayers. This film did not release any measurable siRNA for over 2 weeks in PBS (pH 7.4) at 37° C. Film growth was spotty and non-uniform for the 25 layers attempted. The film was tested for knockdown but did not achieve any promising results.
Poly-β-Aminoester/siRNA (P/S) Films Poly-β-aminoesters are a family of degradable polycations. Efforts have been made to use poly-β-aminoesters for RNAi application (see, for example, Lynn et al., Langmuir 2011 Jun. 21; 27 (12): 7868-7876). Specifically, Lynn has reported preparation of a multilayer composition loaded with siRNA. Lynn et al. reported siRNA loading into their composition of 0.9 $\mu g/cm^2$. Lynn et al did not show burst-free nor sustained release of the siRNA. On the contrary, it was demonstrated that ~65% of loaded siRNA within the first hour of incubation was released. This initial burst of release was followed by a second, slower phase of release over the next 23 hours.

Figure 16:
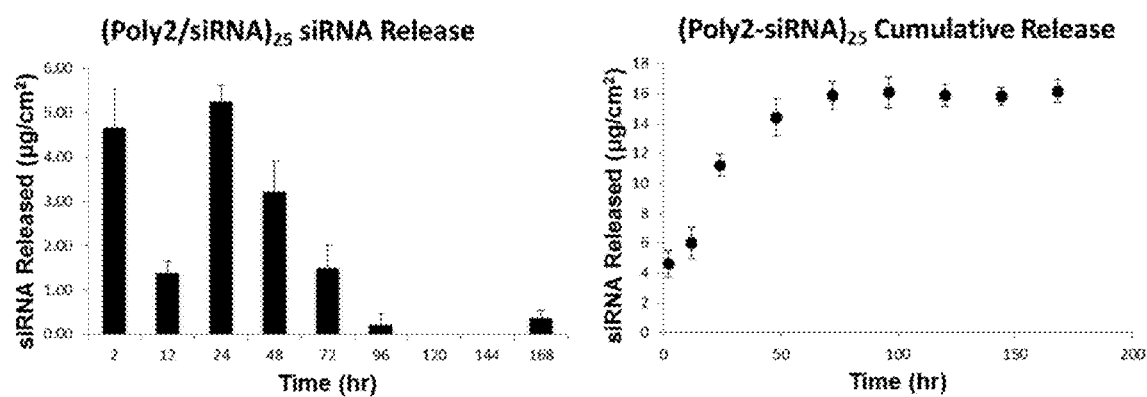
FIG. 16. Release of siRNA from the (Poly2/siRNA)$_{25}$ Film in accordance with certain embodiments of the present invention. Release of siRNA was shown to persist for four days in PBS (pH 7.4) at 37° C.

A multilayer film was built for siRNA delivery using 500 kDa dextran sulfate in base layers together with 25 bilayers of Poly2/siRNA film. A 10 mM sodium acetate buffer was used for siRNA loading. Release of siRNA from this film reached a maximum of nearly 18 $\mu g/cm^2$ and was extended out for approximately 4 days. 40% of the siRNA was released in first four hours. However, siRNA was released at significantly lower levels than loaded. As shown in FIG. 16, 8 $\mu g/cm2$ remained in the film after one week degradation.

Investigation of such film including (Poly2/siRNA)$_{25}$ applied to a nylon woven substrate placed in contact with cells was unable to effect significant levels of knockdown in NIH-3T3 cells. This can be seen in FIG. 27 & FIG. 28.

Thus, prior to the present disclosure, the apparently maximum loading capacity of nucleic acid agents, and particularly of siRNA agents into Poly2/siRNA films was 0.9 $\mu g/cm^2$. However, the Examples surprisingly demonstrates preparation of a multilayer composition that achieved loading as high as about 18 $\mu g/cm^2$. This therefore shows that it is in fact possible to achieve loading levels of nucleic acid agents.
Chitosan/siRNA (C/S) Films Chitosan is a highly biocompatible polymer obtained from chitin and has been used extensively in gene delivery technologies. A low molecular weight fraction of chitosan obtained from Sigma-Aldrich with a molecular weight of approximately 15 kDa was used here.

Figure 17:
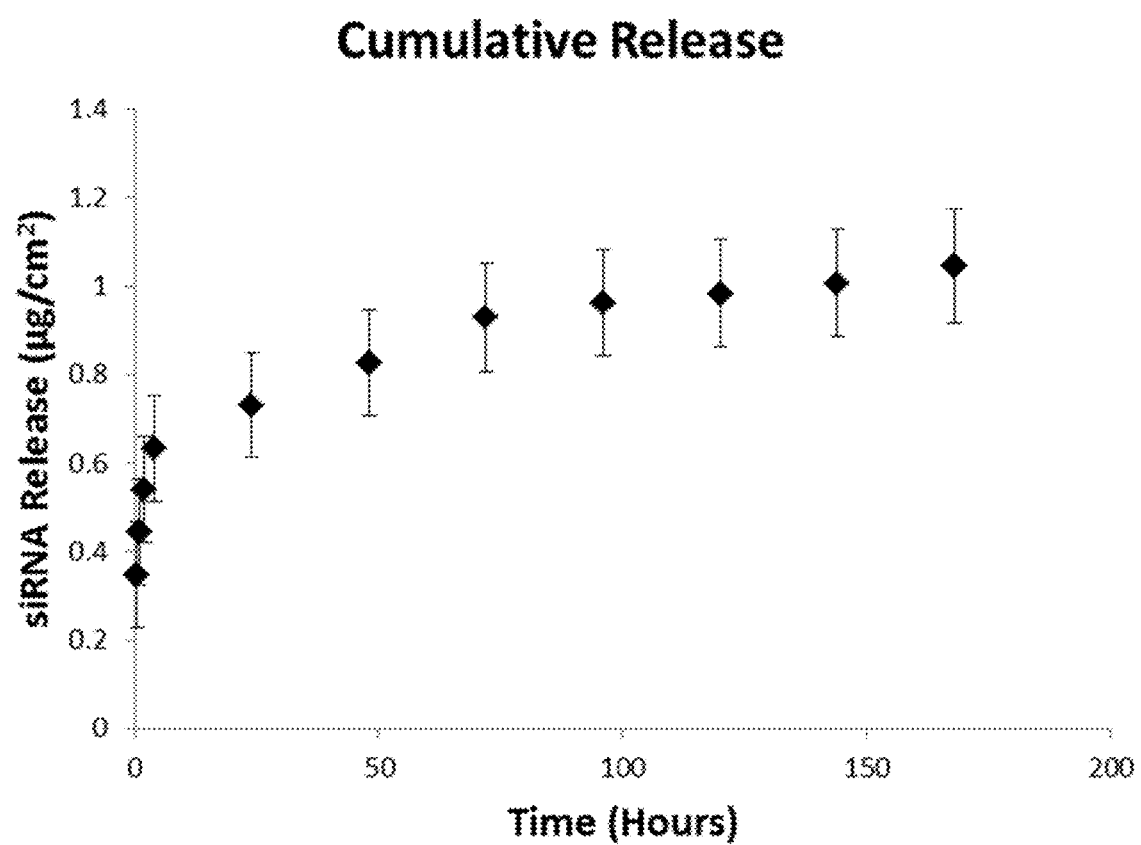
FIG. 17. Release of siRNA from (Chitosan/siRNA)$_{50}$ Film over eight days in PBS (pH 7.4) at 37° C. in accordance with certain embodiments of the present invention. Very little of the loaded siRNA was seen to leave the film during the study period, leaving the film largely intact.

A bilayer architecture of (chitosan/siRNA)$_{50}$ was capable of containing 19.8 $\mu g/cm^2$ siRNA. Degradation of this film in PBS (pH 7.4) at 37° C. can be seen in FIG. 17. Degradations carried out for over eight days showed only a small fraction, approximately 1 $\mu g/cm^2$ of the loaded siRNA was released, leaving the majority of siRNA within the film.
LPEI/siRNA/Dextran Sulfate (L/S/D) Films To achieve full surface charge reversal of LPEI/siRNA bilayer film, another polyanion (other than siRNA alone) was used here. A "tri-layer" LbL film was tested here. It was conducted by first adsorbing as much siRNA as the film could in a manageable amount of time then adsorb another polyanion to complete the layer. This worked to increase loaded siRNA, extend siRNA release, and produce a film that grew nearly linear with respect to layers adsorbed (FIG. 18 & FIG. 19).

Figure 18:
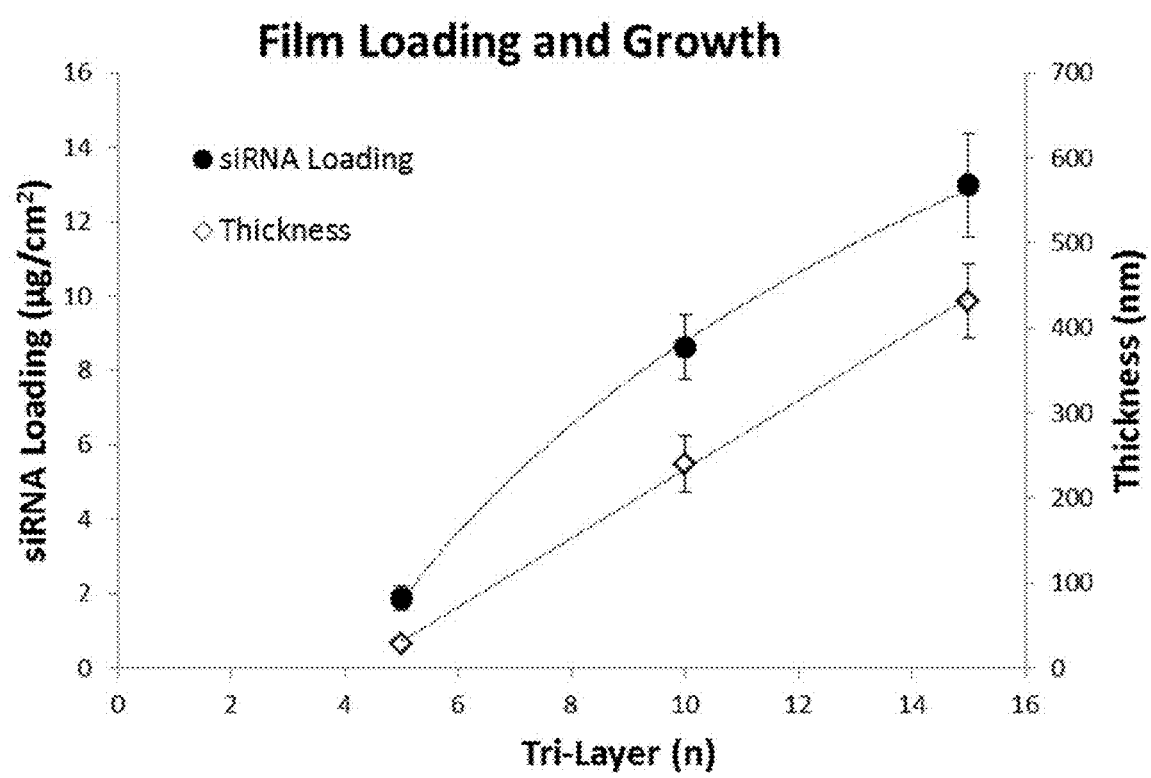
FIG. 18. L/S/D Film siRNA Loading and Growth Curve in accordance with certain embodiments of the present invention. Thickness was evaluated with ellipsometry and profilometry of films built on silicon substrates at 5, 10, and 15 layers.
Figure 19:
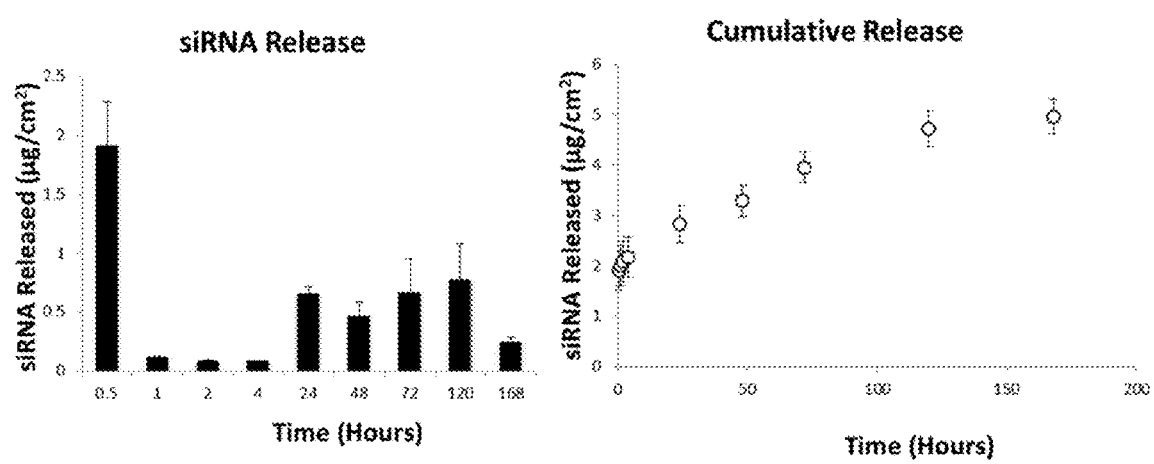
FIG. 19. Release of siRNA From L/S/D Film in accordance with certain embodiments of the present invention.
Figure 20:
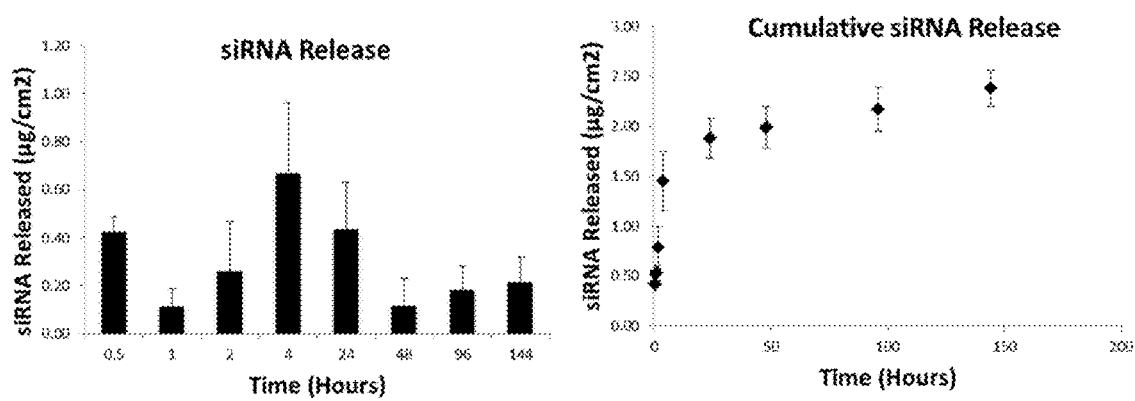
FIG. 20. Release of siRNA from P/S/D Film in accordance with certain embodiments of the present invention.

FIG. 18 shows that by 15 tri-layers nearly 13 $\mu g/cm^2$ had been loaded into the growing film with a total thickness of approximately 435 nm. Release of this film was studied in PBS (pH 7.4) at 37° C. for a period of 1 week. The release profile shows a burst release of approximately 2 $\mu g/cm^2$ initially with sustained release over the next 7 days (FIG. 19). Bolus release occurred within minutes after introduction to PBS accounting for ~35% loaded siRNA and a total loading of siRNA of ~19 $\mu g/cm2$ after 25 bilayers. It is noticeable that a significant portion of the film remained unreleased over the study period.
Poly2/siRNA/Dextran Sulfate (P/S/D) Films Another attempt of a "tri-layer" LbL film was conducted using the degradable polycation Poly2. The addition of dextran sulfate to Poly2/siRNA bilayer may promote uptake and endosomal escape. siRNA loading in this film was very low compared to the Poly2/siRNA film, only approximately 2.5 $\mu g/cm^2$. Release from this film showed a significant immediate burst release with little sustained release over the testing period (FIG. 20).

Figure 21:
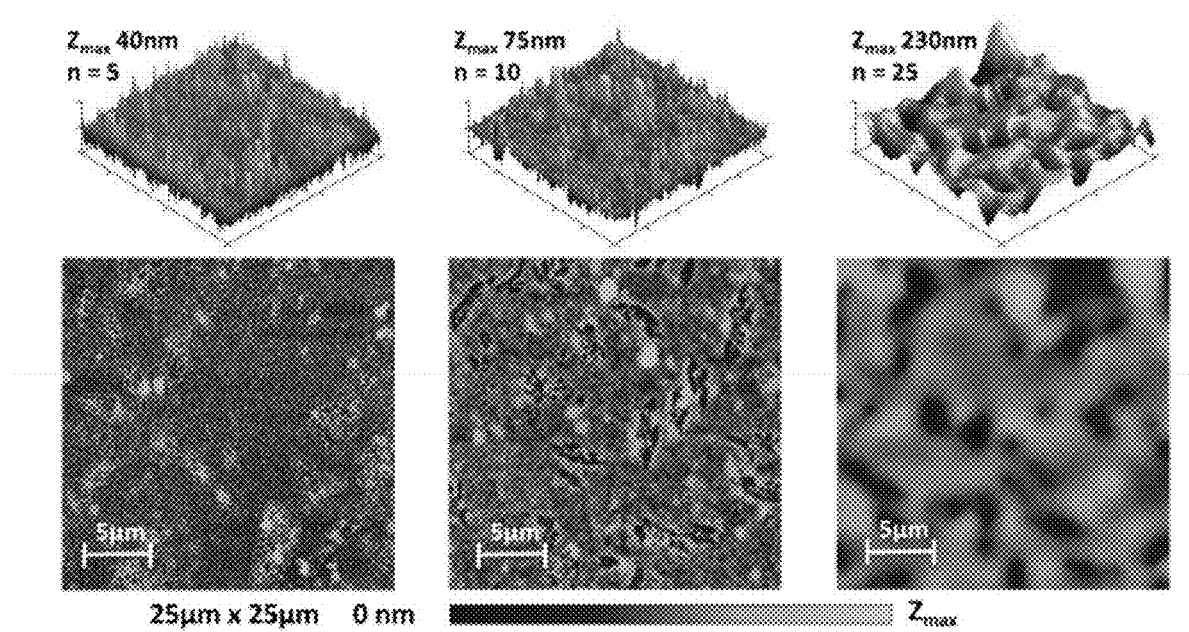
FIG. 21. AFM Imaging of P/S/D Film Growth in accordance with certain embodiments of the present invention.

AFM imaging of the surface showed the poor total coverage achieved by the film over its growth (FIG. 21).

LPEI/siRNA/LPEI/Dextran Sulfate (L/S/L/D) Films

Figure 22:
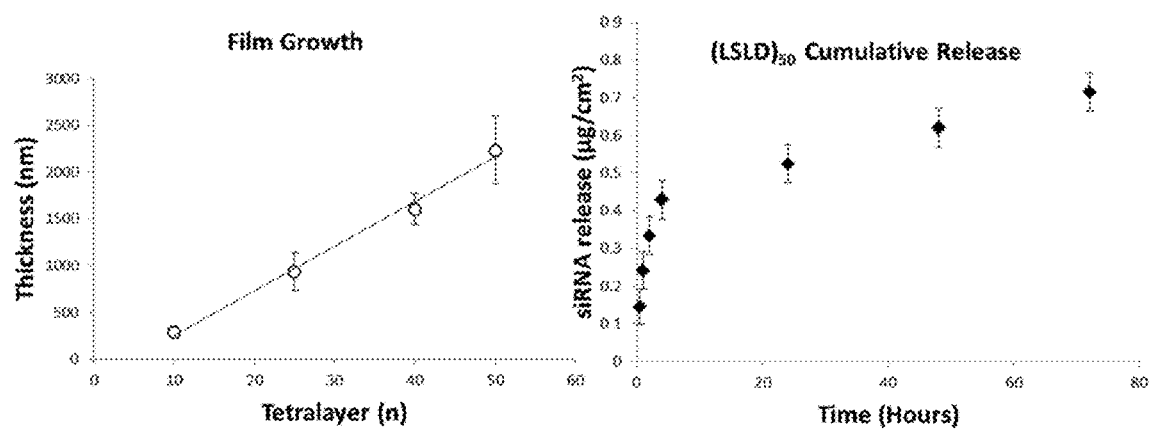
FIG. 22. L/S/L/D Film—Film Growth and siRNA Release in accordance with certain embodiments of the present invention.
Figure 23:
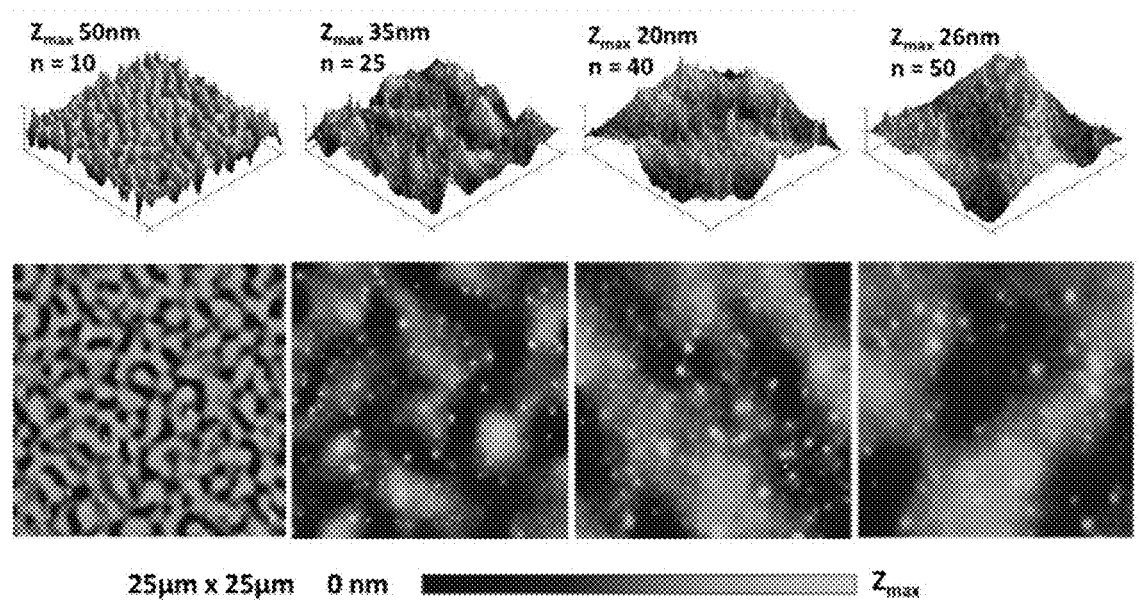
FIG. 23. AFM Imaging of L/S/L/D Film growth in accordance with certain embodiments of the present invention.

Another film architecture, a tetra-layer film was assembled using LPEI as the sole polycation used two times within the film. Film growth and siRNA release for this film are shown in FIG. 22. It was observed that only approximately 1 μg/cm$^2$ of siRNA released from the film over a 1 week period (not all plotted below).

This film was seen visually to have strange optical properties, looking gray-opaque on the silicon it was built on. To investigate the likelihood that we were seeing aggregation within the film AFM imaging of the surface was performed. Early within the film growth an interesting "spinodal" morphology is seen, but later as the film grew this is replaced with a relatively flat surface, not especially indicative of aggregation within the film.

L/S/L/D Film on Top of Degradable Base Layers (Deg BL LSLD)

Figure 24:
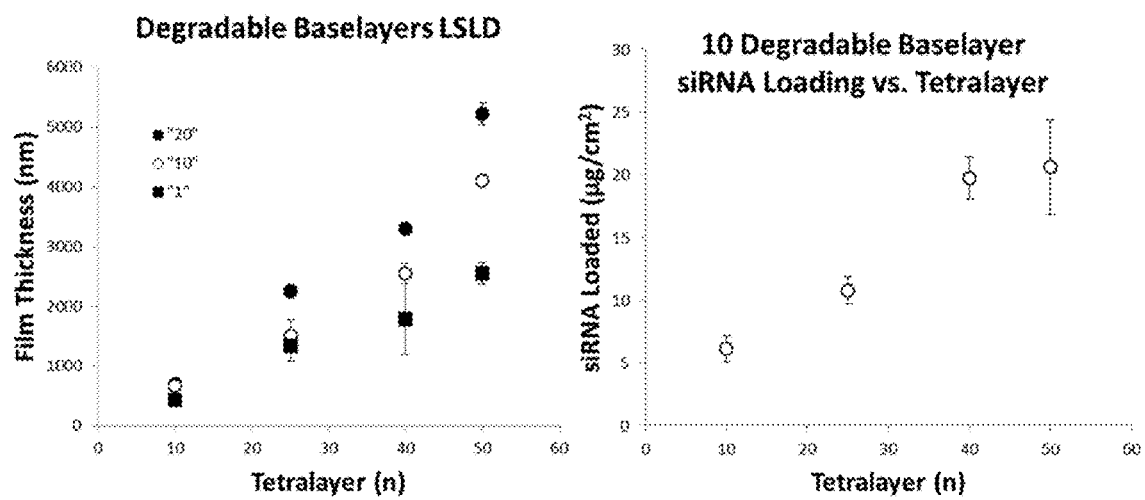
FIG. 24. LSLD Film Growth and siRNA Loading by the Number of Architecture Repeat in accordance with certain embodiments of the present invention.
Figure 25:
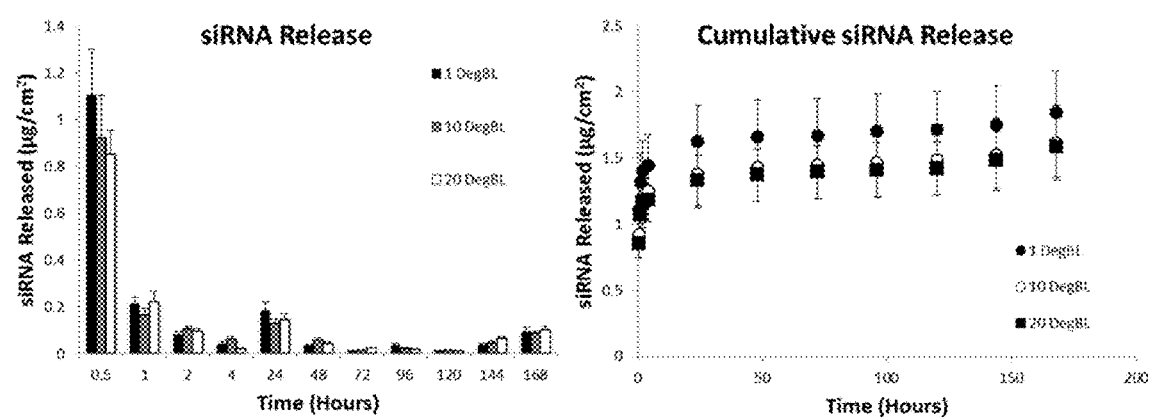
FIG. 25. siRNA Release from LSLD Film. Performed in PBS (pH 7.4) in 37° C. in accordance with certain embodiments of the present invention.

Two or more film architectures can be combined. Given a success release of siRNA using Poly2/siRNA film and a good siRNA loading using LSLD film, these two films were combined, where the LSLD film was built on top of a Poly2/dextran sulfate film would achieve significant improvement in siRNA release and maintain the high siRNA loading. The latter was achieved (FIG. 24) however the former was not as easy (FIG. 15). The 1, 10, and 20 refer to the number of degradable bilayers built below the LSLD film.

(Chitosan/siRNA)$_{50}$ on Degradable Baselayers

Figure 26:
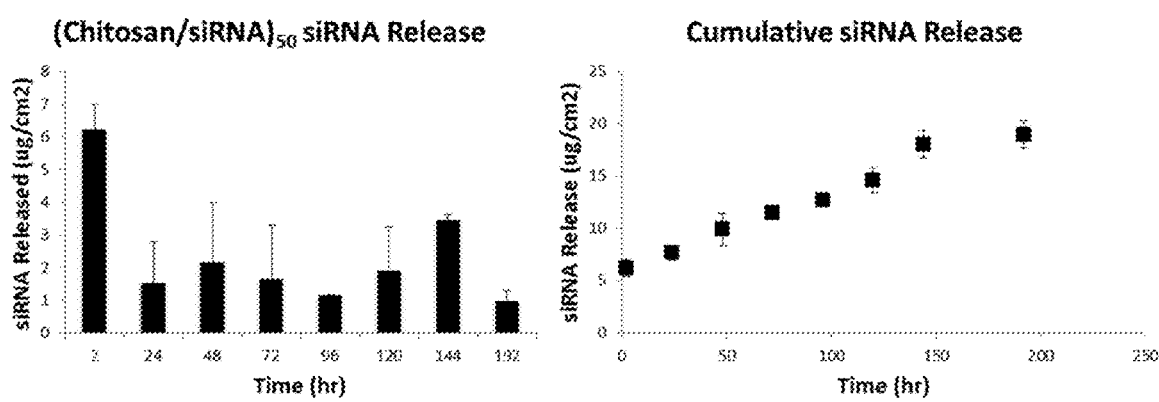
FIG. 26. Release of siRNA from (Chitosan/siRNA)$_{50}$ Film Built on Degradable Baselayers of (Poly2/dextran sulfate)$_{30}$ in accordance with certain embodiments of the present invention. Release profile of film shows a burst release of nearly 30% of all loaded siRNA within 2 hours of degradation with a sustained release over the next eight days in PBS (pH 7.4) at 37° C.

To improve release of siRNA incorporated into the (Chitosan/siRNA)$_{50}$ film, an underlying bilayer film of (Poly2/dextran sulfate)$_{10}$ was built to promote hydrolytic degradation of the film and subsequent siRNA release. That is, a (chitosan/siRNA)$_{50}$ architecture on top of degradable baselayers succeeded in improving the release of siRNA from the film as seen in FIG. 26. Near complete film degradation was seen by day 8 in PBS (pH 7.4) at 37° C. Release of siRNA from this film was sustained over the eight day test period with a burst release of approximately 30% of loaded siRNA coming out of the film within the first few hours of degradation. Total loading of siRNA of ~25 mm/cm$^2$ was achieved using direct incorporation of (C/S)$_{50}$ on a degradable baselayer.

Figure 27:
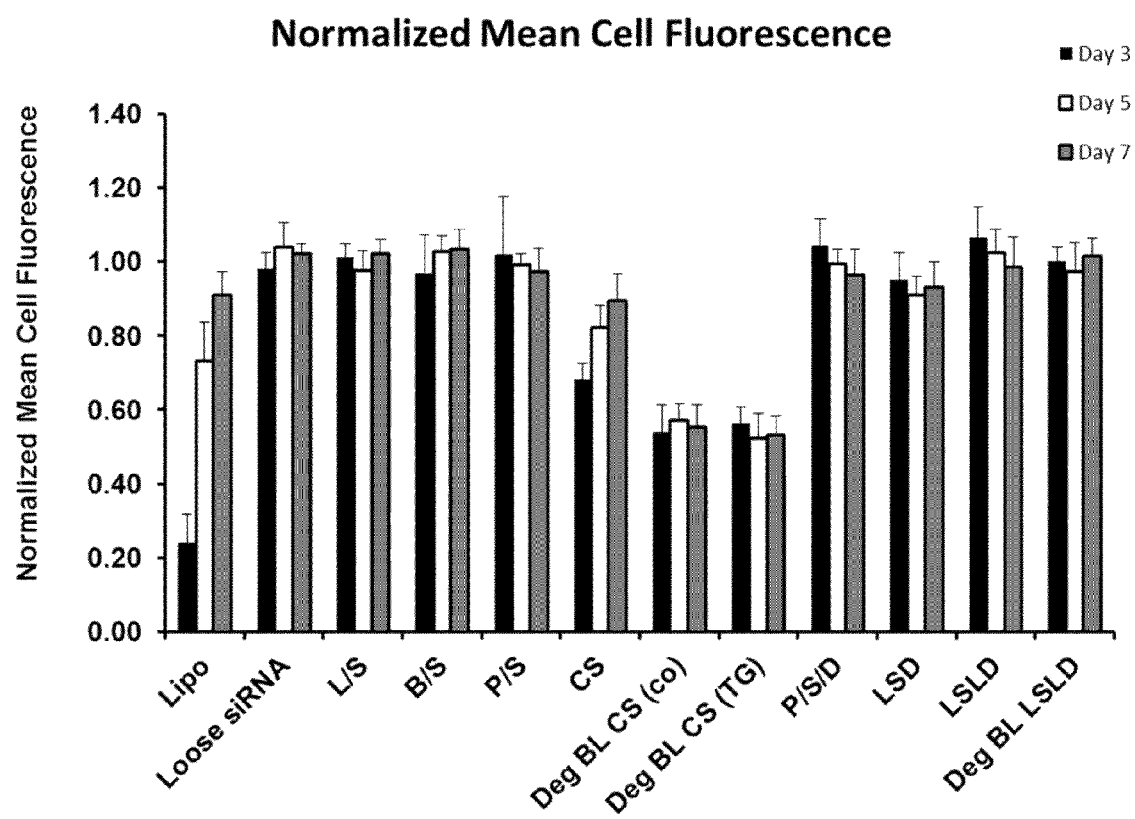
FIG. 27. Relative Mean Cell Fluorescence in accordance with certain embodiments of the present invention. Knockdown of GFP expression in NIH-3T3 after 3, 5, and 7 days of exposure to bandages coated with different LbL films.
Figure 28:
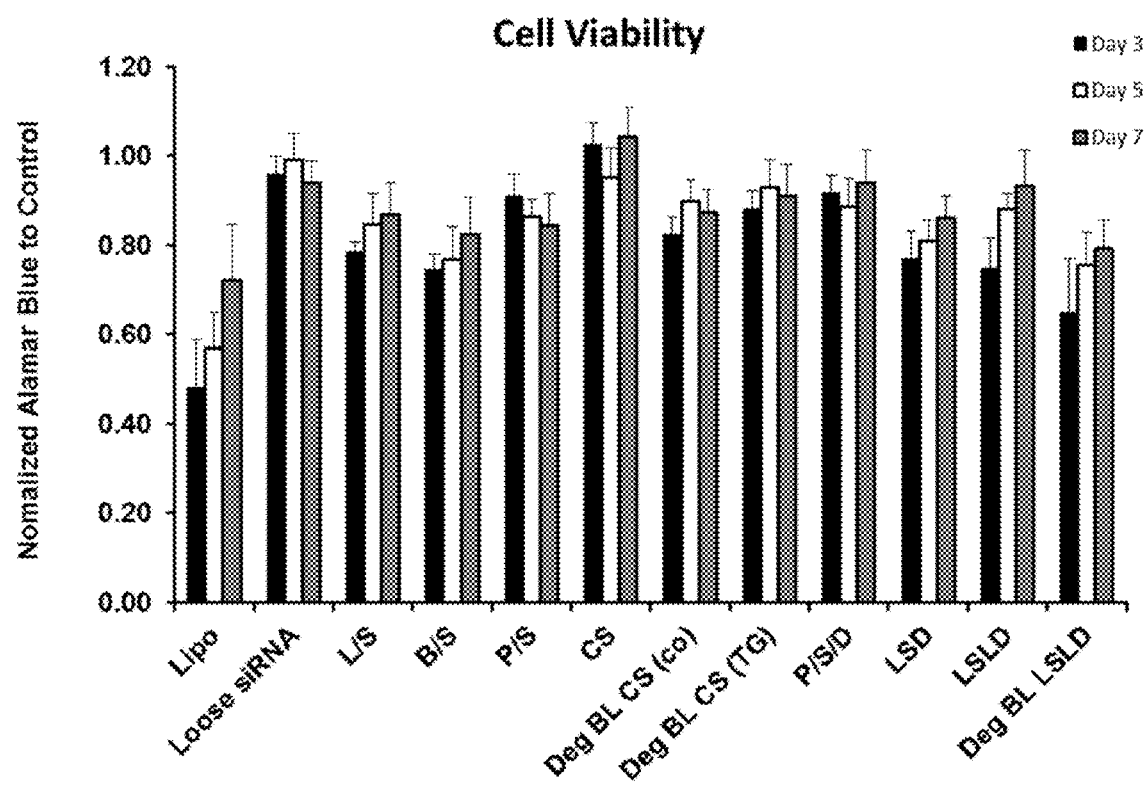
FIG. 28. Cell Viability of NIH-3T3 Cells Exposed to Film Coated Substrates in accordance with certain embodiments of the present invention. This was performed with AlamareBlue® metabolic assay.

NIH-3T3 cells were seeded at 15% confluence (~7,000 cells/well) in a 24-well plate. Films were created using GFP-siRNA, siControl, or uncoated substrate siControl. The uncoated control was used to assess the impact of the films on cell viability. Films of 0.25 cm$^2$ were applied to each well. FIG. 27 & FIG. 28 show time points taken on days 3, 5, and 7. The (Chitosan/siRNA)$_{50}$ architecture on top of degradable baselayers film was demonstrated to successfully achieve knockdown of GFP in NIH-3T3 cells when the film was applied to either a woven nylon mesh (Tegaderm®, TG) (Deg BL CS (TG)) or a polyurethane bandage (CoTran, Co) (Deg BL CS (co)).

In Vitro Testing

Testing of films prepared in this Example was done by coating a commercially available woven nylon bandage (Tegaderm®). The 0.25 cm$^2$ of the coated bandage was placed in a 48-well plate well with cells that constitutively express GFP. Mean cell fluorescence was evaluated using flow cytometry. The relative fluorescence of cells is defined as the ratio of cells exposed to films containing siRNA specific for targeting GFP to films containing an siRNA that targets no mRNA. Cell viability is measured as a ratio of AlamarBlue® metabolic assay for cells exposed to a bandage with coating vs. an uncoated bandage.

Of all the films tested in this Example only the chitosan containing films achieved significant levels of knockdown of GFP. The chitosan/siRNA bilayer film that was built on top of 10 layers of degradable baselayers (Poly2/dextran sulfate) was the most successful. This film was built on two separate substrates for testing, CoTran® and Tegaderm® both marketed by 3M company as a wound covering. This film maintained a high level of siRNA-specific gene knockdown over the entire test period of one week.

Example 5

The present Example confirms that effective systemic delivery of siRNA agents can be achieved from LbL assemblies directly incorporating such siRNA agents as polyelectrolytesas described herein. In particular, the present Example illustrates inhibition of MMP-9 by such siRNA delivery, and resulting accelerated healing of diabetic ulcers.

The present invention encompasses the recognition that MMP-9 siRNA delivery via CaP Nanoparticle film is limited because the film pH cannot drop below ~6.7 without unintentionally degrading the films. This pH limitation reduces the film architectures that can be utilized. Moreover, this pH constraint means that utilized films are incompatible with delivery growth factors. As shown above, direct incorporation films provide an alternative approach. Chitosan/siRNA bilayer was seen to effectively knockdown GFP within NIH-3T3s similar to the CaP films. Investigations showed that it could be used to effectively incorporate siRNA into a film architecture including the growth factor film developed. In some embodiments, direct incorporation offers advantages over other techniques, including absence of particle aggregation concerns, reduced film thickness, and fewer constraints on conditions used to construct films. As shown below, direct incorporation as a technique is broadly applicable to a wide variety of LbL films and layers, agents, etc.

In the present Example, MMP-9 siRNA is incorporated into a (Chitosan/siRNA)$_{50}$ bilayer film. The (C/S)$_{50}$ film is built on top of a (Poly2/dextran sulfate)$_{10}$ degradable baselayer LbL film. This baselayer was built to promote hydrolytic degradation of the film and subsequent siRNA release.

Figure 30:
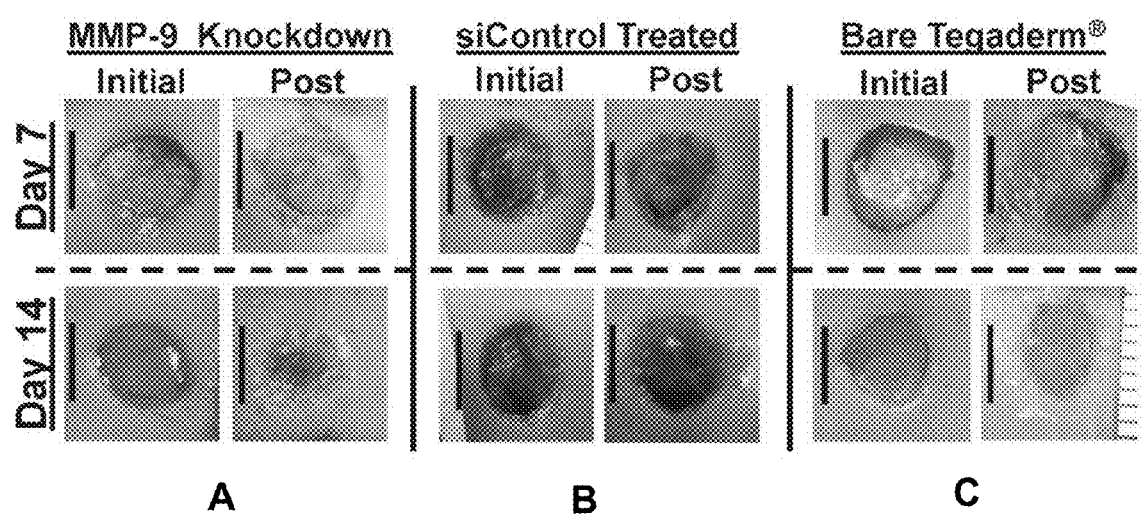
FIG. 30. Imaging of healing in wounds treated with MMP-9 siRNA and wounds untreated. Application of Coated Bandages. (A) Images of wounds treated with bandages having MMP-9 siRNA film assemblies. Top images show wounds at $T_0$ and after 7 days of treatment with bandages coated with an siRNA delivering film. Bottom images show wounds at $T_0$ and after 14 days of treatment with bandages coated with the siRNA delivering film. Wounds treated with bandages coated with siRNA-delivering film show significant healing in comparison to untreated wounds. (B) Images of wounds treated with bandages having siControl film assemblies. Top images show wounds at $T_0$ and after 7 days of treatment with bandages coated with siControl-delivering film. Bottom images show wounds at $T_0$ and after 14 days of treatment with bandages coated with siControl-delivering film. (C) Images of wounds treated with bare Tegaderm®. Top images show wounds at $T_0$ and after 7 days of treatment with bandages coated with bare Tegaderm®. Bottom images show wounds at $T_0$ and after 14 days of treatment with bandages coated with bare Tegaderm®.

A series of images depicting healing of treated wounds and untreated wounds are demonstrated in FIG. 30. MMP-9 si RNA treated wounds display marked healing not seen in untreated wounds. FIG. 30A depicts healing of wounds by treatment including MMP-9 siRNA films. FIG. 30B depicts healing with an siControl sequence. As discussed above, the siControl is a film known to not target any mRNA sequence. FIG. 30C shows healing with bare Tegaderm®. To acquire data points for healing occurring at two time points, two wounds were inflicted for each as show in each FIGS. 30A, 30B, and 30C. The top image for each of FIGS. 30A, 30B, and 30C is labeled Day 7. The left-top image depicts the initial appearance of the wound at $T_0$. To immediate right is the post (healing) appearance of the wound at $T_{day\ 7}$. The bottom image for each of FIGS. 30A, 30B, and 30C is labeled Day 14. The left-top image depicts the initial appearance of the wound at $T_0$. To immediate right is the post (healing) appearance of the wound at $T_{day\ 14}$ (The appearance following day 14 shows some evidence of tearing resulting from integration of the healing wound and the bandage during the two week period and bandage removal). Wounds treated with bandages coated with the siRNA delivering film as seen in FIG. 30A showed clear improvement developing a tough tissue covering the wound after one week and substantial healing after two weeks. As shown in FIG. 30B and FIG. 30C the untreated siControl and Bare Tegaderm® groups did not result in the same healing appearance.

Figure 31:
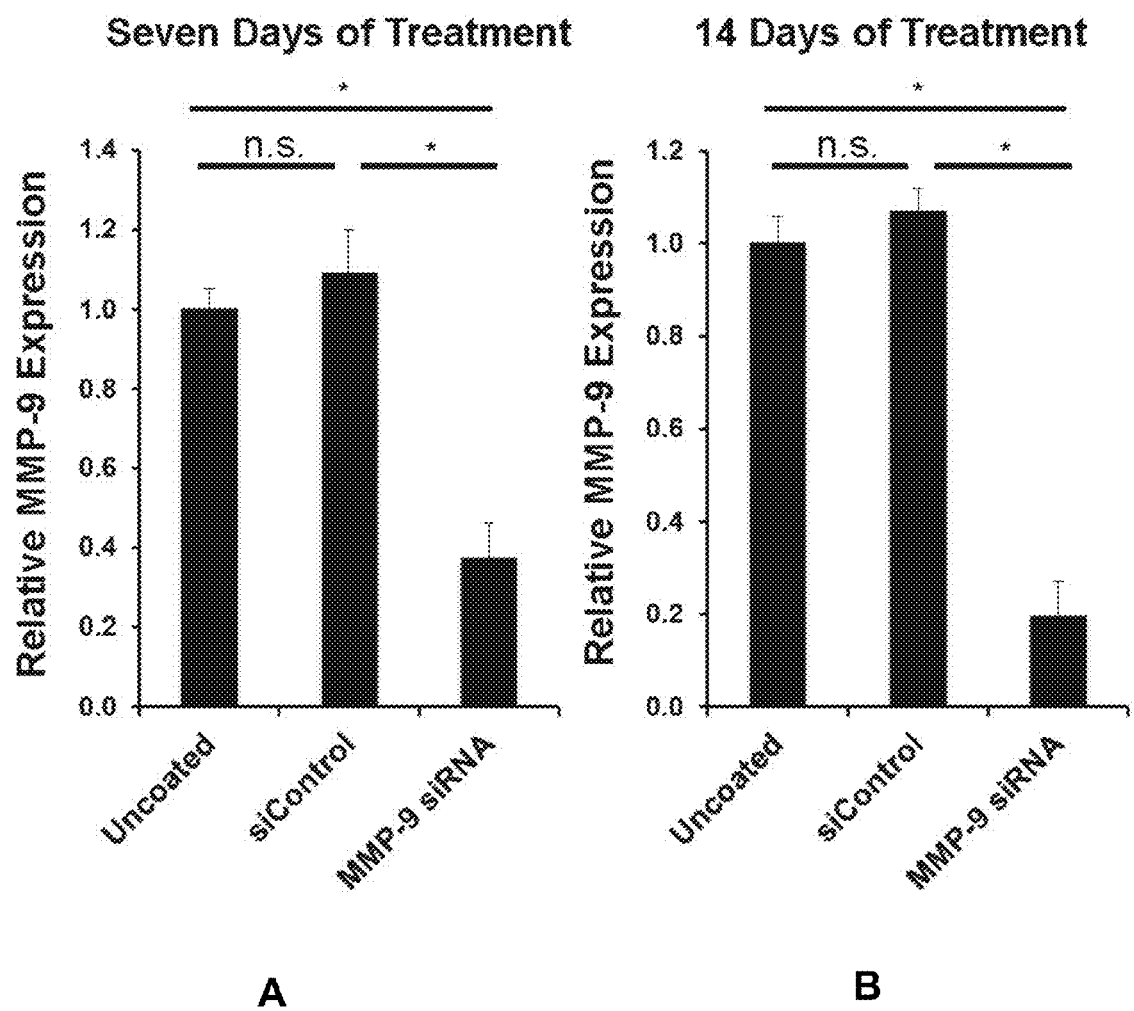
FIG. 31. Quantification of MMP-9 Knockdown in the Diabetic Wound. Graph of relative MMP-9 expression for wounds covered with bandages that are uncoated, bandages with film assemblies of an siControl, and bandages with film assemblies of MMP-9 siRNA at seven days and at 14 days. Wounds covered with bandages treated with film assemblies of MMP-9 siRNA showed a four-fold reduction in MMP-9 by one week (A). Wounds covered with bandages treated with film assemblies of MMP-9 siRNA showed a six-fold reduction in MMP-9 by two weeks (B).

MMP-9 siRNA treated wounds demonstrated reduced MMP-9 expression. FIG. 31 shows MMP-9 knockdown in the diabetic wound corresponding to the MMP-9 siRNA treated films. The wounds for films treated with MMP-9 siRNA had a 4-fold reduction in MMP-9 by one week, this reduction increased to 6-fold by two weeks.

Figure 32:
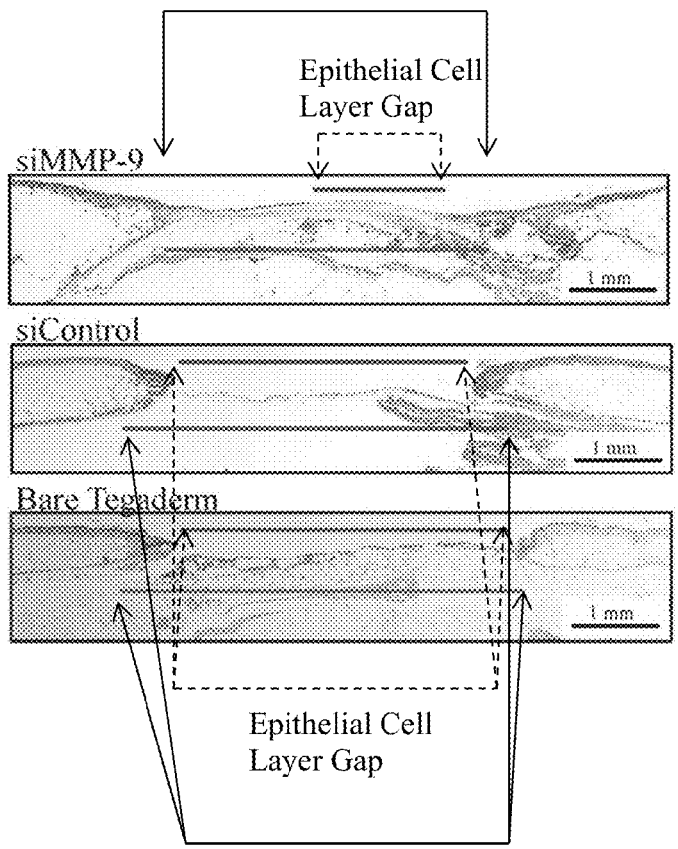
FIG. 32. Histological Analysis of Wound Closure at One Week in accordance with certain embodiments of the present invention. (A) Comparison of closure of epithelium and panniculus carnosus muscle in treated and untreated mice as percent of initial wound total area. (B) H&E stained histology of center-of-wound sections. MMP-9 siRNA LbL Film treated wounds had significantly accelerated closure of both criteria measured.
Figure 32:
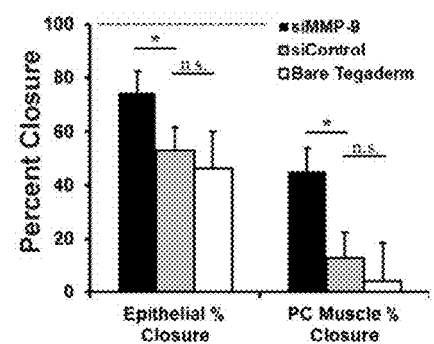
Figure 33:
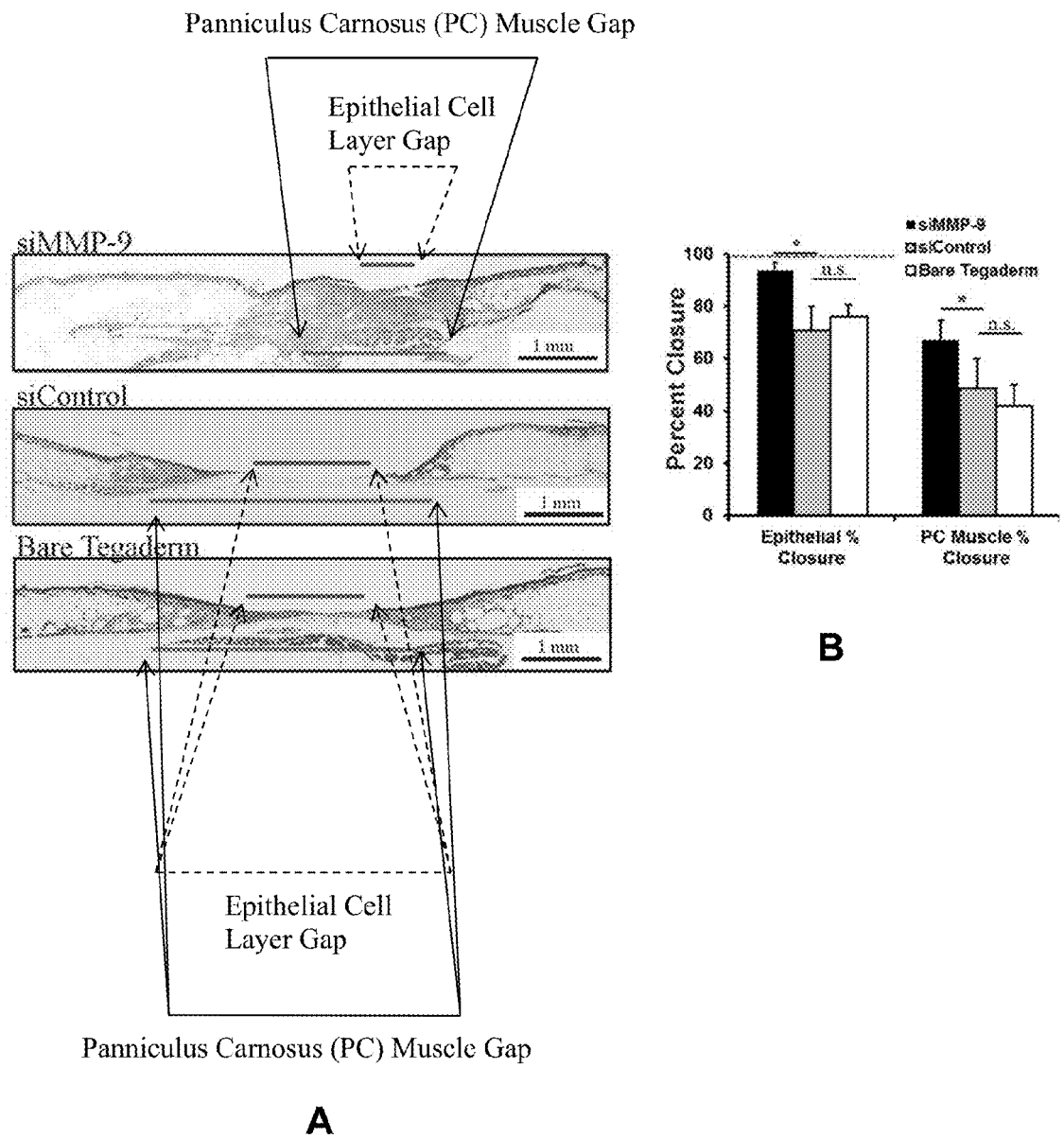
FIG. 33. Histological Analysis of Wound Closure at Two Weeks in accordance with certain embodiments of the present invention. (A) Comparison of closure of epithelium and panniculus carnosus muscle in treated and untreated mice as percent of initial wound total area. (B) H&E stained histology of center-of-wound sections. MMP-9 siRNA LbL Film treated wounds had significantly accelerated closure of both criteria measured.

In comparison to untreated wounds, MMP-9 siRNA treated wounds showed improved re-epithelialization and wound closure. Histology following one week of healing is shown in FIG. 32 for wounds treated with MMP-9 siRNA, siControl, and Bare Tegaderm®. Hematoxylin and eosin stained the wounds to visualize healing. After one week of healing, wounds treated with MMP-9 siRNA containing film coated bandages had significantly improved re-epithelialization and increased percentage wound contraction. FIG. 33 shows the histology following two weeks of healing for wounds treated with MMP-9 siRNA, siControl, and Bare Tegaderm®. Again, Hematoxylin and eosin stained the wounds to visualize healing. After two weeks of healing, wounds treated with MMP-9 siRNA containing film coated bandages had nearly complete re-epithelialization and a significantly higher percentage of epithelial and Panniculus Carnosus (PC) muscle closure compared with wounds exposed to siControl or Bare Tegaderm®.

Figure 34:
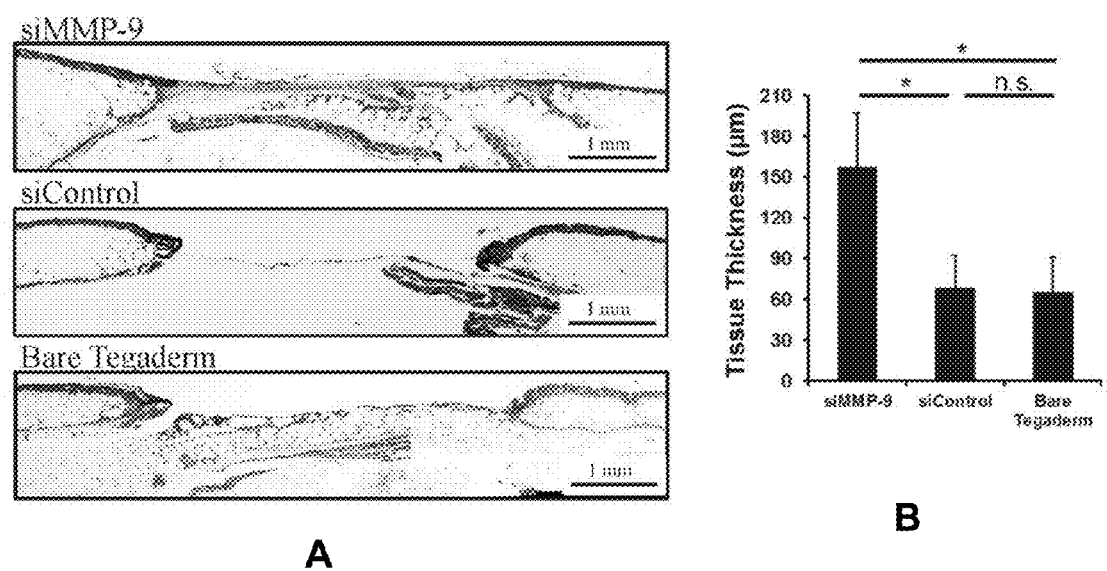
FIG. 34. Collagen Deposition within the Healing Wound Closure at One Week in accordance with certain embodiments of the present invention. (A) Masson's Trichrome staining showed increased collagen deposition within the formed tissue for wound's treated with MMP-9 siRNA over untreated wounds (colors removed). (B) Graph showing comparison of tissue thickness.
Figure 35:
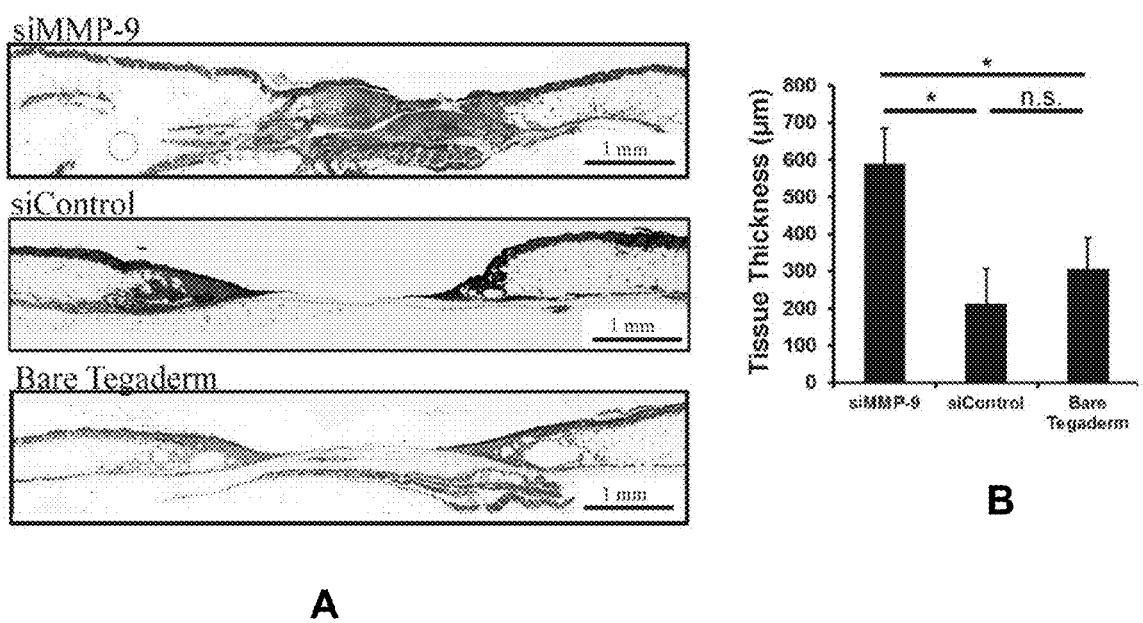
FIG. 35. Collagen Deposition within the Healing Wound Closure at Two Weeks in accordance with certain embodiments of the present invention. (A) Masson's Trichrome staining showed increased collagen deposition within the formed tissue for wound's treated with MMP-9 siRNA over untreated wounds (colors removed). (B) Graph showing comparison of tissue thickness.

Masson's Trichrome shows a marked increase in tissue thickness in MMP-9 siRNA treated wound over wounds exposed to either siControl or Bare Tegaderm®. FIG. 34 depicts wounds treated with MMP-9 siRNA, siControl, and Bare Tegaderm®. Wounds treated with MMP-9 siRNA containing film coated bandages showed significantly increased collagen deposition within the wound bed in comparison to wounds healing over the same period exposed to siControl films or Bare Tegaderm®. The bar chart on FIG. 34 also show wounds treated with MMP-9 siRNA had more than twice the average mid-wound tissue thickness in comparison to the untreated wounds. Masson's Trichrome at two weeks of healing for wounds treated with MMP-9 siRNA, siControl, and Bare Tegaderm® is demonstrated in FIG. 35. The bar chart shows MMP-9 siRNA treated wounds having center of the wound tissue thickness nearly three times as thick as untreated wounds. Further, FIG. 35 shows significantly increased collagen deposition within the wound bed for treated wounds.

Figure 36:
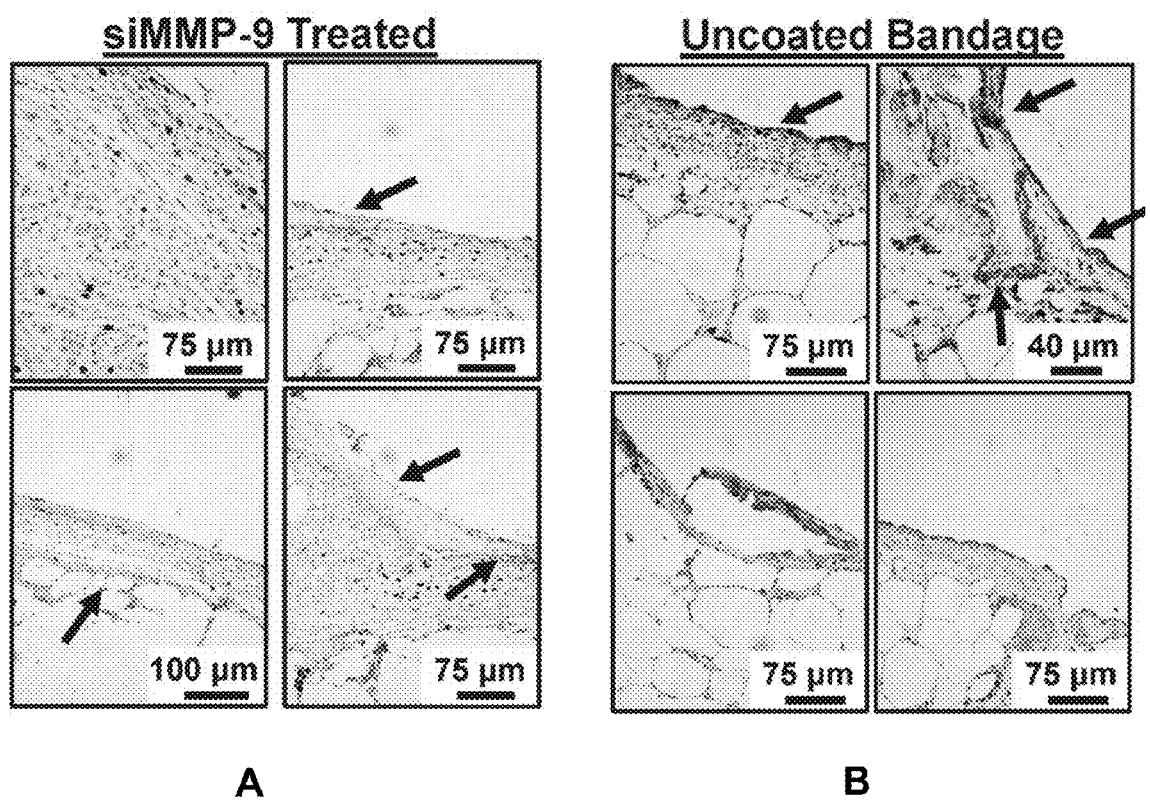
FIG. 36. IHC Analysis of siRNA Treated Wounds at One Week. (A) MMP-9 siRNA (at several scale measurements). (B) Uncoated bandage (at several scale measurements).
Figure 37:
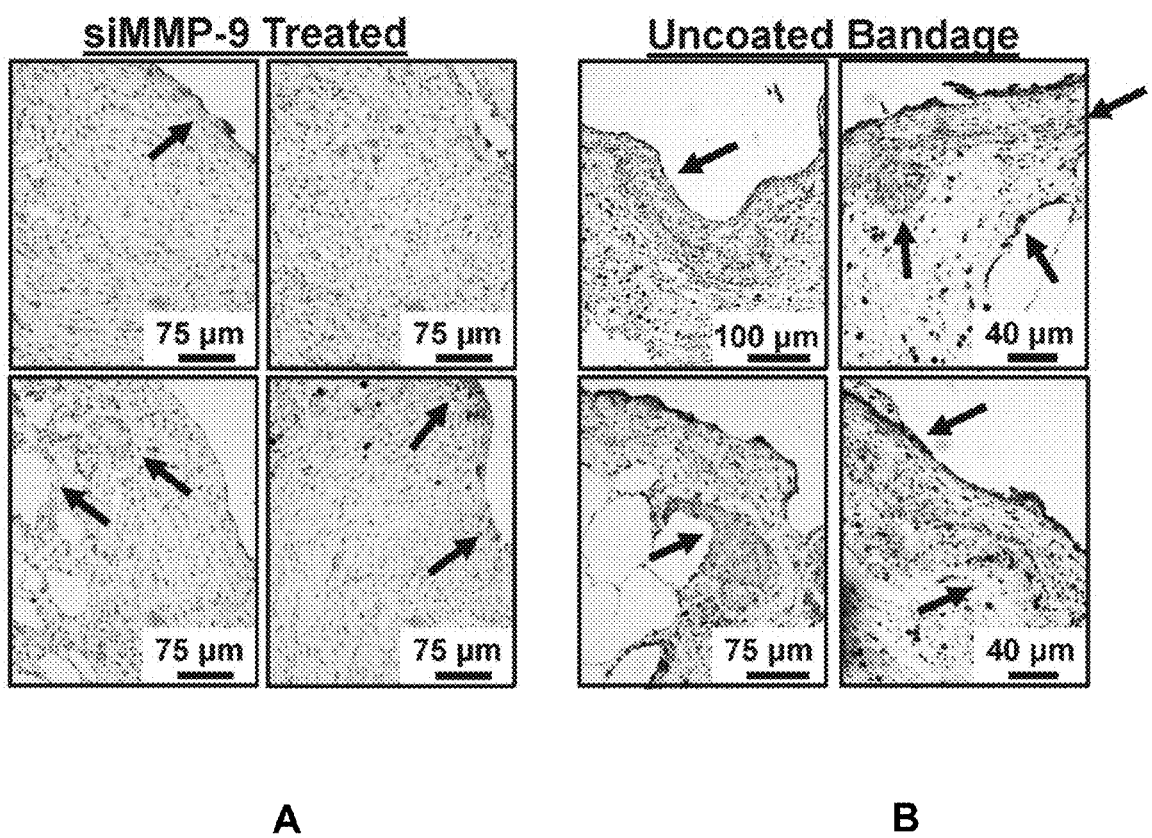
FIG. 37. IHC Analysis of siRNA Treated Wounds at Two Weeks. (A) MMP-9 siRNA (at several scale measurements). (B) Uncoated bandage (at several scale measurements).

Immunohistochemistry (IHC) analysis of MMP-9 siRNA treated and untreated wounds demonstrates that expression of MMP-9 is much higher in the untreated wound than the siMMP-9 treated wounds. The IHC slides of FIG. 36 shows MMP-9 siRNA treated v. uncoated bandages after one week. MMP-9 is identified via a horseradish peroxidase (HRP) antibody specific to it. The HRP antibody is a conjugated antibody that stains the slide brown where the primary antibody bound. The amount and intensity of the staining on the slides represents where MMP-9 is found resulting in a quantitative representative to the level of MMP-9 expression. FIG. 37 is an IHC slide showing MMP-9 expression for MMP-9 siRNA treated v. uncoated bandages after two weeks. It is thus apparent that the expression of MMP-9 is much higher in the untreated wound than the siMMP-9 treated wounds. This is an important point as it confirms lowered protein expression with lower mRNA.

Reduced MMP-9 expression correlates with improvements in wound healing. Comparing films treated with MMP-9 siRNA with untreated films showed both increased collagen deposition and retention within the wound bed of treated films. MMP-9 siRNA treated wounds further showed improved granulation tissue formation and increased wound contraction, that is, closing of the PC muscle gap. Moreover, MMP-9 siRNA treated films also resulted accelerated re-epithelialization in wound area and faster wound closure, or in other words, closing of the epithelial cell layer gap. Ultimately, reduced MMP-9 is shown to correlate faster and improved wound healing resulting in reduced risk of developing infections. Examples contained herein demonstrate effective MMP-9 siRNA delivery and knockdown. LbL films incorporating MMP-9 siRNA were assembled on CaP nanoparticle containing LbL film or (Chitosan/siRNA)$_{50}$ bilayer film built on top of a (Poly2/dextran sulfate)$_{10}$ degradable baselayer LbL film. In both cases, resultant assemblies were tested in vivo achieving significant reduction of MMP-9 expression. Together these MMP-9 siRNA assemblies present a clear case that the reduction of MMP-9 expression within the wound by RNA interference leads to improved diabetic wound healing.

In addition to LbL films as described herein, other exemplary LbL films in accordance with some embodiments of the present invention can include, but are not limited to, LPEI/siRNA/Poly2/siRNA, LPEI/siRNA/Poly2/Dextran sulfate (DS), Poly-1-lysine (PLL)/siRNA, PLL/siRNA/Poly2/DS, PLL/siRNA/PLLIDS, PLL!siRNA/LPEI/DS, PrS/siRNA, PrS/siRNA/Poly2/DS, PrS/siRNA/PrS/DS, (Degradable baselayers)$_{10}$-PLL/siRNA, (Degradable baselayers)$_{10}$-PrS/siRNA, Poly-allylamine hydrochloride (PAH)/siRNA, PAH/siRNA/Poly2/siRNA, Chitosan! siRNA/Poly2/siRNA, ChitosanlsiRNA/Chitosan/DS, Chitosan/siRNA/Poly2/Laponite®, LPEI/siRNA/LPEI/IDS/ Poly2/DS and modifications/combination thereof.

Example 6

In some embodiments, films that directly incorporate siRNA (e.g, without CaP nanoparticles) are particularly usefully for delivery of multiple siRNAs with separate release profiles. The present Example confirms that, as described herein, the efficacy of direct incorporation of multiple siRNAs for effective delivery from LbL systems. siRNA incorporation is easily controlled through by their stoichiometric ratios within an assembly bath. In some embodiments, films are used for delivery of pre-set cocktail siRNAs. Multiple siRNA assemblies created using siRNA assembly methods, wherein multi-gene knockdown results.

Figure 38:
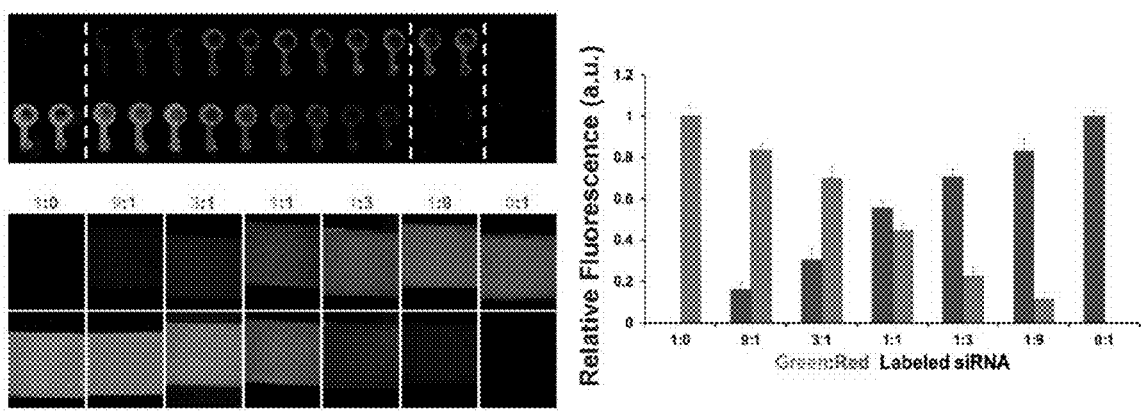
FIG. 38. Image and graph showing relative fluorescence of incorporation of Multiple siRNAs.

RNA interference provides a powerful tool for modifying protein expression. However, biological systems are complex and a simple single target approach is unlikely to result in consistent, meaningful changes within the tissue. FIG. 38 demonstrates incorporation of multiple siRNAs. It is believed that a multiple knockdown approach is likely to increase efficacy.

Figure 39:
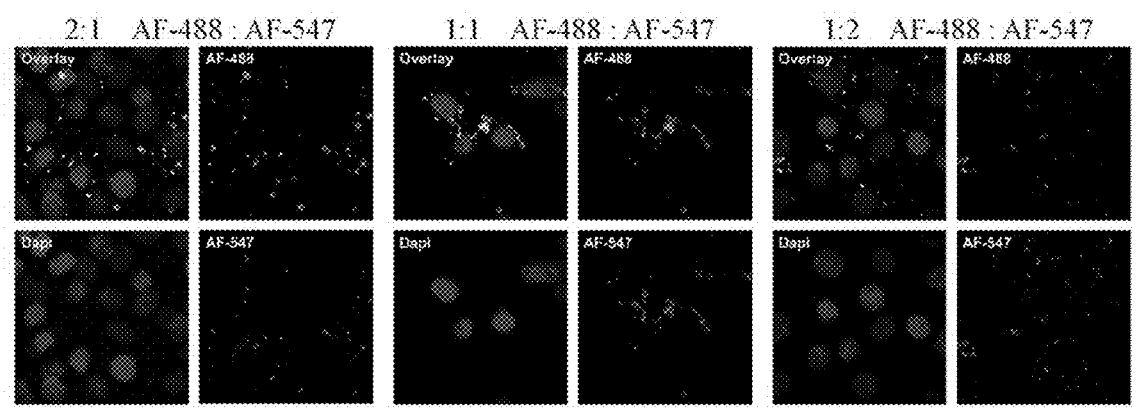
FIG. 39. Images of in vitro Delivery of Multiple siRNAs from a Single LbL film.

FIG. 39 demonstrates delivery of multiple siRNAs in vitro from a single LbL film showing successful simultaneous knocked down of two separate genes with control over extent of knockdown of each gene as well as the sequential knockdown of both reporter genes.

In some embodiments, the LbL films with incorporated nucleic acid agents as described herein have been coated onto microparticles. According to some embodiments, the microparticles are suited for combination in creams or gels. Microparticle coated LbL films incorporating nucleic acid agents when combined into a cream or gel dosage form are particularly useful because they associate sustained release with the ability to vary both dosage and area of coverage.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

We claim:

1. A structure for localized and controlled release of nucleic acid agents comprising:
a bandage substrate; and
a multilayer film coated on the substrate, wherein adjacent layers of the multilayer film are associated with one another via one or more non-covalent interactions,
wherein the multilayer film includes:
a first bilayer portion; and
a second bilayer portion adjacent to the first bilayer portion, wherein the second bilayer portion is disposed on the bandage substrate, and
wherein:
the first bilayer portion includes at least fifty bilayers, each bilayer of the first bilayer portion comprising a first layer comprising an siRNA agent, and a second layer comprising chitosan,
the second bilayer portion includes at least ten bilayers, each bilayer of the second bilayer portion comprising a first layer comprising dextran sulfate and a second layer comprising a poly(β-amino ester) having the following structural formula:

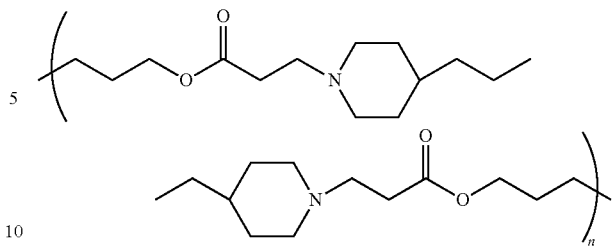

wherein n is an integer greater than or equal to 5.

2. The structure of claim 1, wherein loading density of the siRNA agent is at least about 1 μg/cm$^2$, at least about 2 μg/cm$^2$, at least about 5 μg/cm$^2$, at least about 8 μg/cm$^2$, at least about 10 μg/cm$^2$, at least about 12 μg/cm$^2$, at least about 15 μg/cm$^2$, at least about 18 μg/cm$^2$, at least about 20 μg/cm$^2$, at least about 25 μg/cm$^2$, at least about 30 μg/cm$^2$, at least about 50 μg/cm$^2$, or at least about 100 μg/cm$^2$.

3. The structure of claim 1, wherein the siRNA agent inhibits expression of a polypeptide.

4. The structure of claim 3, wherein the polypeptide is selected from the group consisting of matrix metallopeptidase 9 (MMP-9), neutral endopeptidase (NEP) and protein tyrosine phosphatase 1B (PTP1B).

5. The structure of claim 1, wherein the multilayer film comprises 60, 80, 100, 150 or 200 bilayers.

6. The structure of claim 1, further comprising an additional agent.

7. The structure of claim 6, wherein the additional agent is selected from one or more members of the group consisting of an antibiotic and an anti-inflammatory agent.

8. The structure of claim 1, wherein the substrate comprises at least a portion of a medical device.

9. The structure of claim 1, wherein the substrate is a wound dressing.

10. The structure of claim 1, wherein the multilayer film further comprises a second nucleic acid agent present at a loading density of at least about 1 μg/cm$^2$.

11. The structure of claim 10, wherein the siRNA agent and second nucleic acid agent are presented at a predetermined ratio.

* * * * *